United States Patent
Boggs, II

(10) Patent No.: US 11,420,057 B2
(45) Date of Patent: Aug. 23, 2022

(54) SYSTEMS AND METHODS TO PLACE ONE OR MORE LEADS IN TISSUE FOR PROVIDING FUNCTIONAL AND/OR THERAPEUTIC STIMULATION

(71) Applicant: SPR Therapeutics, Inc., Cleveland, OH (US)

(72) Inventor: Joseph W. Boggs, II, Chapel Hill, NC (US)

(73) Assignee: SPR Therapeutics, Inc., Cleveland, OH (US)

(*) Notice: Subject to any disclaimer, the term of this patent is extended or adjusted under 35 U.S.C. 154(b) by 0 days.

(21) Appl. No.: 16/587,527

(22) Filed: Sep. 30, 2019

(65) Prior Publication Data

US 2020/0030606 A1 Jan. 30, 2020

Related U.S. Application Data

(63) Continuation of application No. 15/888,338, filed on Feb. 5, 2018, now Pat. No. 10,426,959, which is a continuation of application No. 15/132,832, filed on Apr. 19, 2016, now Pat. No. 9,884,189, which is a continuation of application No. 14/522,918, filed on Oct. 24, 2014, now abandoned, which is a continuation-in-part of application No. 12/653,023, filed on Dec. 7, 2009, now Pat. No. 8,954,153, and a continuation-in-part of application No. 12/653,029, filed on Dec. 7, 2009, now abandoned.

(60) Provisional application No. 61/201,030, filed on Dec. 5, 2008.

(51) Int. Cl.
*A61N 1/36* (2006.01)
*A61N 1/05* (2006.01)

(52) U.S. Cl.
CPC ....... *A61N 1/36071* (2013.01); *A61N 1/0551* (2013.01); *A61N 1/0558* (2013.01); *A61N 1/36017* (2013.01); *A61N 1/36021* (2013.01)

(58) Field of Classification Search
None
See application file for complete search history.

(56) References Cited

U.S. PATENT DOCUMENTS

| | | | |
|---|---|---|---|
| 4,144,889 A | 3/1979 | Tyers et al. |
| 5,036,862 A | 8/1991 | Pohndorf |
| 5,830,151 A | 11/1998 | Hadzic et al. |
| 6,058,938 A | 5/2000 | Chu et al. |
| 6,104,957 A | 8/2000 | Alo |
| 6,381,496 B1 | 4/2002 | Meadows et al. |

(Continued)

FOREIGN PATENT DOCUMENTS

| | | |
|---|---|---|
| AU | 2009322895 | 6/2011 |
| AU | 2009322898 | 7/2011 |
| WO | 2010065146 | 6/2010 |

OTHER PUBLICATIONS

International Preliminary Report on Patentability dated Jan. 7, 2011 in International Application Serial No. PCT/US2009/006403.

(Continued)

*Primary Examiner* — Brian T Gedeon
(74) *Attorney, Agent, or Firm* — McDonald Hopkins LLC

(57) ABSTRACT

Systems and methods make possible the placement of one or more electrode leads in a tissue region for providing functional and/or therapeutic stimulation to tissue. The systems and methods are adapted to provide the relief of pain.

26 Claims, 25 Drawing Sheets

(56) References Cited

U.S. PATENT DOCUMENTS

| | | |
|---|---|---|
| 7,079,882 B1 | 7/2006 | Schmidt |
| 7,359,751 B1 | 4/2008 | Erickson et al. |
| 7,373,204 B2 | 5/2008 | Gelfand et al. |
| 7,613,519 B2 | 11/2009 | DeRidder |
| 7,720,548 B2 | 5/2010 | King |
| 7,945,330 B2 | 5/2011 | Gliner et al. |
| 8,103,341 B2 | 1/2012 | Libbus et al. |
| 8,204,607 B2 | 6/2012 | Rooney |
| 8,239,029 B2 | 8/2012 | Ridder |
| 8,954,153 B2 | 2/2015 | Boggs et al. |
| 2003/0078633 A1* | 4/2003 | Firlik ............ A61N 1/36071 607/46 |
| 2004/0015204 A1 | 1/2004 | Whitehurst |
| 2004/0049240 A1 | 3/2004 | Gerber et al. |
| 2004/0186532 A1 | 9/2004 | Tadlock |
| 2005/0010259 A1 | 1/2005 | Gerber |
| 2005/0085870 A1* | 4/2005 | Goroszeniuk ...... A61N 1/37205 607/46 |
| 2005/0143789 A1 | 6/2005 | Whitehurst |
| 2006/0069415 A1 | 3/2006 | Cameron et al. |
| 2006/0095088 A1 | 5/2006 | De Ridder |
| 2006/0173507 A1 | 8/2006 | Mrva et al. |
| 2006/0206162 A1* | 9/2006 | Wahlstrand ........ A61N 1/0456 607/46 |
| 2007/0021803 A1 | 1/2007 | Deem et al. |
| 2007/0027514 A1 | 2/2007 | Gerber |
| 2007/0073357 A1 | 3/2007 | Rooney et al. |
| 2007/0150034 A1 | 6/2007 | Rooney et al. |
| 2007/0255365 A1 | 11/2007 | Gerber et al. |
| 2007/0255368 A1* | 11/2007 | Bonde ............... A61N 1/0558 607/116 |
| 2010/0036454 A1 | 2/2010 | Bennett et al. |
| 2010/0152809 A1 | 6/2010 | Boggs et al. |

OTHER PUBLICATIONS

International Preliminary Report on Patentability, PCT/US09/06414, dated Jan. 5, 2011.

International Search Report and Written Opinion dated Feb. 3, 2010 in International Application Serial No. PCT/US2009/006414.

International Search Report and Written Opinion; PCT/US09/06403; datedFeb. 23, 2010.

Office Action in connection with PCT US2009006414 dated Sep. 20, 2019, 4 pages.

* cited by examiner

Stump

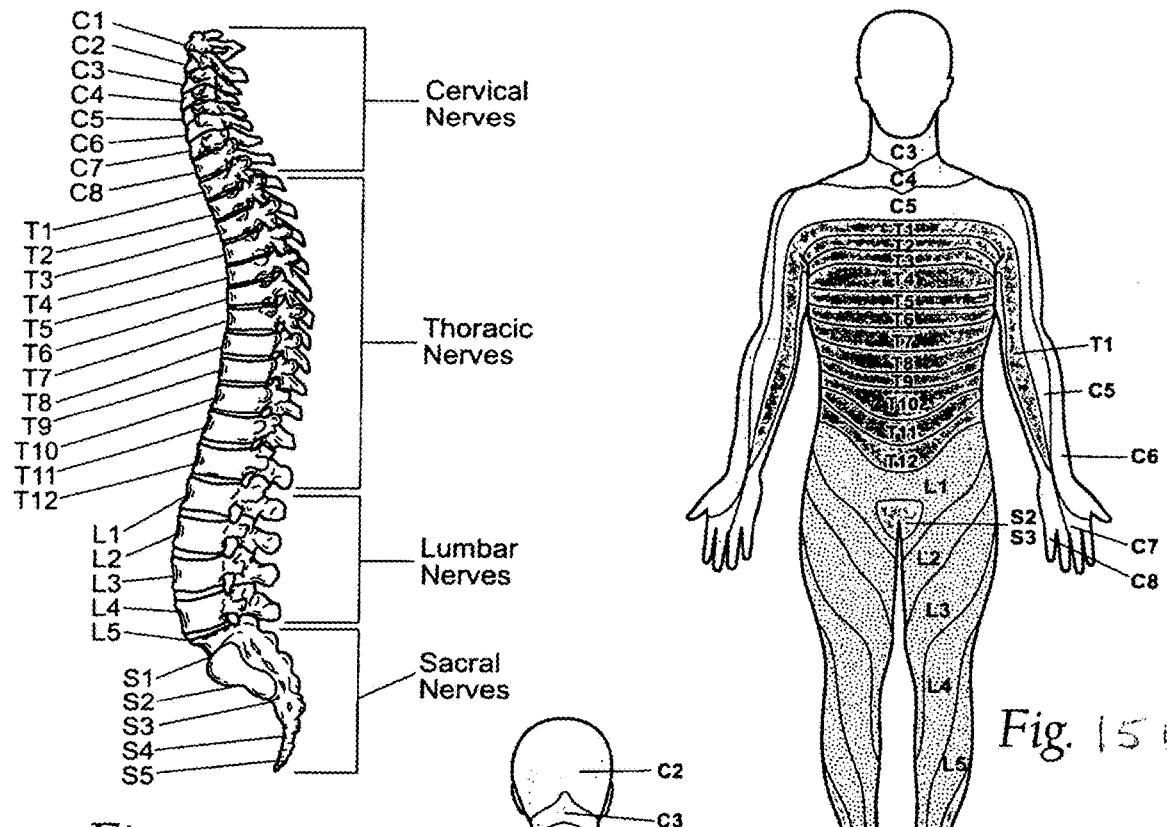
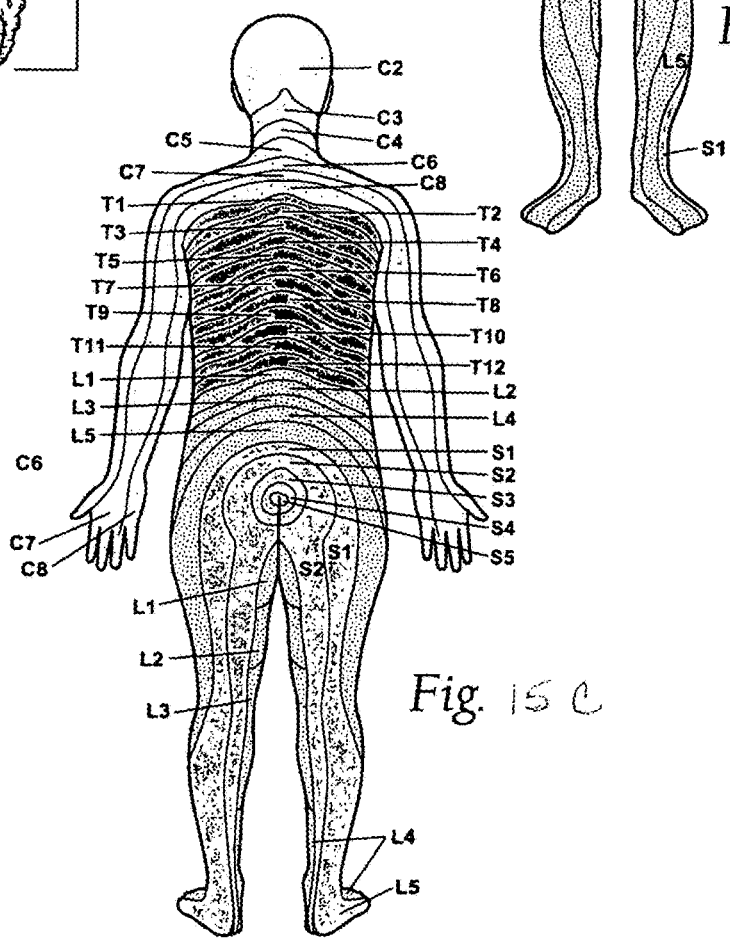
Fig. 15A
Fig. 15B
Fig. 15C

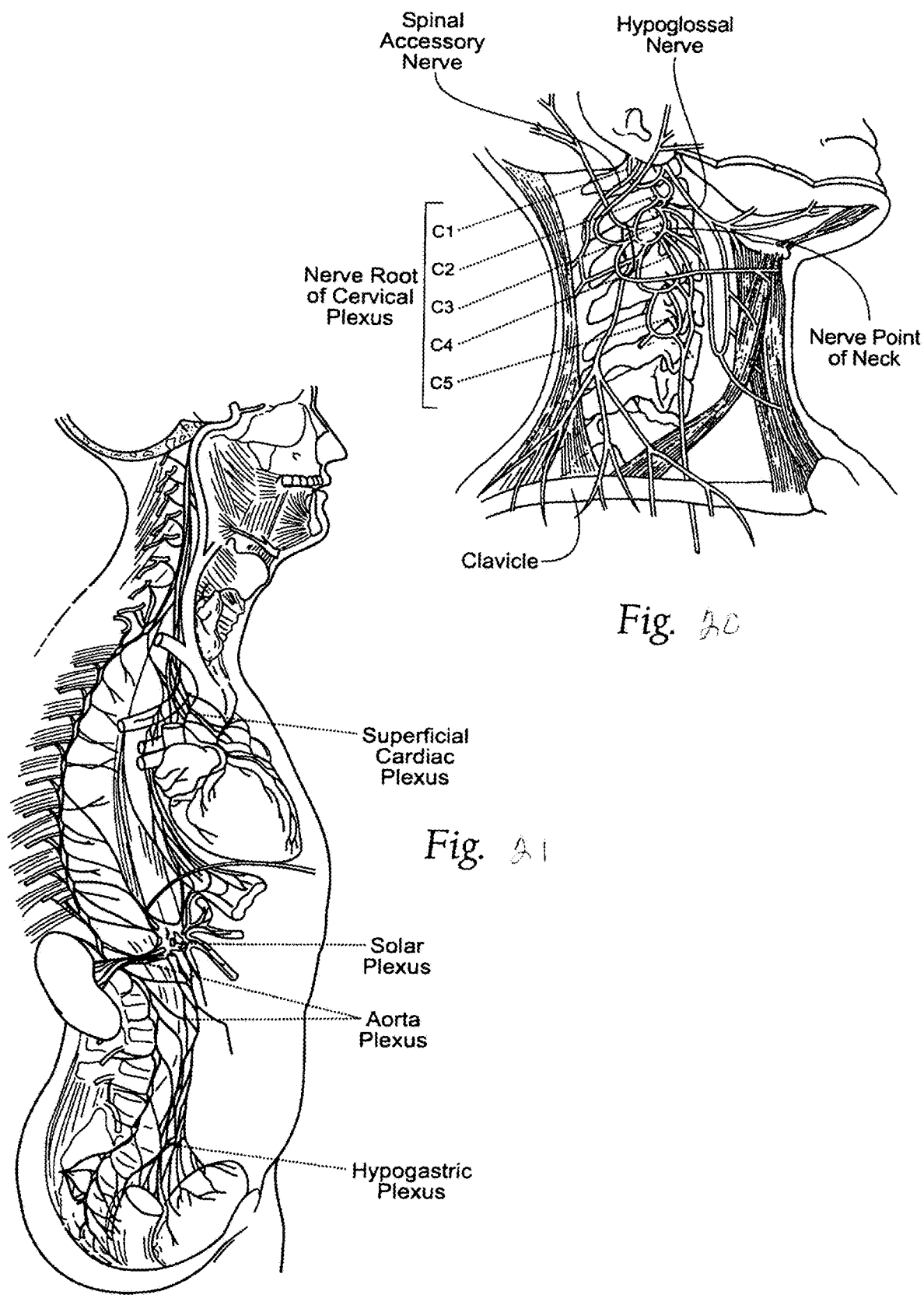

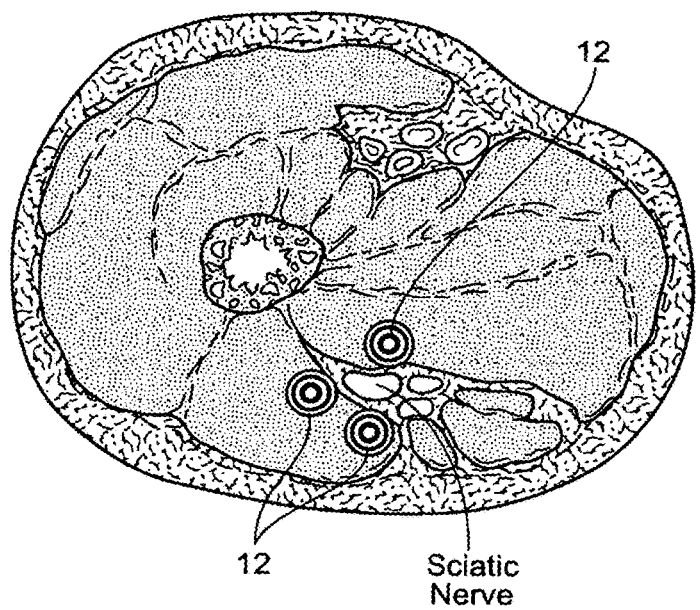
Fig. 32A
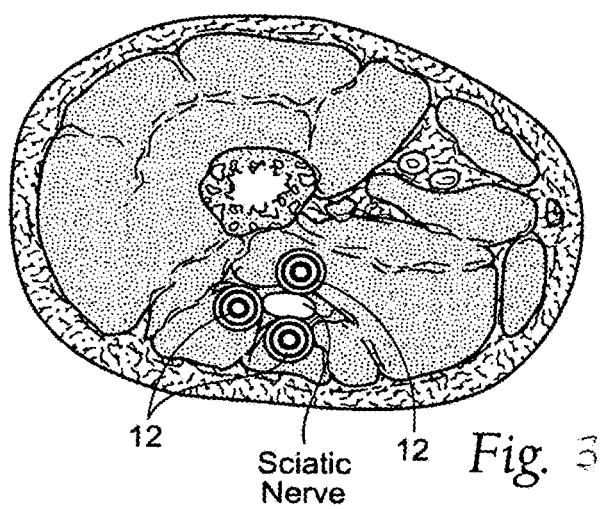
Fig. 32B
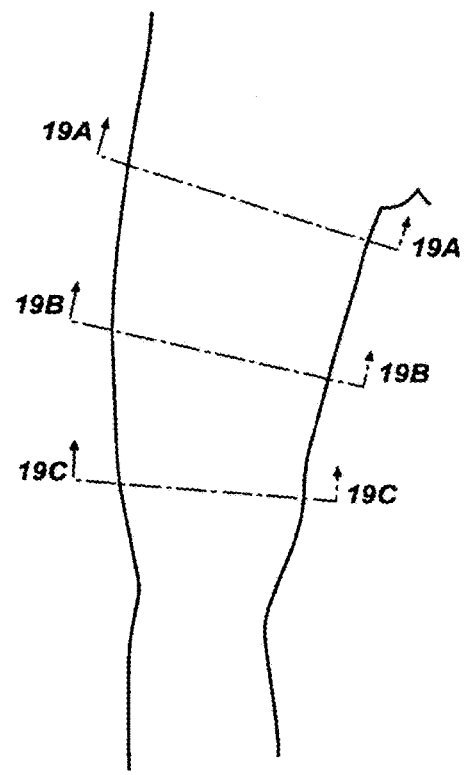
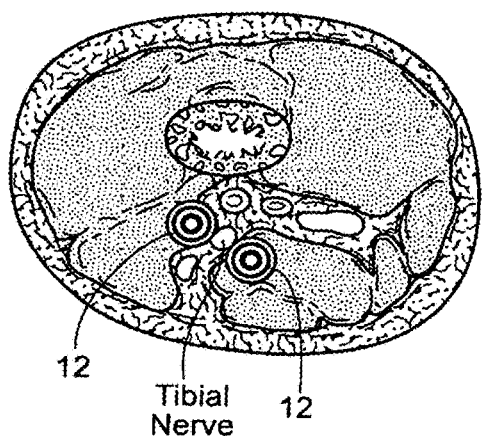
Fig 32C

SYSTEMS AND METHODS TO PLACE ONE OR MORE LEADS IN TISSUE FOR PROVIDING FUNCTIONAL AND/OR THERAPEUTIC STIMULATION

RELATED APPLICATIONS

This application is a continuation of U.S. patent application Ser. No. 15/888,338 filed Feb. 5, 2018, and entitled "Systems and Methods to Place One or More Leads in Tissue for Providing Functional and/or Therapeutic Stimulation," which is a continuation of U.S. patent application Ser. No. 15/132,832, filed Apr. 19, 2016, and entitled "Systems and Method to Place One or More Leads in Tissue for Providing Functional and/or Therapeutic Stimulation," now U.S. Pat. No. 9,884,189, which is a continuation of U.S. patent application Ser. No. 14/522,918, filed Oct. 24, 2014, and entitled "Systems and Methods to Place One or More Leads in Tissue for Providing Functional and/or Therapeutic Stimulation," now abandoned, which is a continuation-in-part of U.S. patent application Ser. No. 12/653,029, filed Dec. 7, 2009, and entitled "Systems and Methods to Place One or More Leads in Tissue for Providing Functional and/or Therapeutic Stimulation," now abandoned, which claims the benefit of U.S. Provisional Patent Application Ser. No. 61/201,030, filed Dec. 5, 2008, and entitled "Systems and Methods to Place One or More Leads in Tissue for Providing Functional and/or Therapeutic Stimulation," which are all incorporated herein by reference. In addition, U.S. patent application Ser. No. 14/522,918 is also a continuation in part of U.S. patent application Ser. No. 12/653,023, now U.S. Pat. No. 8,954,153, filed Dec. 7, 2009, and entitled "Systems and Methods to Place One or More Leads in tissue for Providing Functional and/or Therapeutic Stimulation," which claims the benefit of U.S. Provisional Patent Application Ser. No. 61/201,030, filed Dec. 5, 2008, and entitled "Systems and Methods to Place One or More Leads in Tissue for Providing Functional and/or Therapeutic Stimulation," which are all incorporated herein by reference.

FIELD OF INVENTION

This invention relates to systems and methods for placing one or more electrode leads in tissue for providing electrical stimulation to tissue.

BACKGROUND OF THE INVENTION

Neurostimulation, i.e., neuromuscular stimulation (the electrical excitation of nerves and/or muscle to directly elicit the contraction of muscles) and neuromodulation stimulation (the electrical excitation of nerves, often afferent nerves, to indirectly affect the stability or performance of a physiological system) and brain stimulation (the stimulation of cerebral or other central nervous system tissue) can provide functional and/or therapeutic outcomes. While existing systems and methods can provide remarkable benefits to individuals requiring neurostimulation, many quality of life issues still remain. For example, existing systems include complicated procedures to place electrodes and pulse generators, and issues remain with the migration of electrodes which eventually reduce the effectiveness of the neurostimulation. Furthermore, these systems are, by today's standards, relatively large and awkward to manipulate, transport, and adhere to the patient.

There exist both external and implantable devices for providing neurostimulation in diverse therapeutic and functional restoration indications. These neuro-stimulators are able to provide treatment and/or therapy to individual portions of the body. The operation of these devices typically includes the use of an electrode placed either on the external surface of the skin and/or a surgically implanted electrode. In the case of external neurostimulators, surface electrode(s) and/or percutaneous lead(s) having one or more electrodes may be used to deliver electrical stimulation to the select portion of the patient's body.

One example of an indication where therapeutic treatment may be provided is for the treatment of pain, such as to provide a therapy to reduce pain in individuals with amputated limbs. Amputation leads to chronic pain in almost all (95%) patients, regardless of how much time had passed since the amputation (Ephraim et al, 2005). The pain can be extremely bothersome to amputees, significantly decrease their quality of life, correlate with increased risk of depression, and negatively affect their inter-personal relationships and their ability to return to work (Kashani et al 1983; Blazer et al. 1994; Cansever et al. 2003). The present methods of treatment, which are primarily medications, are unsatisfactory in reducing amputation-related pain, have unwanted side effects, offer a low success rate, and often lead to addiction.

Most amputees have two types of pain: residual limb (stump) pain and phantom pain. Approximately 72-85% of amputees have phantom pain and 68-76% of amputees have residual limb (stump) pain (Sherman and Sherman 1983; Sherman et al. 1984; Ehde et al. 2000; Ephraim et al. 2005). Both stump pain and phantom limb pain are chronic pains experienced after an amputation, and they are easily distinguished by the perceived location of the pain. Stump pain is sensed in the portion of the limb that remains after amputation, and phantom limb pain is perceived in the portion of the limb that has been removed. Typically, amputee patients with severe stump pain also have severe phantom limb pain, but it is recommended that their responses to treatment be measured independently (Jensen et al. 1985; Kooijman et al. 2000). Stump and phantom pain can be severe and debilitating to a large proportion of persons with amputations, who will unfortunately often progress through a battery of management techniques and procedures without finding relief from their pain (Bonica 1953; Sherman et al. 1980; Ehde et al. 2000; Loeser 2001a; Ephraim et al. 2005).

An estimated 80-95% of 1.7 millions persons who currently live with amputations plus the additional 185,000 persons expected to undergo amputation each year in the United States will suffer from stump and/or phantom pain at an annual direct cost of $1.4-2.7 billion and overall associated costs of $13 billion (Sherman and Sherman 1983; Sherman et al. 1984; Ehde et al. 2000; Mekhail et al. 2004; Ephraim et al. 2005). Severe post-amputation pain often leads to further disability, reduced quality of life, and frequently interferes with the simple activities of daily life more than the amputation itself (Millstein et al. 1985; Schoppen et al. 2001; Marshall et al. 2002; Whyte and Carroll 2002; Rudy et al. 2003), and no available therapy is sufficient to manage it (Sherman et al, 1980; Jahangiri et al. 1994; Rosenquist and Haider 2008).

Many techniques have been developed to treat post-amputation pain, but all of them are ultimately insufficient (Jahangiri et al. 1994). A review in 1980 found that none of the 68 treatments available for post-amputation pain were uniformly successful (Sherman et al. 1980), and more recent reviews have found that little has changed and there remains a large need for an effective method of treating stump and phantom pain (Davis 1993; Wall et al. 1994; Loeser 2001a;

Halbert et al. 2002; Rosenquist and Haider 2008). Some studies report that as few as 1% of amputees with severe phantom and stump pain receive lasting benefit from any of the available treatments (Sherman and Sherman 1983; Sherman et al. 1984). Presently, most patients are managed with medications, but approximately a third of amputees still report severe (intensity of 7-10 on a scale of 0-10) phantom and stump pain.

Non-narcotic analgesics, such as acetaminophen or non-steroidal anti-inflammatory drugs (NSAIDS), have relatively minor side effects and are commonly used for several types of pain. However, they are not specific to stump or phantom pain and are rarely sufficient in managing moderate to severe chronic post-amputation pain (Sherman et al. 1980; Loeser 2001a; Rosenquist and Haider 2008).

The use of narcotic analgesics, such as N-methyl-D-aspartate (NDMA) antagonists, has shown only minor success with inconsistent results. Narcotics carry the risk of addiction and side effects, such as nausea, confusion, vomiting, hallucinations, drowsiness, dizziness, headache, agitation, and insomnia. Several trials of multiple narcotic agents have failed to show statistically significant improvement in phantom pain (Stangl and Loeser 1997; Nikolajsen et al. 2000; Loeser 2001a, Maier et al. 2003; Hayes et al. 2004; Wiech et al. 2004; Rosenquist and Haider 2008).

Physical methods such as adjusting the prosthesis may be helpful, but only if the pain is due to poor prosthetic fit. Other physical treatments, including acupuncture, massage, and percussion or heating/cooling of the stump, have few complications but also have limited data to support their use and have not been well accepted clinically (Russell and Spalding 1950; Gillis 1964; Monga and Jaksic 1981; Loeser 2001a).

Psychological strategies, such as biofeedback and psychotherapy, may be used as an adjunct to other therapies but are seldom sufficient, and there are few studies demonstrating efficacy and these approaches are not specific to stump or phantom pain (Dougherty 1980; Sherman 1980). Mirror-box therapy has demonstrated mixed results and is not widely used in clinical practice (Ramachandran and Rogers-Ramachandran 1996; Brodie et al. 2007; Chan et al. 2007; Rosenquist and Haider 2008).

Many surgical procedures have been attempted, but few are successful and most are contraindicated for the majority of the amputee patients (Loeser 2001a). Because neuromas are implicated with stump and phantom pain, there have been many attempts to remove them surgically, but ultimately a new neuroma will develop each time a nerve is cut and the pain relief only lasts for the 3 weeks that it takes for a new neuroma to form (Sturm 1975; Sunderland 1978; Sherman 1980). Furthermore, neuroablative procedures carry the risk of producing deafferentation pain, and any surgical procedure has a greater chance of failure than success (Loser 2001a; Rosenquist and Haider 2008). Thus, present medical treatments of stump and phantom pain are inadequate, and most sufferers resort to living with pain that is poorly controlled with medications.

Electrical stimulation systems hold promise for relief of post-amputation pain, but widespread use of available systems is limited.

Transcutaneous electrical nerve stimulation (TENS) has been cleared by the FDA for treatment of pain and may be successful in reducing post-amputation pain. TENS systems are external neurostimulation devices that use electrodes placed on the skin surface to activate target ne yes below the skin surface. TENS has a low rate of serious complications, but it also has a relatively low (i.e., less than 25%) long-term rate of success.

Application of transcutaneous electrical nerve stimulation (TENS) has been used to treat stump and phantom pain successfully, but it has low long-term patient compliance, because it may cause additional discomfort by generating cutaneous pain signals due to the electrical stimulation being applied through the skin, and the overall system is bulky, cumbersome, and not suited for long-term use (Nashold and Goldner 1975; Sherman 1980; Finsen et al. 1988).

Spinal cord stimulation (SCS) systems are FDA approved as implantable neurostimulation devices marketed in the United States for treatment of pain. Similar to TENS, when SCS evokes paresthesias that cover the region of pain, it confirms that the location of the electrode and the stimulus intensity should be sufficient to provide pain relief and pain relief can be excellent initially, but maintaining sufficient paresthesia coverage is often a problem as the lead migrates along the spinal canal (Krainick et al. 1980; Sharan et al. 2002; Buchser and Thomson 2003).

Lead migration is the most common complication for spinal cord stimulators occurring in up to 45-88% of the cases (North et al. 1991; Andersen 1997; Spincemaille et al. 2000; Sharan et al. 2002). When the lead migrates, the active contact moves farther from the target fibers and loses the ability to generate paresthesias in the target area. SCS systems attempt to address this problem by using leads with multiple contacts so that as the lead travels, the next contact in line can be selected to be the active contact.

Spinal cord stimulation is limited by the invasive procedure and the decrease in efficacy as the lead migrates. When it can produce paresthesias in the region of pain, spinal cord stimulation is typically successful initially in reducing stump and phantom pain, but over time the paresthesia coverage and pain reduction is often lost as the lead migrates away from its target (North et al. 1991; Andersen 1997; Loeser 2001a).

Brain stimulation systems are limited by the lack of patient selection criteria and the lack of studies demonstrating long-term efficacy.

Peripheral nerve stimulation may be effective in reducing post-amputation pain, but it previously required specialized surgeons to place cuff- or paddle-style leads around the nerves in a time consuming procedure.

Immediately following amputation, all patients experience short-term (postoperative) pain, but it usually resolves within a month as the wound heals. In contrast, a long-term pain often develops and persists in the stump and phantom limb after the amputated limb has healed into a healthy stump. Stump and phantom pain are thought to have a peripheral and central component, and both components may be mediated by stimulating the peripheral nerves that were transected during amputation.

Neuromas develop when a peripheral nerve is cut and the proximal portion produces new axon growth that forms a tangled mass as it fails to connect with the missing distal portion of the nerve. All amputations produce neuromas and not all neuromas are painful, but neuromas are thought to be a major source of pain after amputation (Burchiel and Russell 1987; Loeser 2001a; Rosenquist and Haider 2008). Neuromas may generate spontaneous activity (Wall and Gutnick 1974), and the level of activity in afferent fibers innervating the region of pain has been linked to the level of post-amputation pain (Nyström and Hagbarth 1981).

As previously described, electrical stimulation has been used and shown to be effective in treating amputee pain, but present methods of implementation have practical limitations that prevent widespread use. External systems are too cumbersome, and implanted spinal cord stimulation systems often have problems of lead migration along the spinal canal, resulting in either the need for frequent reprogramming or clinical failure.

It is time that systems and methods for providing neurostimulation address not only specific prosthetic or therapeutic objections, but also address the quality of life of the individual requiring neurostimulation, including a need to treat amputee pain with minimally-invasive systems and methods that may not require reprogramming, and include lead(s) that can be inserted percutaneously near target peripheral nerve(s) and resist(s) migration.

The electrical stimulation of nerves, often afferent nerves, to indirectly affect the stability or performance of a physiological system can provide functional and/or therapeutic outcomes, and has been used for activating target nerves to provide therapeutic relief of pain.

While existing systems and methods can provide remarkable benefits to individuals requiring therapeutic relief, many issues and the need for improvements still remain.

Many techniques have been developed to treat pain, but all of them are ultimately insufficient.

Non-narcotic analgesics, such as acetaminophen or non-steroidal anti-inflammatory drugs (NSAIDS), have relatively minor side effects and are commonly used for several types of pain. However, they are rarely sufficient in managing moderate to severe chronic pain (Sherman et al. 1980; Loeser 2001a; Rosenquist and Haider 2008).

The use of narcotic analgesics, such as N-methyl-D-aspartate (NDMA) antagonists, has shown only minor success with inconsistent results Narcotics carry the risk of addiction and side effects, such as nausea, confusion, vomiting, hallucinations, drowsiness, dizziness, headache, agitation, and insomnia.

Psychological strategies, such as biofeedback and psychotherapy, may be used as an adjunct to other therapies but are seldom sufficient, and there are few studies demonstrating efficacy.

Electrical stimulation systems have been used for the relief of pain, but widespread use of available systems is limited.

There exist both external and implantable devices for providing electrical stimulation to activate nerves and/or muscles to provide therapeutic relief of pain. These "neurostimulators" are able to provide treatment and/or therapy to individual portions of the body. The operation of these devices typically includes the use of an electrode placed either on the external surface of the skin and/or a surgically implanted electrode. In most cases, surface electrode(s), cuff-style electrode(s), paddle-style electrode(s), spinal column electrodes, and/or percutaneous lead(s) having one or more electrodes may be used to deliver electrical stimulation to the select portion of the patient's body.

Transcutaneous electrical nerve stimulation (TENS) has been cleared by the FDA for treatment of pain. TENS systems are external neurostimulation devices that use electrodes placed on the skin surface to activate target nerves below the skin surface. TENS has a low rate of serious complications, but it also has a relatively low (i.e., less than 25%) long-term rate of success.

Application of TENS has been used to treat pain successfully, but it has low long-term patient compliance, because it may cause additional discomfort by generating cutaneous pain signals due to the electrical stimulation being applied through the skin, and the overall system is bulky, cumbersome, and not suited for long-term use (Nashold and Goldner 1975; Sherman 1980; Finsen et al. 1988).

In addition, several clinical and technical issues associated with surface electrical stimulation have prevented it from becoming a widely accepted treatment method. First, stimulation of cutaneous pain receptors cannot be avoided resulting in stimulation-induced pain that limits patient tolerance and compliance. Second, electrical stimulation is delivered at a relatively high frequency to prevent stimulation-induced pain, which leads to early onset of muscle fatigue in turn preventing patients from properly using their arm. Third, it is difficult to stimulate deep nerves and/or muscles with surface electrodes without stimulating overlying, more superficial nerves and/or muscles resulting in unwanted stimulation. Finally, clinical skill and intensive patient training is required to place surface electrodes reliably on a daily basis and adjust stimulation parameters to provide optimal treatment. The required daily maintenance and adjustment of a surface electrical stimulation system is a major burden on both patient and caregiver.

Spinal cord stimulation (SCS) systems are FDA approved as implantable neurostimulation devices marketed in the United States for treatment of pain. Similar to TENS, when SCS evokes paresthesias that cover the region of pain, it confirms that the location of the electrode and the stimulus intensity should be sufficient to provide pain relief and pain relief can be excellent initially, but maintaining sufficient paresthesia coverage is often a problem as the lead migrates along the spinal canal (Krainick et al. 1980; Sharan et al. 2002; Buchser and Thomson 2003).

Spinal cord stimulation is limited by the invasive procedure and the decrease in efficacy as the lead migrates. When it can produce paresthesias in the region of pain, spinal cord stimulation is typically successful initially in reducing pain, but over time the paresthesia coverage and pain reduction is often lost as the lead migrates away from its target (North et al. 1991; Andersen 1997; Loeser 2001a).

Lead migration is the most common complication for spinal cord stimulators occurring in up to 45-88% of the cases (North et al. 1991; Andersen 1997; Spincemaille et al. 2000; Sharan et al. 2002). When the lead migrates, the active contact moves farther from the target fibers and loses the ability to generate paresthesias in the target area. SCS systems attempt to address this problem by using leads with multiple contacts so that as the lead travels, the next contact in line can be selected to be the active contact.

Peripheral nerve stimulation may be effective in reducing pain, but it previously required specialized surgeons to place cuff- or paddle-style leads around the nerves in a time consuming procedure.

These methods of implementation have practical limitations that prevent widespread use. External systems are too cumbersome, and implanted spinal cord stimulation systems often have problems of lead migration along the spinal canal, resulting in either the need for frequent reprogramming or clinical failure.

Percutaneous, intramuscular electrical stimulation for the treatment of post-stroke shoulder pain has been studied as an alternative to surface electrical stimulation. A feasibility study (Chae, Yu, and Walker, 2001) and a pilot study (Chae, Yu, and Walker, 2005) showed significant reduction in pain and no significant adverse events when using percutaneous, intramuscular electrical stimulation in shoulder muscles.

This form of percutaneous, intramuscular electrical stimulation can be characterized as "motor point" stimulation of muscle. To relieve pain in the target muscle, the percutaneous lead is placed in the muscle that is experiencing the pain near the point where a motor nerve enters the muscle (i.e., the motor point). In "motor point" stimulation of muscle, the muscle experiencing pain is the same muscle in which the lead is placed. In "motor point" stimulation of muscle, the pain is felt and relieved in the area where the lead is located.

SUMMARY OF THE INVENTION

The invention provides improved systems and methods for placing one or more electrode leads in tissue for providing electrical stimulation to tissue to reduce pain.

One aspect of the invention provides lead placement procedures that may be used for placing a single electrode lead to activate a target nerve and/or nerves and/or nerve bundles (e.g., the brachial plexus, sciatic nerve, and/or femoral nerve, and/or their roots or branches) that carry the pain signals) in a system for the relief of neuropathic pain, such as post-amputation pain, but is not exclusive to this application. For example, if the pinky finger hurts, the systems and methods are well adapted to stimulate the ulnar nerve (which innervates the pinky finger). The procedures optimally allow using only a single lead, although it is to be appreciated that more than one leads) may be used, to activate a greater range of target nerves and/or nerve bundles.

Other features and advantages of the inventions are set forth in the following specification and attached drawings.

The invention provides systems and methods for placing one or more leads in tissue for providing electrical stimulation to tissue to treat pain in a manner unlike prior systems and methods.

The invention provides systems and methods incorporate a discovery that pain felt in a given region of the body can be treated, not by motor point stimulation of muscle in the local region where pain is felt, but by stimulating muscle close to a "nerve of passage" in a region that is superior (i.e., cranial or upstream toward the spinal column) to the region where pain is felt. Neural impulses comprising pain felt in a given muscle or cutaneous region of the body pass through spinal nerves that arise from one or more nerve plexuses. The spinal nerves in a nerve plexus, which comprise trunks that divide by divisions and/or cords into branches, comprise "nerves of passage." It has been discovered that applying stimulation in a muscle near a targeted nerve of passage relieves pain that manifests itself in a region that is inferior (i.e., caudal or downstream from the spinal column) from where stimulation is actually applied.

Phantom (or amputee) pain is one example of the effectiveness of "nerves of passage" stimulation, because the area in which phantom pain is felt does not physically exist. A lead cannot be physically placed in the muscles that hurt, because those muscles were amputated. Still, by applying stimulation in a muscle that has not been amputated near a targeted nerve of passage that, before amputation, natively innervated the amputated muscles, phantom pain can be treated.

Chronic or acute pain in existing, non-amputated muscles can also be treated by "nerves of passage" stimulation. By applying stimulation in an existing muscle near a targeted nerve of passage that caudally innervates the region where chronic or acute pain is manifested, the pain can be treated.

In "nerves of passage" stimulation, a lead can be placed in a muscle that is conveniently located near a nerve trunk that passes by the lead on the way to the painful area. On "nerves of passage" stimulation, the lead is placed in a muscle that is not the target (painful) muscle, but rather a muscle that is upstream from the painful region, because the proximal muscle presents a convenient and useful location to place the lead.

The systems and methods make possible the treatment of chronic or acute pain in which muscle contraction cannot be evoked (e.g. in the case of amputation pain in which the target area has been amputated is no longer physically present), or other cases of nerve damage either due to a degenerative diseases or condition such as diabetes of impaired vascular function (in which the nerves are slowly degenerating, progressing from the periphery), or due to trauma. The systems and methods make possible the placement stimulation leads in regions distant from the motor point or region of pain, e.g., where easier access or more reliable access or a clinician-preferred access be accomplished; or in situations where the motor nerve point is not available, damaged, traumatized, or otherwise not desirable; or in situations where it is desirable to stimulate more than one motor point with a single lead; or for cosmetic reasons; or to shorten the distance between the lead and its connection with a pulse generator; or to avoid tunneling over a large area.

BRIEF DESCRIPTION OF THE DRAWINGS

FIG. 15A is a schematic anatomic view of a human spine, showing the various regions and the vertebrae comprising the regions.

FIGS. 15B and 15C are schematic anatomic views of the dermatome boundaries of a human.

FIG. 20 is an anatomic view of the spinal nerves of the cervical plexus.

FIG. 21 is an anatomic view of the spinal nerves of the solar plexus.

FIGS. 32A, 32B, and 32C are schematic sectional anatomic views of a system for applying nerve of passage stimulation along a sciatic/tibial nerve.

DESCRIPTION OF THE PREFERRED EMBODIMENT

Figure 1:
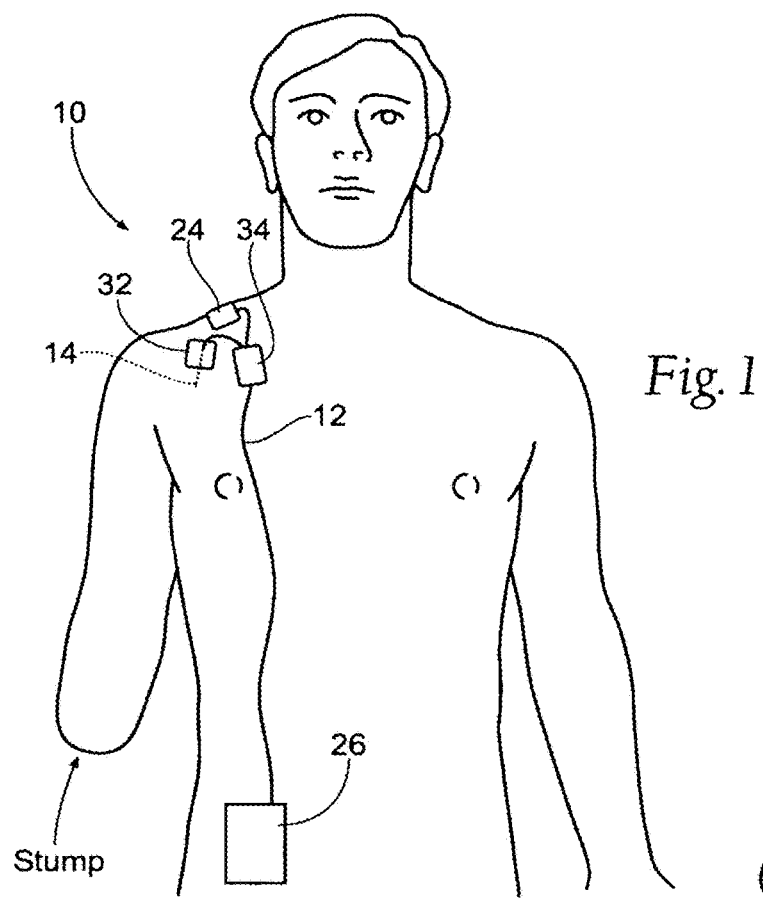
FIG. 1 is an anatomical view of a patient utilizing one embodiment of the present invention, including a percutaneous electrode lead coupled to an external pulse generator.

Although the disclosure hereof is detailed and exact to enable those skilled in the art to practice the invention, the physical embodiments herein disclosed merely exemplify the invention which may be embodied in other specific structures. While the desired embodiment has been described, the details may be changed without departing from the invention.

Any elements described herein as singular can be pluralized (i.e., anything described as "one" can be more than one). Any species element of a genus element can have the characteristics or elements of any other species element of that genus. The described configurations, elements or complete assemblies and methods and their elements for carrying out the invention, and variations of aspects of the invention can be combined and modified with, each other in any combination.

The various aspects of the invention will be described in connection with the placement of one or more leads 12 having one or more electrodes 14, in tissue, e.g., on, in, or near nerves and/or muscles, for improved recruitment of targeted nerves or muscles for prosthetic or therapeutic purposes, such as for the treatment of post-amputation pain. That is because the features and advantages that arise due to the invention are well suited to this purpose. Still, it should be appreciated that the various aspects of the invention can be applied to achieve other objectives as well.

I. Reduction of Post-Amputation Pain

The present novel invention provides systems and methods for the reduction of pain. Most amputees have two types of pain: residual limb (stump) pain and phantom pain. The systems and methods of the present invention are adapted to reduce either and/or both types of pain by stimulating target nerves, generally on the same side of the body as the amputation, i.e., the nerves that innervate the regions of pain. It is to be appreciated that amputation can include any or all portions of a limb, including arms and legs in both humans and animals.

The present novel invention provides systems and methods that place percutaneous electrode lead(s) 12 appropriately in patients with amputations to electrically activate a target nerve and/or nerves and/or nerve bundles (e.g., the brachial plexus, sciatic nerve, and/or femoral nerve, and/or their roots or branches) that carry the pain signal(s). For example, if the pinky finger hurts, the systems and methods are well adapted to stimulate the ulnar nerve (which innervates the pinky finger). If electrical stimulation activates the target nerve sufficiently at the correct intensity, then the patient will feel a comfortable tingling sensation called a paresthesia in the same region as their pain. It is to be appreciated that the sensation could be described with other words such as buzzing, thumping, etc. Just as the patient can have pain in the stump and/or the phantom limb, electrical stimulation can evoke paresthesias that the patient also feels in the stump and/or phantom limb. Evoking paresthesias in the regions of pain confirms correct lead placement and indicates stimulus intensity is sufficient to reduce pain.

Figure 2:
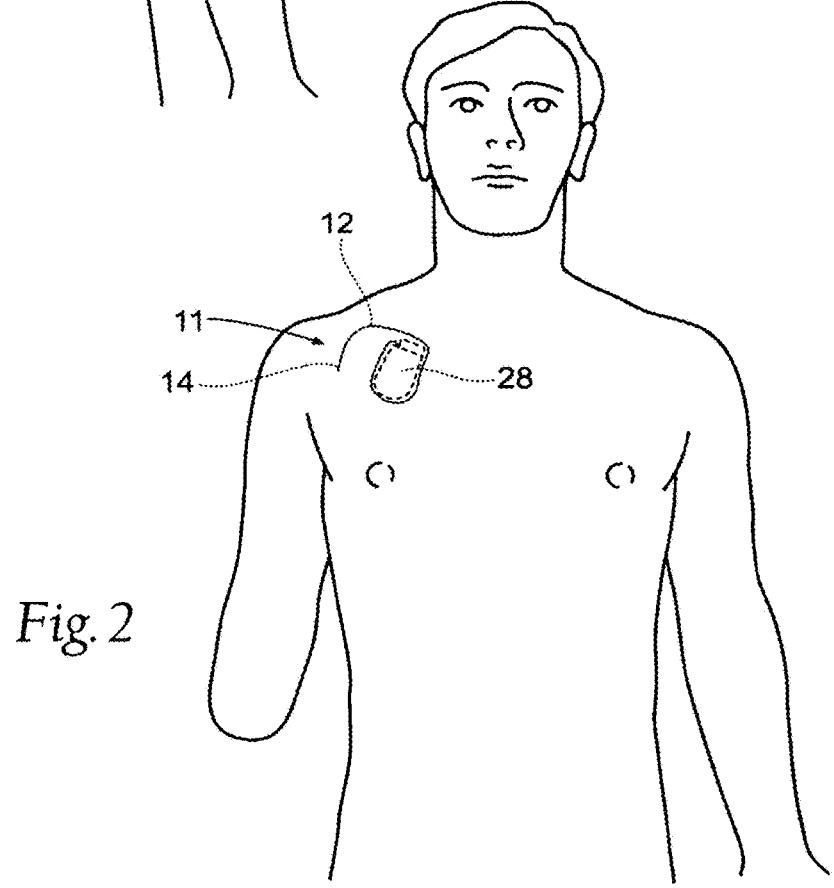
FIG. 2 is an anatomical view of a patient utilizing another embodiment of the present invention, including an implanted electrode lead coupled to an implanted pulse generator.

The ability to insert the lead 12 percutaneously near a target peripheral nerve simplifies the approach to a quick (e.g., 5, or 10, or 20 minute) procedure, such as an outpatient procedure that can be performed in a standard community-based clinic, allowing widespread use and providing a minimally-invasive screening test to determine if patients will benefit from the systems and methods of the present invention, including a percutaneous system 10 and/or a fully implanted system 11 (see FIGS. 1 and 2).

The systems and methods of the present invention are well suited to place a percutaneous lead 12 on, in, or near the brachial plexus with a quick procedure to generate electrically a comfortable (tingling) sensation of paresthesia in the regions of stump and phantom pain and reduce the patients' pain.

In a percutaneous system 10, the lead 12 may be percutaneously placed near the brachial plexus and exit at the skin puncture site 16 and coupled to an external pulse generator 26. The percutaneously placed lead 12 and external pulse generator 26 may provide a screening test function to confirm paresthesia coverage and/or pain relief of the painful areas. If the screening test is successful, the patient may proceed to a home-trial (e.g., a day, week, month, year) to determine if pain relief can be sustained in the home environment. If either the screening test or home trial is unsuccessful, the lead 12 may be quickly and easily removed. It is to be appreciated that a home-trial is not a requirement for either the percutaneous system or a fully implanted system.

However, if the screening test and/or home-trial are successful, the patient's percutaneous system may be converted into a fully implanted system 11 by replacing the external pulse generator 26 with an implantable pulse generator 28 that is implanted in a convenient area (e.g., the subclavicular area), and coupling a new sterile lead 12, or a sterile lead extension, to the implantable pule generator 28.

Inserting the lead 12 percutaneously allows the lead 12 to be placed quickly and easily, and placing the lead 12 in a peripheral location, where it is less likely to be dislodged, addresses the lead migration problems of spinal cord stimulation that result in decreased paresthesia coverage, decreased pain relief, and the need for frequent patient visits for reprogramming.

In the exemplary embodiment of the present invention, placing the percutaneous lead 12 in adipose tissue of the infraclavicular and subcoracoid space near the brachial plexus (to be described in greater detail below), may minimize complications related to lead movement. Perineural catheters connected to infusion pumps have been placed in similar locations for use by ambulatory patients in their home environment and have a low rate of catheter dislocations and complications (Wilson et al 1998; Ekatodramis and Borgeat 2000; Ilfeld et al. 2002).

In the percutaneous system 10, an electrode lead 12, such as a coiled fine wire electrode lead may be used because it is minimally-invasive and previous studies suggest it will perform well in this location and tissue type during use.

In the fully implanted system 11, the same or different electrode lead 12 may be used, such as a slightly larger electrode lead that may be sized and configured to withstand greater mechanical forces and resist migration during long-term use. A larger electrode lead 12 may be sized and configured to withstand forces in excess of those anticipated near the brachial plexus, and other similarly flexible regions of the body.

II. Implanting the Electrode Lead

A. The Anatomic Landmarks

Figure 3A:
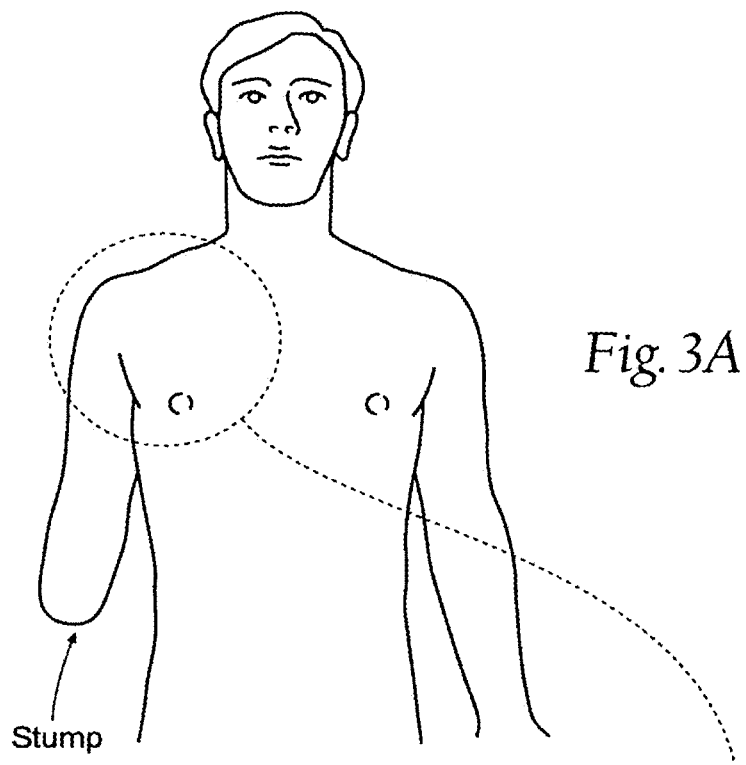
FIGS. 3A and 3B are anatomical views of a patient's shoulder showing the anatomical landmarks useful to guide the placement of a needle electrode as a component and/or step of the present invention.
Figure 3B:
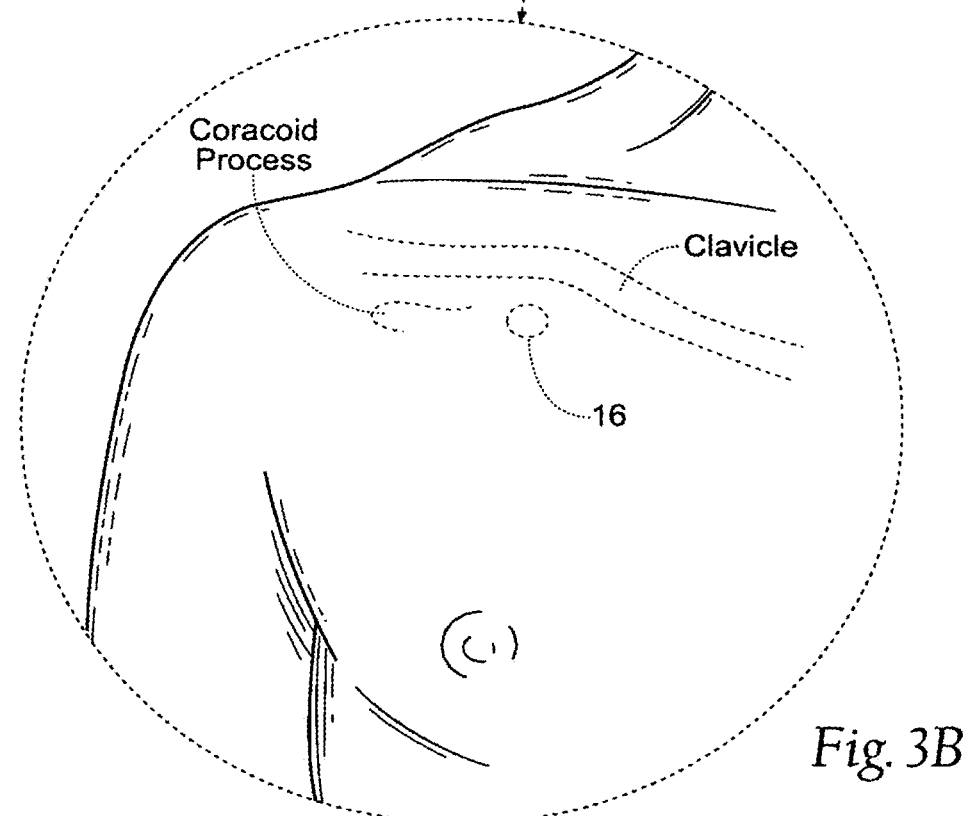

As already described, certain components of the systems and methods of the present invention are well adapted to be implanted in a particular location near the patients shoulder, where it has been discovered that effective stimulation of the nerves of the brachial plexus can be achieved with a single electrode lead 12 to reduce pain. As can be seen in FIGS. 3A and 3B, the main anatomic landmarks guiding the unique placement of these components are the clavicle and the coracoid process.

Figure 4:
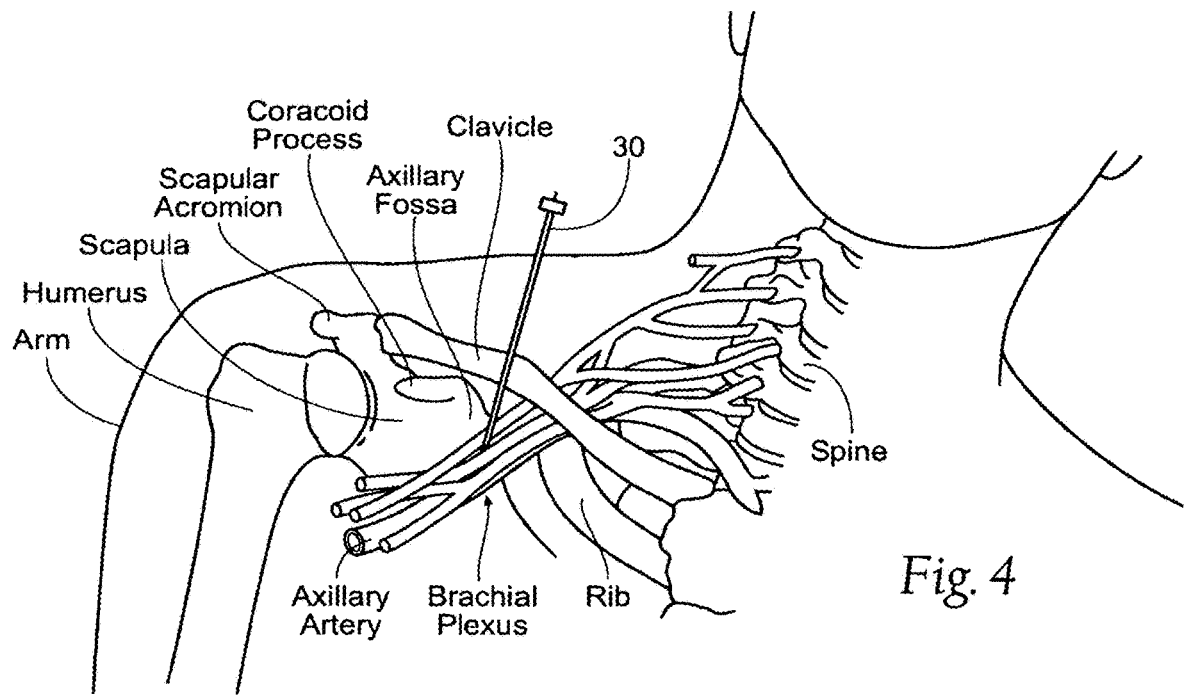
FIG. 4 is an anatomical view of the shoulder as shown in FIG. 3B, showing infraclavicular and subcoracoid neuroanatomy with a needle introducer depicting a direction of lead insertion toward the brachial plexus.

FIG. 4 shows the clavicle as a doubly curved short bone that connects the arm (upper limb) to the body (trunk), located directly above the first rib. It acts as a shunt to keep the scapula in position so the arm can hang freely. The coracoid process is a small finger-like structure on the upper lateral corner of the scapula. Pointing laterally forward, it, together with the acromion, serves to stabilize the shoulder joint. It is palpable in the deltopectoral groove between the deltoid and pectoralis major muscles.

Figure 5:
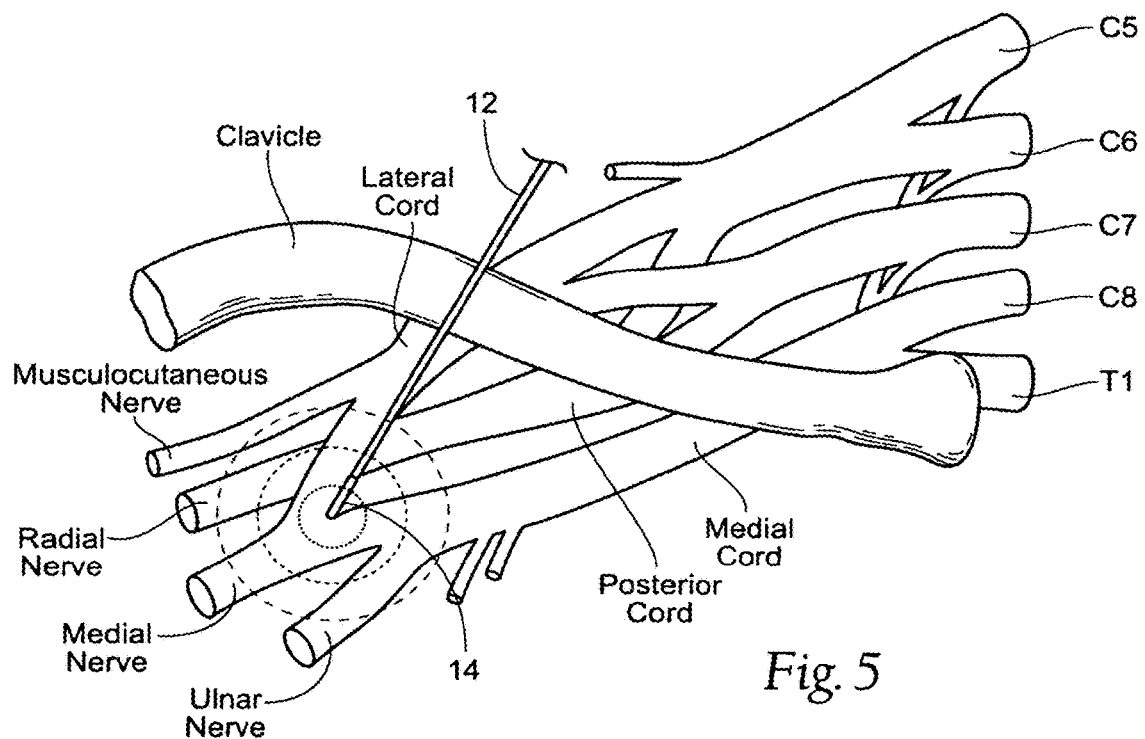
FIG. 5 is an anatomical view similar to FIG. 4, except showing greater detail of the brachial plexus and the lead insertion, and showing an anticipated region of activation.

Guided by these landmarks, the brachial plexus can be identified. Referring to FIGS. 4 and 5, the brachial plexus comprises an arrangement of nerve fibers, running from the spine, formed by the ventral rami of the lower cervical and upper thoracic nerve roots, specifically from above the fifth cervical vertebra to underneath the first thoracic vertebra (C5-T1). It proceeds through the neck, under the clavicle and generally anterior to the scapula, through the armpit region and into the aim. The brachial plexus is generally responsible for cutaneous and muscular innervation of the entire upper limb, with only two exceptions; the trapezius muscle is innervated by the spinal accessory nerve and an area of skin near the armpit is innervated by the intercostobrachialis nerve.

Figure 6:
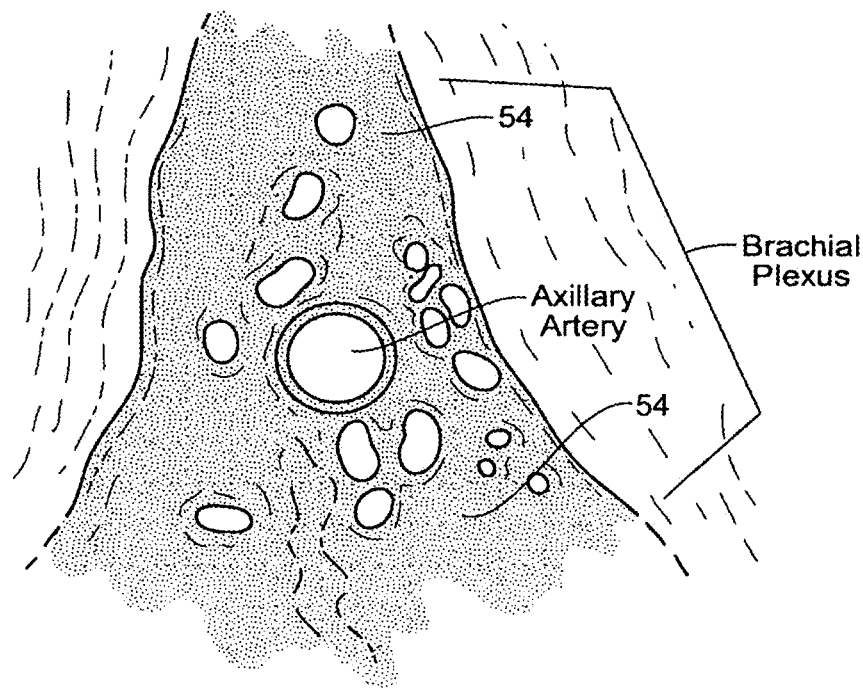
FIG. 6 is an anatomical cross-sectional view (perpendicular to the axis of the lead insertion) of the brachial plexus and surrounding tissue.

FIG. 6 is a cross-sectional view (perpendicular to the axis of the lead insertion) of the brachial plexus and surrounding tissue (Moayeri et al. 2008). As can be seen in FIG. 6, the brachial plexus is surrounded by a large amount of adipose tissue 54 in the infraclavicular and subcoracoid regions, where the electrode lead 12 will be placed, and is well suited for use in adipose tissue. In the infraclavicular and subcoracoid sections of cadavers studied, the brachial plexus was surrounded by about $6.90 \pm 1.82 \, cm^2$ to about $7.06 \pm 1.48 \, cm^2$, which is ample area to place the electrode lead 12.

B. Implantation Methodology

Representative lead insertion techniques will now be described to place an electrode lead 12 in a desired location in adipose tissue 54 at or near the brachial plexus. It is this desired placement that makes possible the stimulation of the brachial plexus with a single lead 12 to provide pain relief.

Figure 7:
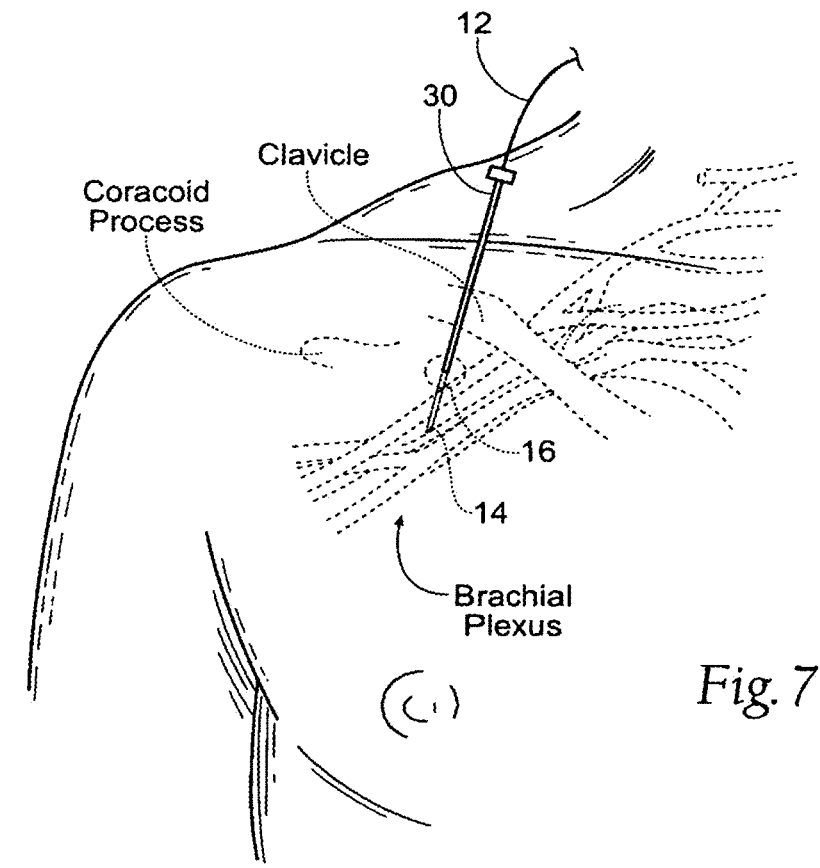
FIG. 7 is an anatomical view of the shoulder as shown in FIG. 3B, showing the percutaneous lead inserted through the skin in the target area in the shoulder via an introducer needle.
Figure 8:
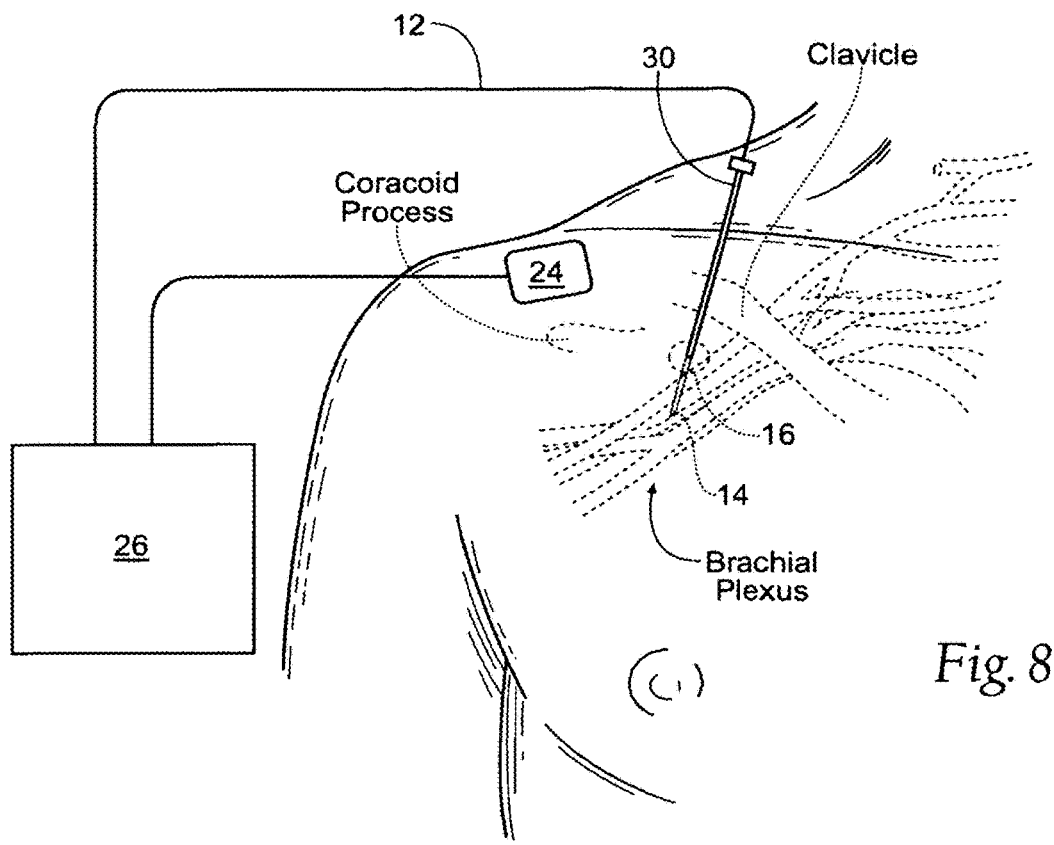
FIG. 8 is an anatomical view of the shoulder as shown in FIG. 7, showing the percutaneous lead coupled to the external pulse generator and the return electrode.

FIGS. 7 and 8 show representative embodiments of the steps that representative instructions for use 58 can incorporate or direct for the placement of an electrode lead 12 in a targeted tissue region for the relief of pain, such as post-amputation pain. The instructions may include a series of steps that can be followed to carry out portion or portions of the procedure. These steps may include, but are not limited to:

1) Place the patient in a supine position with head turned away from the lead insertion site 16 and forearm laid to rest in a neutral position beside the body.

2) Prepare the lead insertion site with antiseptic and local subcutaneous anesthetic (e.g., 2% lidocaine).

3) Locate the site of skin puncture 16 with landmarks as necessary, such as those previously described, e.g., approximately 2 cm medial and caudal to the coracoid process.

4) Insert a sterile percutaneous electrode lead 12 at a predetermined angle based on landmarks used, e.g., approximately 45 degrees towards the top of the axillary fossa in relation to the axillary artery. The lead 12 may be preloaded in the introducer needle 30 (see FIG. 7).

5) Place a surface stimulation return electrode 24 in proximity of the area in which the percutaneous lead 12 has been placed. Test stimulation will be applied to the lead 12, with the surface electrode 24 providing a return path. The surface electrode 24 may be placed adjacent to the lead. Its position is not critical to the therapy and it can be moved throughout the therapy to reduce the risk of skin irritation.

6) Couple the lead 12 to the external pulse generator 26 and to the return electrode 24 (see FIG. 8). Set the desired stimulation parameters. Test stimulation may be delivered using a current-regulated pulse generator, for example. The external pulse generator 26 may be programmed to 4 mA, 100 μs, 100 Hz, and an on-off duty cycle of 0.25 sec., as a non-limiting example.

7) Advance the introducer slowly until the subject reports the first evoked sensation in the stump or phantom upper limb (e.g., hand). Progressively reduce the stimulus amplitude and advance the introducer more slowly until the sensation can be evoked in the phantom upper limb at a predetermined stimulus amplitude (e.g., 1 mA). Stop the advancement of the introducer, and increase the stimulus amplitude in small increments (e.g., 0.1 mA) until the stimulation-evoked tingling sensation (paresthesia) expands to overlay the entire region of pain in the subject's stump and phantom limb.

It is expected to locate the brachial plexus after inserting the introducer approximately 4 cm from the site of skin puncture 16. At this depth, it is expected that a low stimulus intensity may evoke comfortable sensations (paresthesia) without generating muscle contraction (Nashold and Goldner 1975; Picaza et al. 1975; Nashold et al. 1982).

8) Withdraw the introducer 30, leaving the percutaneous lead 12 in proximity to the brachial plexus.

9) Cover the percutaneous exit site and lead 12 with a bandage 32. A bandage 34 may also be used to secure the external portion of the lead 12 (or an extension cable used to couple the lead 12 to the external pulse generator) to the skin (see FIG. 1). It is expected the length of time to place the lead 12 to be less than 10 minutes, although the process may be shorter or longer.

10) Vary the stimulus amplitude in small steps (e.g., 0.1-0.5 mA) to determine the thresholds at which stimulation evokes first sensation ($T_{SEN}$), sensation (paresthesia) superimposed on the region of pain ($T_{SUP}$), muscle twitch ($T_{MUS}$) of the triceps brachii (innervated by the radial nerve branch of the brachial plexus), and maximum comfortable sensation ($T_{MAX}$). Query the subject at each stimulus amplitude to determine sensation level, and visually monitor muscle response. Record the results.

11) It is possible that stimulation intensity may need to be increased slightly during the process due to causes such as habituation or the subject becoming accustomed to sensation, but the need for increased intensity is unlikely and usually only occurs after several days to weeks to months as the tissue encapsulates and the subject accommodates to stimulation (Nashold 1975; Krainick and Thoden 1981; Goldman et al. 2008). It is to be appreciated that the need for increased intensity could happen at any time, even years out, which would likely be due to either lead migration or habituation, but may also be due reasons ranging from nerve damage to plasticity/reorganization in the central nervous system.

12) If paresthesias cannot be evoked with the initial lead placement, redirect the introducer 30 either caudal or cephalad, but avoid the lung by never directing the needle introducer 30 medially.

13) If sensations still cannot be evoked in a given subject, then the muscle twitch response of the triceps brachii may be used to guide lead placement and then increase stimulus intensity until sufficient paresthesias are elicited in the stump and phantom limb. Minimal muscle contraction may be acceptable if it is well tolerated by the amputee patient in exchange for significant pain relief and if it does not lead to additional discomfort or fatigue (Long 1973).

14) If stimulation evokes muscle contraction at a lower stimulus threshold than paresthesia (e.g. if $T_{MUS} \leq T_{SUP}$) and contraction leads to discomfort, then a lower stimulus frequency (e.g., 12 Hz) may be used because low frequencies (e.g., 4-20 Hz) have been shown to minimize discomfort due to muscle contraction and provide >50% relief of shoulder pain in stroke patients while still inhibiting transmission of pain signals in the central nervous system in animals (Chung et al. 1984; Yu et al. 2001, 2004; Chae et al, 2005). If continued muscle contraction leads to pain due to fatigue, change the duty cycle, using parameters shown to reduce muscle fatigue and related discomfort in the upper extremity (e.g. 5 s ramp up, 10 s on, 5 s ramp down, 10 s off) (Yu et al. 2004; Chae et al. 2005).

15) If stimulation fails to elicit paresthesia in all areas of pain, then a second percutaneous lead 12' (not shown) may need to be placed to stimulate the nerves that are not activated by the first lead 12. If paresthesia coverage is incomplete, it may likely be due to insufficient activation of the musculocutaneous nerve because it has the most proximal branch point relative to the other nerves and is the most likely to be missed during single-injection nerve blocks of the brachial plexus. To place a lead near the musculocutaneous nerve, use the modified coracoid approach (a double-stimulation technique) that targets the musculocutaneous nerve in addition to the main trunk of the brachial plexus, as described above (Desroches 2003; Minville et al. 2005).

16) If stimulation is successful, i.e., if the screening test and/or home-trial are successful, the patient's percutaneous system 10 (see FIG. 1) may be converted into a fully implanted system 11 by replacing the external pulse generator 26 with an implantable pulse generator 28 that is implanted in a convenient area (e.g., the subclavicular area). In one embodiment, the electrode lead 12 used in the screening test and/or home-trial may be totally removed and discarded, and a new completely implantable lead may be tunneled subcutaneously and coupled to the implantable pulse generator. In an alternative embodiment, a two part lead may be incorporated in the screening test and/or home-trial where the implantable part is completely under the skin and connected to a percutaneous connector (i.e., extension) that can be discarded after removal. The implantable part may then be tunneled and coupled to the implantable pulse generator, or a new sterile extension may be used to couple the lead to the implantable pulse generator.

III. Electrode Lead Configurations

It is to be appreciated that the configuration of one or more leads 12 and electrodes 14, and the manner in which they are implanted can vary. Stimulation may be applied through an electrode lead 12, such as a fine wire electrode, paddle electrode, intramuscular electrode, or general-purpose electrode, inserted via a needle introducer or surgically implanted in proximity of the target site. Once proper placement is confirmed, the needle may be withdrawn, leaving the electrode in place. Stimulation may also be applied through a penetrating electrode, such as an electrode array comprised of any number (i.e., one or more) of needle-like electrodes that are inserted into the target site. In both cases, the lead may placed using a needle-like introducer, allowing the lead/electrode placement to be minimally invasive.

The electrode 14 may be electrically insulated everywhere except at one (monopolar), or two (bipolar), or three (tripolar), for example, conduction locations near its distal tip. Each of the conduction locations may be connected to one or more conductors that run the length of the electrode and lead 12, proving electrical continuity from the conduction location through the lead 12 to the stimulator 26 or 28.

The electrode lead 12 is desirably provided in a sterile package, and may be pre-loaded in the introducer needle 30. The lead 12 desirably possess mechanical properties in terms of flexibility and fatigue life that provide an operating life free of mechanical and/or electrical failure, taking into account the dynamics of the surrounding tissue, stretching, bending, pushing, pulling, crushing, etc.). The material of the electrode desirably discourages the in-growth of connective tissue along its length, so as not to inhibit its withdrawal at the end of its use. However, it may be desirable to encourage the in-growth of connective tissue at the distal tip of the electrode, to enhance its anchoring in tissue.

Figure 9:
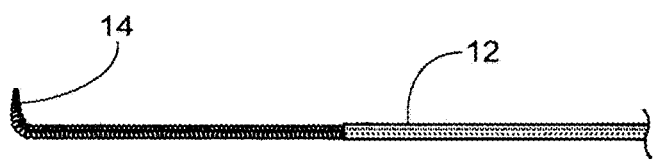
FIG. 9 is a view of a possible electrode lead for use with the systems and methods of the present invention.

One embodiment of the lead 12 shown in FIG. 9 may comprise a minimally invasive coiled fine wire lead 12 and electrode 14. The electrode 14 may also include, at its distal tip, an anchoring element 48. In the illustrated embodiment, the anchoring element 48 takes the form of a simple barb or bend. The anchoring element 48 is sized and configured so that, when in contact with tissue, it takes purchase in tissue, to resist dislodgement or migration of the electrode out of the correct location in the surrounding tissue. Desirably, the anchoring element 48 is prevented from fully engaging body tissue until after the electrode 14 has been deployed. The electrode may not be deployed until after it has been correctly located during the implantation (lead placement) process, as previously described.

Figure 10:
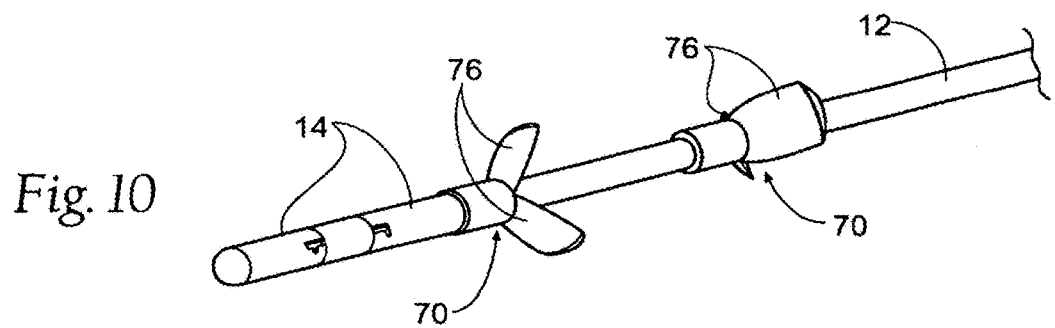
FIGS. 10 and 11 are perspective views of another possible electrode lead for use with the systems and methods of the present invention, the lead including anchoring members.
Figure 11:
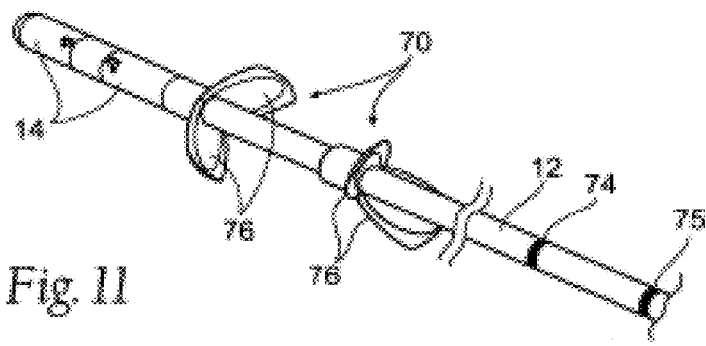

An alternative embodiment of an electrode lead 12 shown in FIGS. 10 and 11, may also include, at or near its distal tip or region, one or more anchoring element(s) 70. In the illustrated embodiment, the anchoring element 70 takes the form of an array of shovel-like paddles or scallops 76 proximal to the proximal-most electrode 14 (although a paddle 76 or paddles could also be proximal to the distal most electrode 14, or could also be distal to the distal most electrode 14). The paddles 76 as shown are sized and configured so they will not cut or score the surrounding tissue. The anchoring element 70 is sized and configured so that, when in contact with tissue, it takes purchase in tissue, to resist dislodgement or migration of the electrode out of the correct location in the surrounding tissue (e.g., soft adipose tissue 54). Desirably, the anchoring element 70 is prevented from fully engaging body tissue until after the electrode 14 has been deployed. The electrode is not deployed until after it has been correctly located during the implantation (lead placement) process, as previously described. In addition, the lead 12 may include one or more ink markings 74, 75 to aid the physician in its proper placement.

Alternatively, or in combination, stimulation may be applied through any type of nerve cuff (spiral, helical, cylindrical, book, flat interface nerve electrode (FINE), slowly closing FINE, etc.) that is surgically placed within muscle at the target site.

In all cases, the lead may exit through the skin and connect with one or more external stimulators 26, or the lead(s) may be routed subcutaneously to one or more implanted pulse generators 28, or they may be connected as needed to internal and external coils for RF (Radio Frequency) wireless telemetry communications or an inductively coupled telemetry to control the implanted pulse generator. The implanted pulse generator 28 may be located some distance (remote) from the electrode 14, or an implanted pulse generator may be integrated with an electrode(s), eliminating the need to route the lead subcutaneously to the implanted pulse generator.

Control of the stimulator and stimulation parameters may be provided by one or more external controllers. In the case of an external stimulator, the controller may be integrated with the external stimulator. The implanted pulse generator external controller (i.e., clinical programmer) may be a remote unit that uses RF (Radio Frequency) wireless telemetry communications (rather than an inductively coupled telemetry) to control the implanted pulse generator. The external or implantable pulse generator may use passive charge recovery to generate the stimulation waveform, regulated voltage (e.g., 10 mV to 20 V), and/or regulated current (e.g., about 10 µA to about 50 mA). Passive charge recovery is one method of generating a biphasic, charge-balanced pulse as desired for tissue stimulation without severe side effects due to a DC component of the current.

The neurostimulation pulse may by monophasic, biphasic, and/or multi-phasic. In the case of the biphasic or multi-phasic pulse, the pulse may be symmetrical or asymmetrical. Its shape may be rectangular or exponential or a combination of rectangular and exponential waveforms. The pulse width of each phase may range between e.g., about 0.1 µsec. to about 1.0 sec., as non-limiting examples.

Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

The stimulating frequency may range from e.g., about 1 Hz to about 300 Hz, and the frequency of stimulation may be constant or varying. In the case of applying stimulation with varying frequencies, the frequencies may vary in a consistent and repeatable pattern or in a random (or pseudo random) fashion or a combination of repeatable and random patterns.

IV. System Kits

Figure 12:
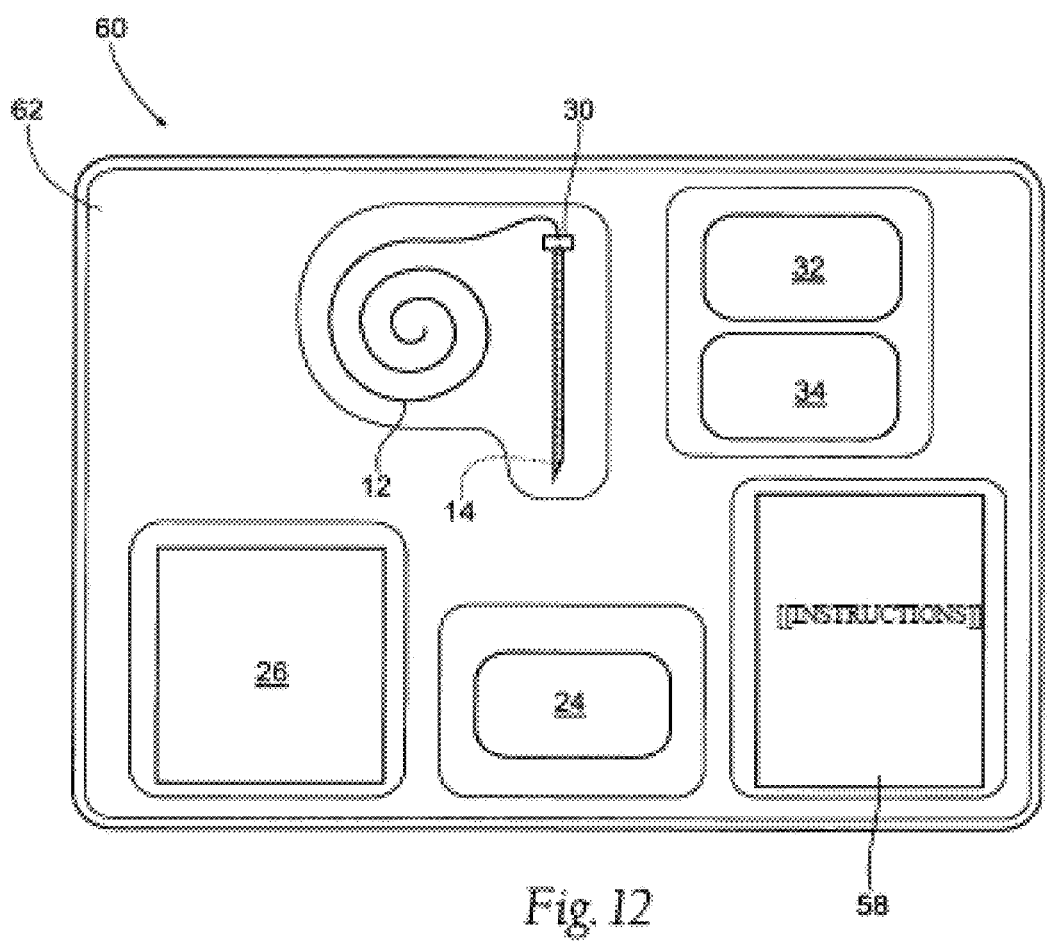
FIG. 12 is a plan view of a kit packaging the systems and methods components for use, along with instructions for use.
Figure 13:
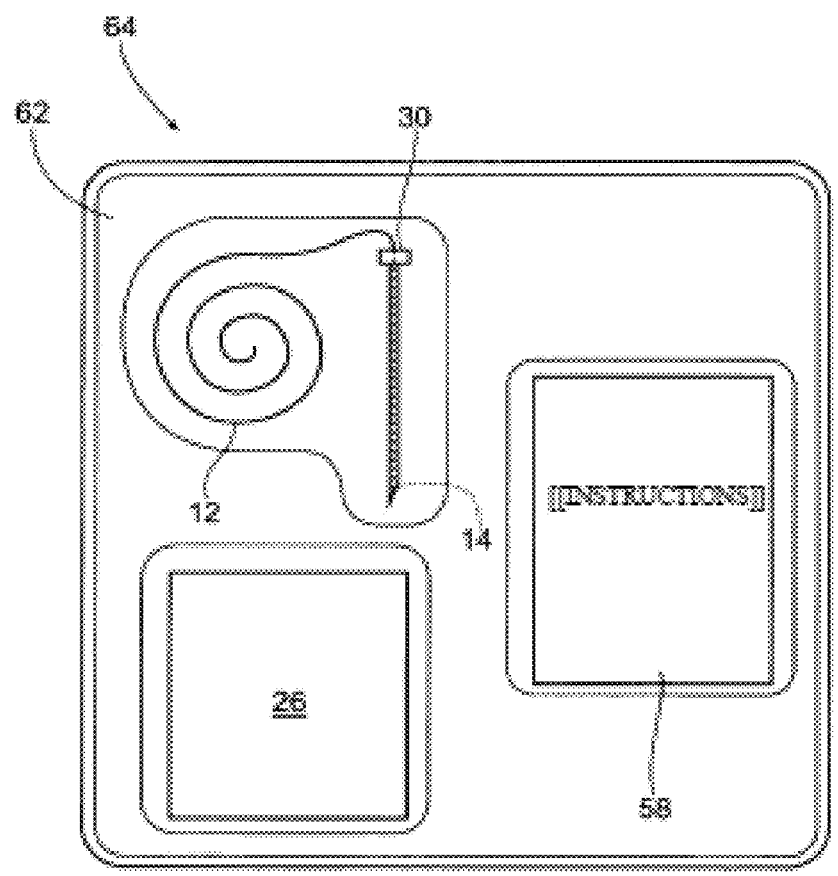
FIG. 13 is a plan view of an additional kit packaging the systems and methods components for use, along with instructions for use.

As FIGS. 12 and 13 show, the various devices and components just described can be consolidated for use in one or more functional kit(s) 60, 64. The kits can take various forms and the arrangement and contents of the kits can vary. In the illustrated embodiments, each kit 60, 64 comprise a sterile, wrapped assembly. Each kit 60, 64 includes an interior tray 62 made, e.g., from die cut cardboard, plastic sheet, or thermo-formed plastic material, which hold the contents. Kits 60, 64 also desirably includes instructions for use 58 for using the contents of the kit to carry out the procedures described above, including the systems and methods incorporating the percutaneous system 10 and/or the implanted system 11.

The instructions 58 can, of course vary. The instructions 58 may be physically present in the kits, but can also be supplied separately. The instructions 58 can be embodied in separate instruction manuals, or in video or audio tapes, CDs, and DVD's. The instructions 58 for use can also be available through an internet web page.

V. The Peripheral Nervous System

Anatomic Overview

Figure 14A:
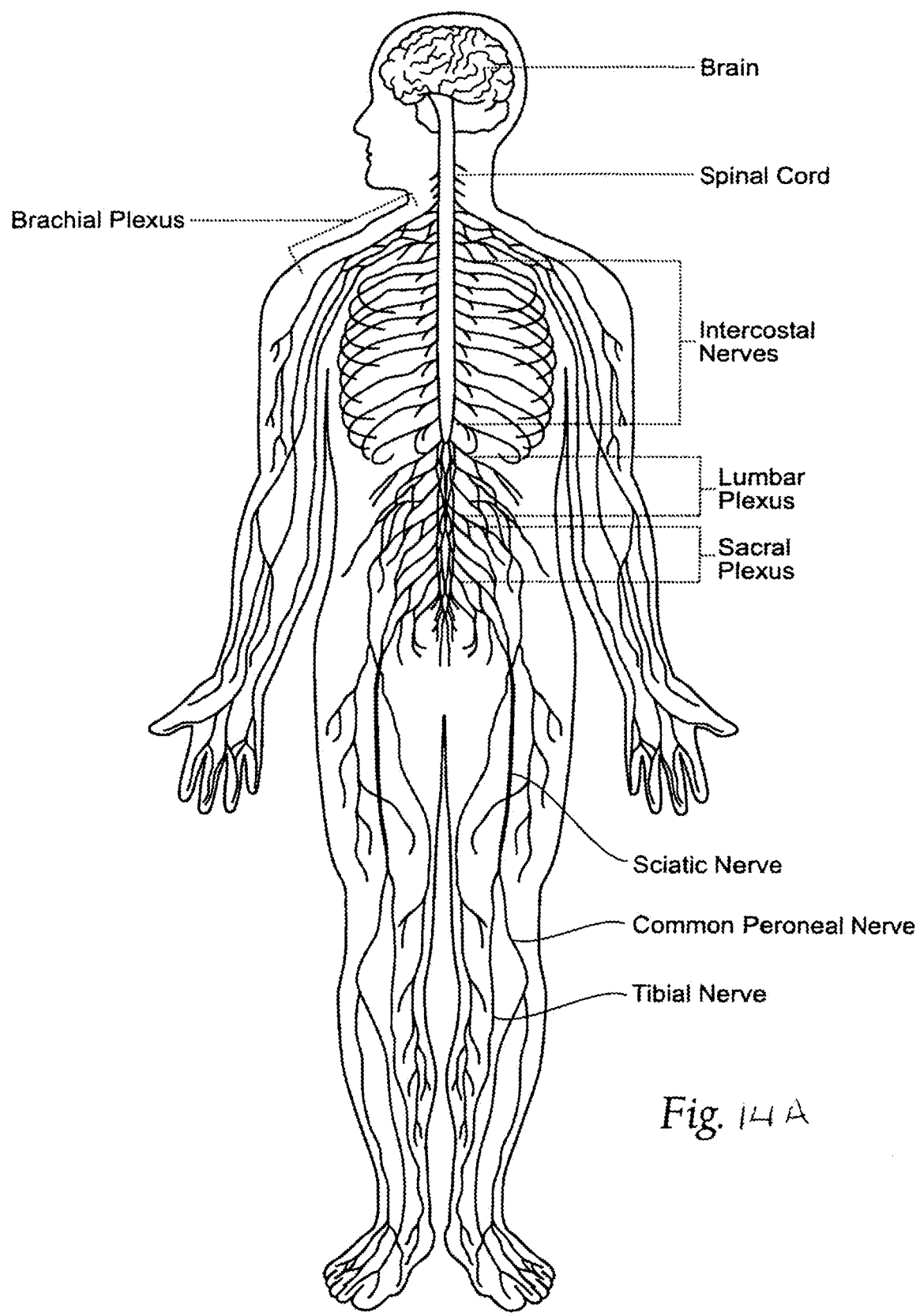
FIGS. 14A and 14B are schematic anatomic views, respectively anterior and lateral, of a human peripheral nervous system.
Figure 14B:
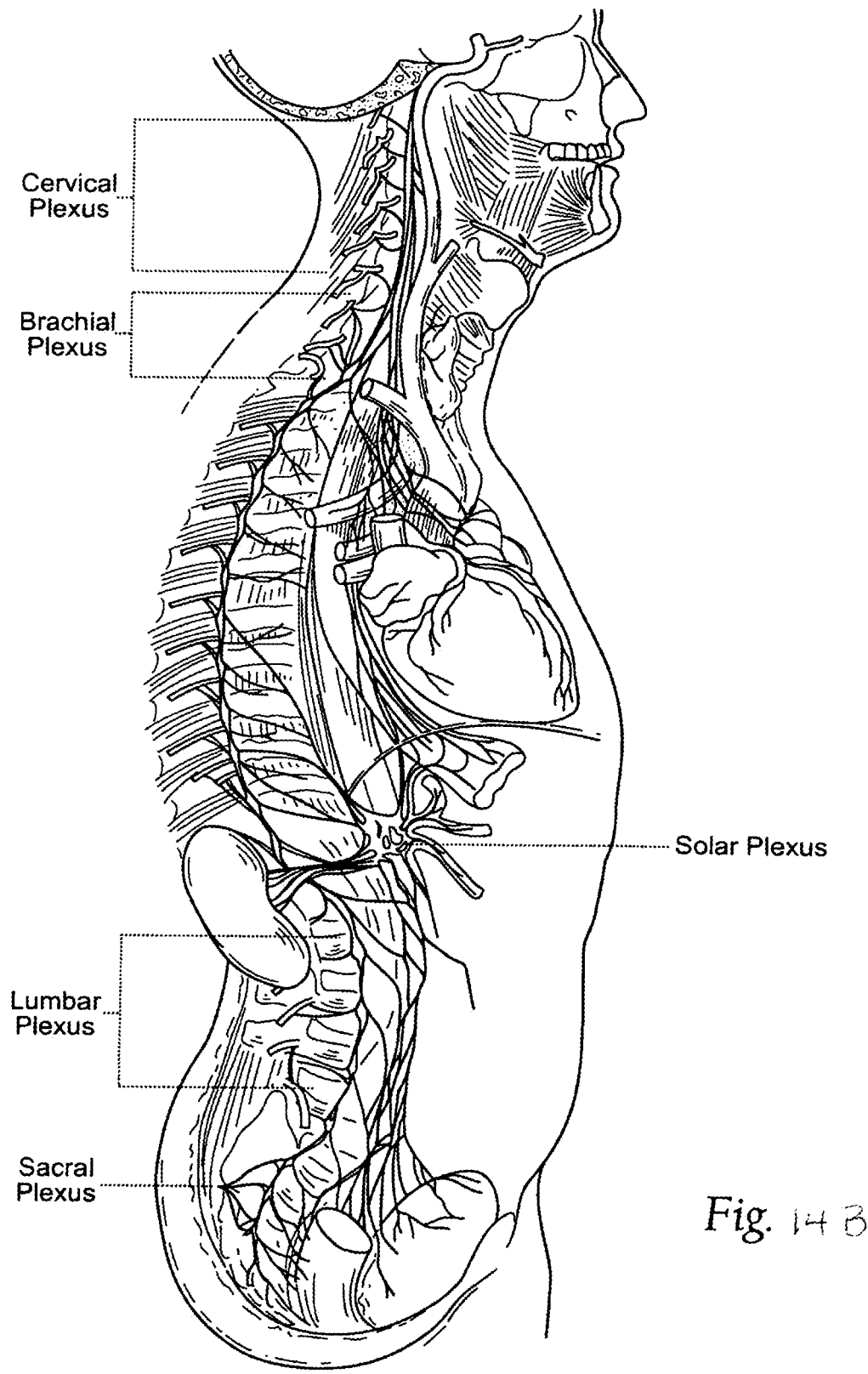

As generally shown in FIGS. 14A and 14B, the peripheral nervous system consists of nerve fibers and cell bodies outside the central nervous system (the brain and the spinal column) that conduct impulses to or away from the central nervous system. The peripheral nervous system is made up of nerves (called spinal nerves) that connect the central nervous system with peripheral structures. The spinal nerves of the peripheral nervous system arise from the spinal column and exit through intervertebral foramina in the vertebral column (spine). The afferent, or sensory, fibers of the peripheral nervous system convey neural impulses to the central nervous system from the sense organs (e.g., the eyes) and from sensory receptors in various parts of the body (e.g., the skin, muscles, etc.). The efferent, or motor, fibers convey neural impulses from the central nervous system to the effector organs (muscles and glands).

The somatic nervous system (SNS) is the part of the peripheral nervous system associated with the voluntary control of body movements through the action of skeletal muscles, and with reception of external stimuli, which helps keep the body in touch with its surroundings (e.g., touch, hearing, and sight). The system includes all the neurons connected with skeletal muscles, skin and sense organs. The somatic nervous system consists of efferent nerves responsible for sending central nervous signals for muscle contraction. A somatic nerve is a nerve of the somatic nervous system.

A. Spinal Nerves

A typical spinal nerve arises from the spinal cord by rootlets which converge to form two nerve roots, the dorsal (sensory) root and the ventral (motor) root. The dorsal and ventral roots unite into a mixed nerve trunk that divides into a smaller dorsal (posterior) primary ramus and a much larger ventral (anterior) primary minus. The posterior primary rami serve a column of muscles on either side of the vertebral column, and a narrow strip of overlying skin. All of the other muscle and skin is supplied by the anterior primary rami.

The nerve roots that supply or turn into peripheral nerves can be generally categorized by the location on the spine where the roots exit the spinal cord, i.e., as generally shown in FIG. 15A, cervical (generally in the head/neck, designated C1 to C8), thoracic (generally in chest/upper back, designated T1 to T12), lumbar (generally in lower back, designated to L1 to L5); and sacral (generally in the pelvis, designated S1 to S5). All peripheral nerves can be traced back (distally toward the spinal column) to one or more of the spinal nerve roots in either the cervical, thoracic, lumbar, or sacral regions of the spine. The neural impulses comprising pain felt in a given muscle or cutaneous region of the body pass through spinal nerves and (usually) one or more nerve plexuses. For this reason, the spinal nerves will sometimes be called in shorthand for the purpose of description "nerves of passage." The spinal nerves begin as roots at the spine, and can form trunks that divide by divisions or cords into branches that innervate skin and muscles.

Spinal nerves have motor fibers and sensory fibers. The motor fibers innervate certain muscles, while the sensory fibers innervate certain areas of skin. A skin area innervated by the sensory fibers of a single nerve root is known as a dermatome. A group of muscles primarily innervated by the motor fibers of a single nerve root is known as a myotome. Although slight variations do exist, dermatome and myotome patterns of distribution are relatively consistent from person to person.

Each muscle in the body is supplied by a particular level or segment of the spinal cord and by its corresponding spinal nerve. The muscle, and its nerve make up a myotome. This is approximately the same for every person and are as follows:

C3, 4 and 5 supply the diaphragm (the large muscle between the chest and the belly that we use to breath).

C5 also supplies the shoulder muscles and the muscle that we use to bend our elbow.

C6 is for bending the wrist back.

C7 is for straightening the elbow.

C8 bends the fingers.

T1 spreads the fingers.

T1-T12 supplies the chest wall & abdominal muscles.

L2 bends the hip.

L3 straightens the knee.

L4 pulls the foot up.

L5 wiggles the toes.

S1 pulls the foot down.

S3, 4 and 5 supply the bladder, bowel, and sex organs and the anal and other pelvic muscles.

Dermatome is a Greek word which literally means "skin cutting". A dermatome is an area of the skin supplied by nerve fibers originating from a single dorsal nerve root. The dermatomes are named according to the spinal nerve which supplies them. The dermatomes form into bands around the trunk (see FIGS. 15B and 15C), but in the limbs their organization can be more complex as a result of the dermatomes being "pulled out" as the limb buds form and develop into the limbs during embryological development.

In the diagrams or maps shown in FIGS. 15B and 15C, the boundaries of dermatomes are usually sharply defined. However, in life there is considerable overlap of innervation between adjacent dermatomes. Thus, if there is a loss of afferent nerve function by one spinal nerve sensation from the region of skin which it supplies is not usually completely lost as overlap from adjacent spinal nerves occurs; however, there will be a reduction in sensitivity.

B. Intercostal Nerves

Figure 16:
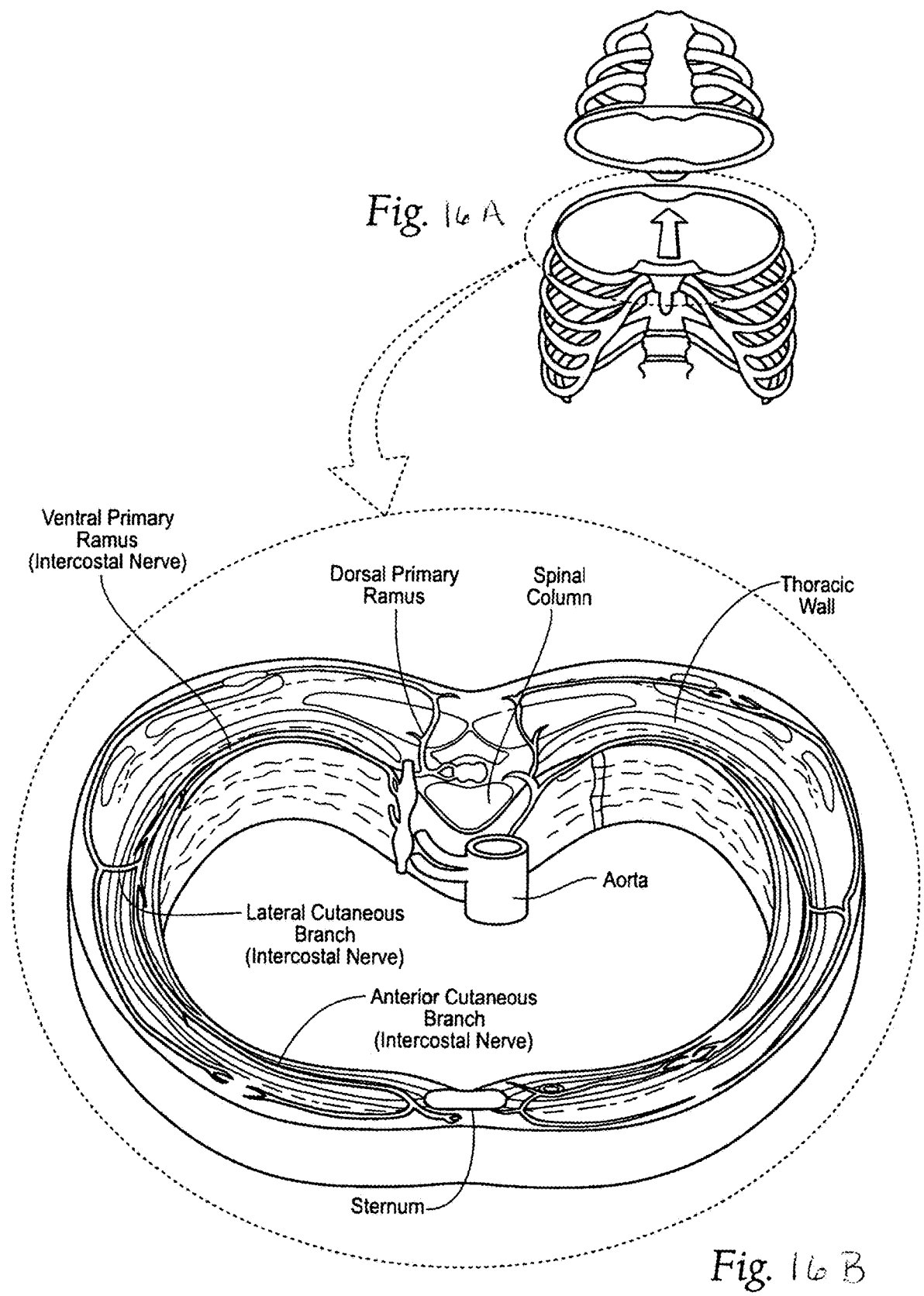
FIGS. 16A, 16B, and 16C are anatomic views of the intercostal spinal nerves of a human.
Figure 16:
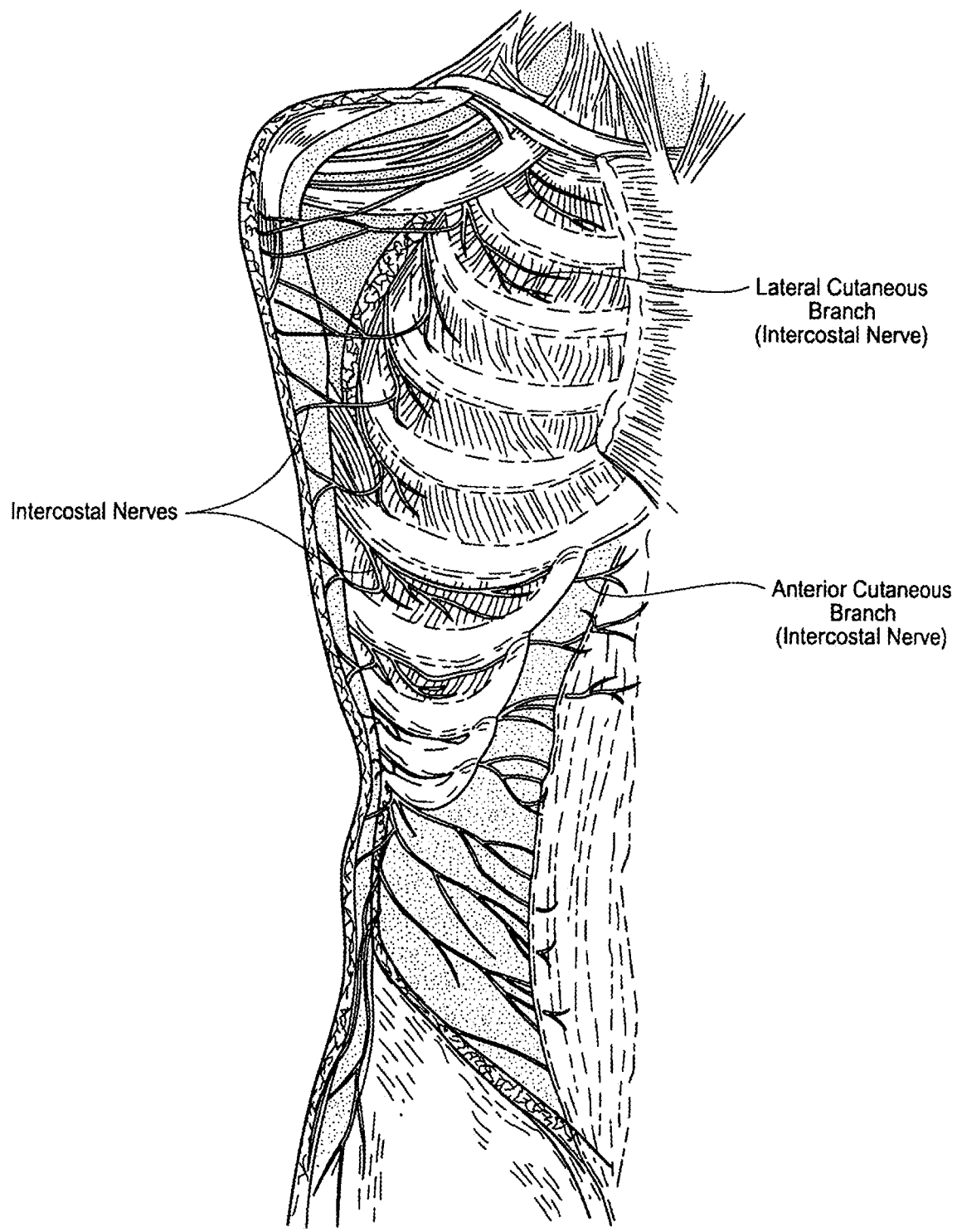

The intercostal nerves (see FIGS. 16A, 16B, and 16C) are the anterior divisions of the thoracic spinal nerves from the thoracic vertebrae T1 to T11. The intercostal nerves are distributed chiefly to the thoracic pleura and abdominal peritoneum and differ from the anterior divisions of the other spinal nerves in that each pursues an independent course without plexus formation.

The first two nerves supply fibers to the upper limb in addition to their thoracic branches; the next four are limited in their distribution to the parietes of the thorax; the lower five supply the parietes of the thorax and abdomen. The 7th intercostal nerve terminates at the xyphoid process, at the lower end of the sternum. The 10th intercostal nerve terminates at the umbilicus. The twelfth (subcostal) thoracic is distributed to the abdominal wall and groin.

Branches of a typical intercostal nerve include the ventral primary ramus; lateral cutaneous branches that pass beyond the angles of the rubs and innervate the internal and external intercostal muscles approximately halfway around the thorax; and the anterior cutaneous branches that supply the skin on the anterior aspect of the thorax and abdomen.

C. Spinal Nerve Plexuses

A nerve plexus is a network of intersecting anterior primary rami. The sets of anterior primary rami form nerve trunks that ultimately further divide through divisions and then into cords and then into nerve branches serving the same area of the body. The nerve branches are mixed, i.e., they carry both motor and sensory fibers. The branches innervate the skin, muscle, or other structures. One example of the entry of a terminal motor nerve branch into muscle is called a motor point.

As shown in FIGS. 14A and 14B, there are several nerve plexuses in the body, including (i) the brachial plexus, which serves the chest, shoulders, arms and hands; (ii) the lumbar plexus, which serves the back, abdomen, groin, thighs, knees, and calves; (iii) the sacral plexus, which serves the buttocks, thighs, calves, and feet; (iv) the cervical plexus, which serves the head, neck and shoulders; and (vi) the solar plexus, which serves internal organs. The following describes, from an anatomic perspective, the spinal nerves of passage passing through the various plexuses, and the muscle and/or skin regions they innervate and where pain can be felt.

1. The Brachial Plexus

Figure 17A:
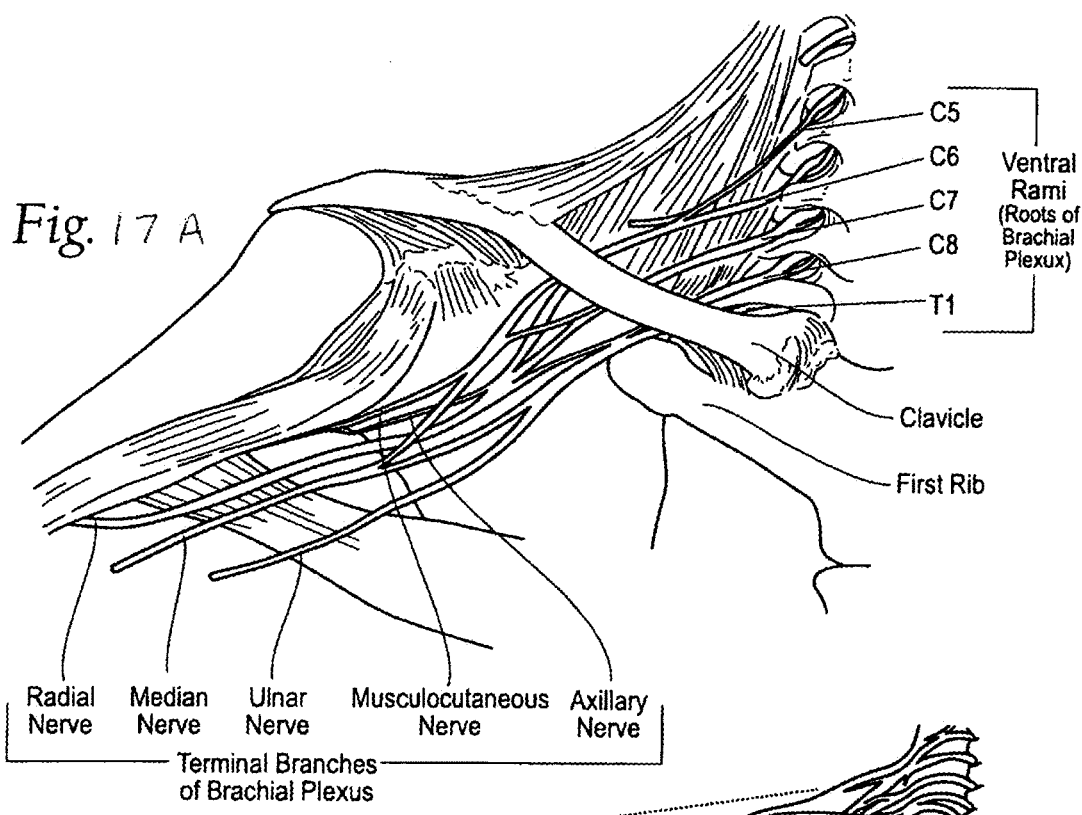
FIGS. 17A and 17B are anatomic views of the spinal nerves of the brachial plexus.
Figure 17B:
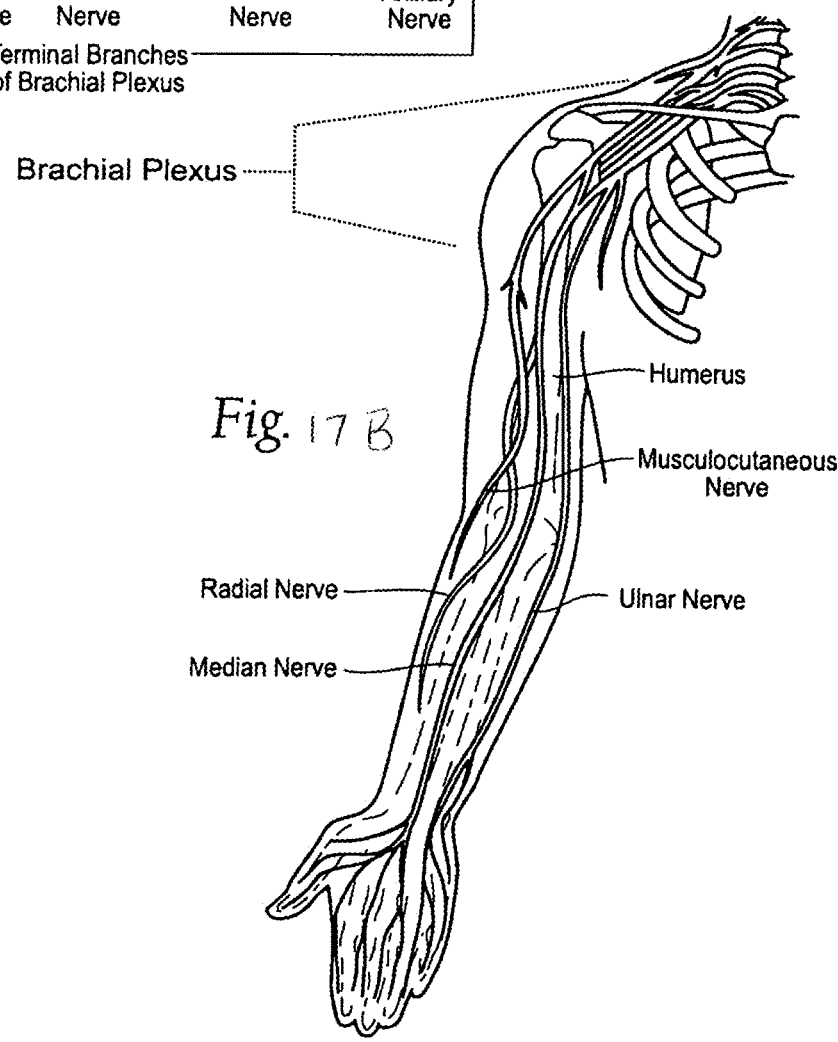

Most nerves in the upper limb arise from the brachial plexus, as shown in FIGS. 17A and 17B. The brachial plexus begins in the neck (vertebrae C5 through C7), forms trunks, and extends through divisions and cords into the axilla (underarm), where nearly all the nerve branches arise. Primary nerve branches of the brachial plexus include the musculocutaneous nerve; the median nerve; the ulnar nerve; the axillary nerve; and the radial nerve.

a. The Musculocutaneous Nerve

The musculocutaneous nerve arises from the lateral cord of the brachial plexus. Its fibers are derived from cervical vertebrae C5, C6. The musculocutaneous nerve penetrates the coracobrachialis muscle and passes obliquely between the biceps brachii and the brachialis, to the lateral side of the arm. Just above the elbow, the musculocutaneous nerve pierces the deep fascia lateral to the tendon of the biceps brachii continues into the forearm as the lateral antebrachial cutaneous nerve. In its course through the arm, the musculocutaneous nerve innervates the coracobrachialis, biceps brachii, and the greater part of the brachialis.

b. The Median Nerve

The median nerve is formed from parts of the medial and lateral cords of the brachial plexus, and continues down the arm to enter the forearm with the brachial artery. It originates from the brachial plexus with roots from cervical vertebrae C5, C6, C7 and thoracic vertebra T1. The median nerve innervates all of the flexors in the forearm, except flexor carpi ulnaris and that part of flexor digitorum profundus that supplies the medial two digits. The latter two muscles are supplied by the ulnar nerve of the brachial plexus. The median nerve is the only nerve that passes through the carpal tunnel, where it may be compressed to cause carpal tunnel syndrome.

The main portion of the median nerve supplies the following muscles: (i) the superficial group comprising pronator teres muscle; flexor carpi radialis muscle; palmaris longus muscle; and (ii) the intermediate group comprising flexor digitorum superficialis muscle.

The anteriornterosseus branch of the median nerve supplies the deep group comprising flexor digitorum profundus muscle (lateral halt); flexor pollicis longus muscle; and pronator quadratus.

In the hand, the median nerve supplies motor innervation to the 1st and 2nd lumbrical muscles. It also supplies the muscles of the thenar eminence by a recurrent thenar branch. The rest of the intrinsic muscles of the hand are supplied by the ulnar nerve of the brachial plexus.

The median nerve innervates the skin of the palmar side of the thumb, the index and middle finger, half the ring finger, and the nail bed of these fingers. The lateral part of the palm is supplied by the palmar cutaneous branch of the median nerve, which leaves the nerve proximal to the wrist creases. The palmar cutaneous branch travels in a separate fascial groove adjacent to the flexor carpi radialis and then superficial to the flexor retinaculum. It is therefore spared in carpal tunnel syndrome.

c. The Ulnar Nerve

The ulnar nerve comes from the medial cord of the brachial plexus, and descends on the posteromedial aspect of the humerus. It goes behind the medial epicondyle, through the cubital tunnel at the elbow (where it is vulnerable to injury for a few centimeters, just above the joint). One method of injuring the nerve is to strike the medial epicondyle of the humerus from posteriorly, or inferiorly with the elbow flexed. The ulnar nerve is trapped between the bone and the overlying skin at this point. This is commonly referred, to as hitting one's "funny bone."

The ulnar nerve is the largest nerve not protected by muscle or bone in the human body. The ulnar nerve is the only unprotected nerve that does not serve a purely sensory function. The ulnar nerve is directly connected to the little finger, and the adjacent half of the ring finger, supplying the palmar side of these fingers, including both front and back of the tips, as far back as the fingernail beds.

The ulnar nerve and its branches innervate muscles in the forearm and hand. In the forearm, the muscular branches of ulnar nerve innervates the flexor carpi ulnaris and the flexor digitorum profundus (medial half). In the hand, the deep branch of ulnar nerve innervates hypothenar muscles; opponens digiti minimi, abductor digiti minimi; flexor digiti minimi brevis; adductor pollicis; flexor pollicis brevis (deep head); the third and fourth lumbrical muscles; dorsal interossei; palmar interossei. In the hand, the superficial branch of ulnar nerve innervates palmaris brevis.

The ulnar nerve also provides sensory innervation to the fifth digit and the medial half of the fourth digit, and the corresponding part of the palm. The Palmar branch of ulnar nerve supplies cutaneous innervation to the anterior skin and nails. The dorsal branch of ulnar nerve supplies cutaneous innervation to the posterior skin (except the nails).

d. The Axillary Nerve

The axillary nerve comes off the posterior cord of the brachial plexus at the level of the axilla (armpit) and carries nerve fibers from vertebrae C5 and C6. The axillary nerve travels through the quadrangular space with the posterior circumflex humeral artery and vein. It supplies two muscles: the deltoid (a muscle of the shoulder), and the teres minor (one of the rotator cuff muscles). The axillary nerve also carries sensory information from the shoulder joint, as well as from the skin covering the inferior region of the deltoid muscle, i.e., the "regimental badge" area (which is innervated by the superior lateral cutaneous nerve branch of the axillary nerve). When the axillary nerve splits off from the posterior cord, the continuation of the cord is the radial nerve.

e. The Radial Nerve

The radial nerve supplies the upper limb, supplying the triceps brachii muscle of the arm, as well as all twelve muscles in the posterior osteofascial compartment of the forearm, as well as the associated joints and overlying skin. The radial nerve originates from the posterior cord of the brachial plexus with roots from cervical vertebrae C5, C6, C7, C8 and thoracic vertebra T1.

Cutaneous innervation is provided by the following nerves: (i) posterior cutaneous nerve of arm (originates in axilla); (ii) inferior lateral cutaneous nerve of arm (originates in arm); and (iii) posterior cutaneous nerve of forearm (originates in arm). The superficial branch of the radial nerve provides sensory innervation to much of the back of the hand, including the web of skin between the thumb and index finger.

Muscular branches of the radial nerve innervate the triceps brachii; anconeus brachioradialis; and the extensor carpi radialis longus.

The deep branch of the radial nerve innervates the extensor carpi radialis brevis; supinator; posterior interosseous nerve (a continuation of the deep branch after the supinator): extensor digitorum; extensor digiti minimi; extensor carpi ulnaris; abductor pollicis longus; extensor pollicis brevis; extensor pollicis longus; and extensor indicis.

The radial nerve (and its deep branch) provides motor innervation to the muscles in the posterior compartment of the arm and forearm, which are mostly extensors.

2. Sacral and Lumbar Plexuses

Figure 18:
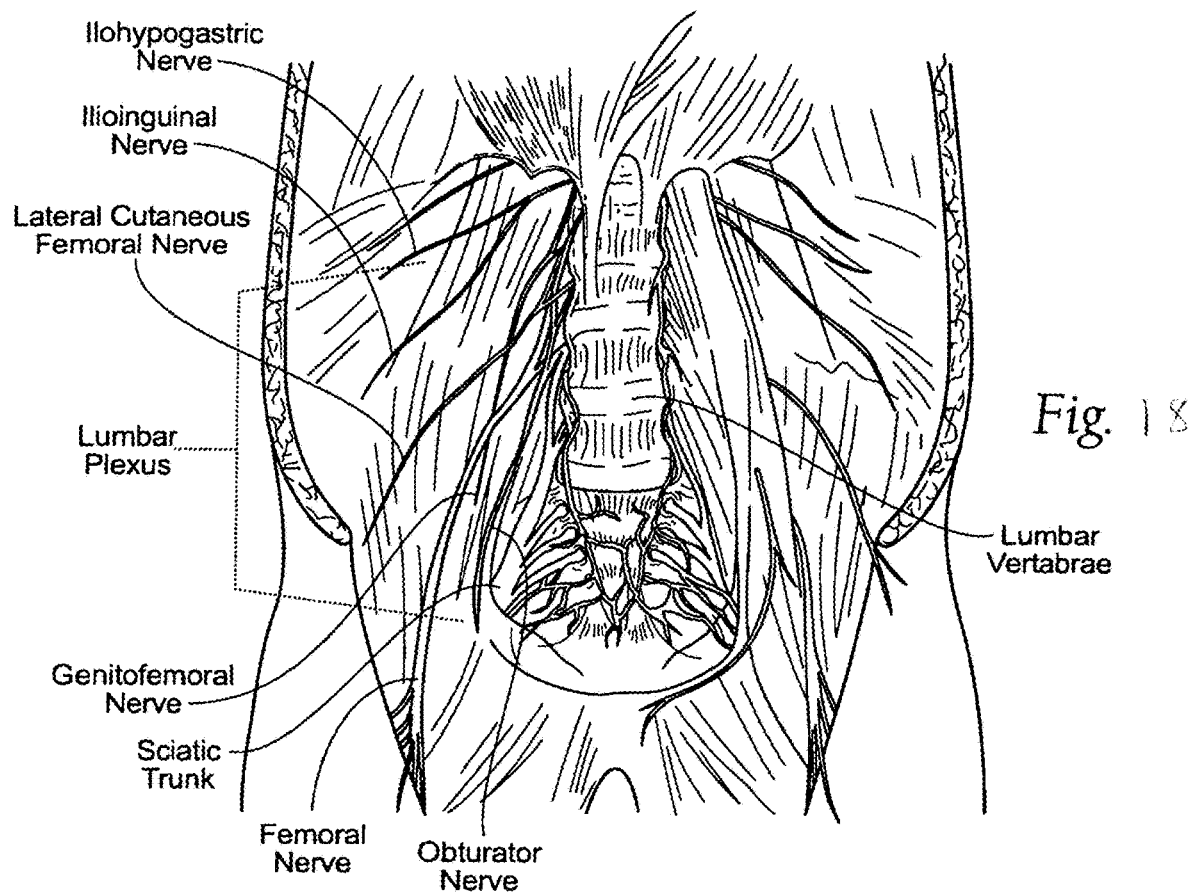
FIG. 18 is an anatomic views of the spinal nerves of the lumbar plexus.

The lumbar plexus (see FIG. 18) is a nervous plexus in the lumbar region of the body and forms part of the lumbosacral plexus. It is formed by the ventral divisions of the first four lumbar nerves (L1-L4) and from contributions of the subcostal thoracic nerve (T12), which is the last (most inferior) thoracic nerve.

Figure 19:
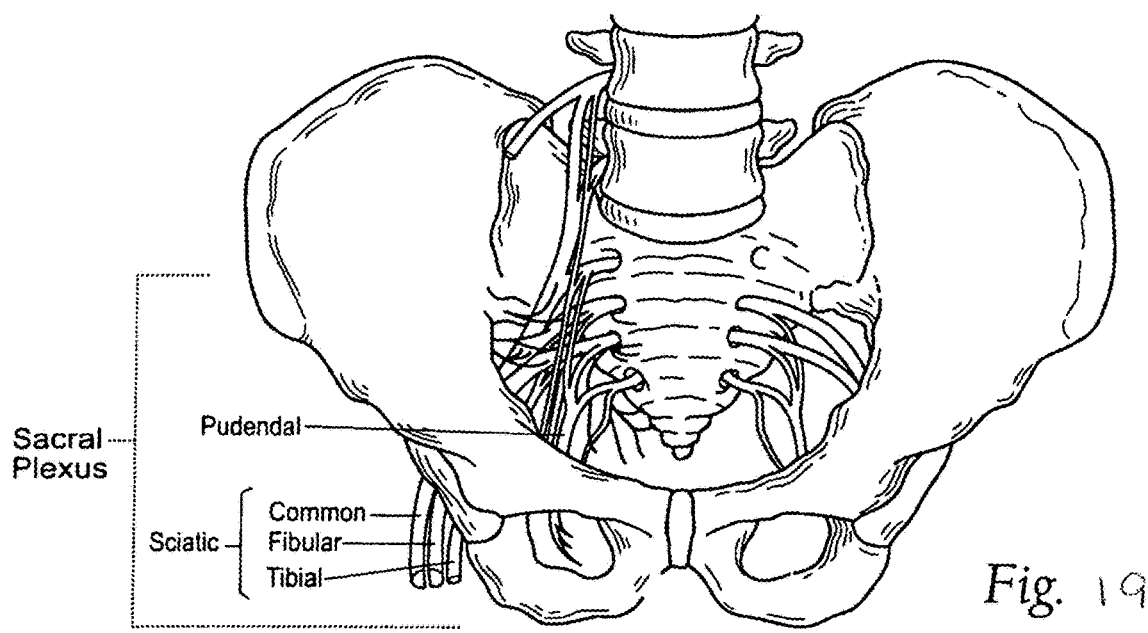
FIG. 19 is an anatomic view of the spinal nerves of the sacral plexus.

Additionally, the ventral rami of sacral vertebrae S2 and S3 nerves emerge between digitations of the piriformis and coccygeus muscles. The descending part of the lumbar vertebrae L4 nerve unites with the ventral ramus of the lumbar vertebrae L5 nerve to form a thick, cordlike lumbosacral trunk. The lumbosacral trunk joins the sacral plexus (see FIG. 19). The main nerves of the lower limbs arise from the lumbar and sacral plexuses.

a. Nerves of the Sacral Plexus The sacral plexus provides motor and sensory nerves for the posterior thigh, most of the lower leg, and the entire foot. (1) The Sciatic Nerve As shown in FIGS. 14A and 19, the sciatic nerve (also known as the ischiatic nerve) arises from the sacral plexus. It is the longest and widest single nerve in the human body. It begins in the lower back and runs through the buttock and down the lower limb. The sciatic nerve supplies nearly the whole of the skin of the leg, the muscles of the back of the thigh, and those of the leg and foot. It is derived from spinal nerves L4 through S3. It contains fibers from both the anterior and posterior divisions of the lumbosacral plexus.

The nerve gives off articular and muscular branches. The articular branches (rami articulares) arise from the upper part of the nerve and supply the hip joint, perforating the posterior part of its capsule; they are sometimes derived from the sacral plexus. The muscular branches (rami musculares) innervate the following muscles of the lower limb: biceps femoris, semitendinosus, semimembranosus, and adductor magnus. The nerve to the short head of the biceps femoris comes from the common peroneal part of the sciatic, while the other muscular branches arise from the tibial portion, as may be seen in those cases where there is a high division of the sciatic nerve.

The muscular branch of the sciatic nerve eventually gives off the tibial nerve (shown in FIG. 1A) and common peroneal nerve (also shown in FIG. 14A), which innervates the muscles of the (lower) leg. The tibial nerve goes on to innervate all muscles of the foot except the extensor digitorum brevis (which is innervated by the peroneal nerve).

b. Nerves of the Lumbar Plexus

The lumbar plexus (see FIG. 18) provides motor, sensory, and autonomic fibres to gluteal and inguinal regions and to the lower extremities. The gluteal muscles are the three muscles that make up the buttocks: the gluteus maximus muscle, gluteus medius muscle and gluteus minimus muscle. The inguinal region is situated in the groin or in either of the lowest lateral regions of the abdomen.

(1) The Iliohypogastric Nerve

The iliohypogastric nerve (see FIG. 18) runs anterior to the psoas major on its proximal lateral border to run laterally and obliquely on the anterior side of quadratus lumborum. Lateral to this muscle, it pierces the transversus abdominis to run above the iliac crest between that muscle and abdominal internal oblique. It gives off several motor branches to these muscles and a sensory branch to the skin of the lateral hip. Its terminal branch then runs parallel to the inguinal ligament to exit the aponeurosis of the abdominal external oblique above the external inguinal ring where it supplies the skin above the inguinal ligament (i.e. the hypogastric region) with the anterior cutaneous branch.

(2) The Ilioinguinal Nerve

The ilioinguinal nerve (see FIG. 18) closely follows the iliohypogastric nerve on the quadratus lumborum, but then, passes below it to run at the level of the iliac crest. It pierces the lateral abdominal wall and runs medially at the level of the inguinal ligament where it supplies motor branches to both transversus abdominis and sensory branches through the external inguinal ring to the skin over the pubic symphysis and the lateral aspect of the labia majora or scrotum.

(3) The Genitofemoral

The genitofemoral nerve (see FIG. 18) pierces psoas major anteriorly below the former two nerves to immediately split into two branches that run downward on the anterior side of the muscle. The lateral femoral branch is purely sensory. It pierces the vascular lacuna near the saphenous hiatus and supplies the skin below the inguinal ligament (i.e. proximal, lateral aspect of femoral triangle). The genital branch differs in males and females. In males it runs in the spermatic cord and in females in the inguinal canal together with the teres uteri ligament. It then sends sensory branches to the scrotal skin in males and the labia majora in females. In males it supplies motor innervation to the cremaster.

(4) The Lateral Cutaneous Femoral Nerve

The lateral cutaneous femoral nerve (see FIG. 18) pierces psoas major on its lateral side and runs obliquely downward below the iliac fascia. Medial to the anterior superior iliac spine it leaves the pelvic area through the lateral muscular lacuna. In the thigh it briefly passes under the fascia lata before it breaches the fascia and supplies the skin of the anterior thigh.

(5) The Obturator Nerve

The obturator nerve (see FIG. 18) leaves the lumbar plexus and descends behind psoas major on it medial side, then follows the linea terminalis and exits through the obturator canal. In the thigh, it sends motor branches to obturator externus before dividing into an anterior and a posterior branch, both of which continues distally. These branches are separated by adductor brevis and supply all thigh adductors with motor innervation: pectineus, adductor longus, adductor brevis, adductor magnus, adductor ninimus, and gracilis. The anterior branch contributes a terminal, sensory branch which passes along the anterior border of gracilis and supplies the skin on the medial, distal part of the thigh.

(6) The Femoral Nerve

The femoral nerve (see FIG. 18 and also FIG. 19A) is the largest and longest nerve of the lumbar plexus. It gives motor innervation to iliopsoas, pectineus, sartorius, and quadriceps femoris; and sensory innervation to the anterior thigh, posterior lower leg, and hindfoot. It runs in a groove between psoas major and iliacus giving off branches to both muscles. In the thigh it divides into numerous sensory and muscular branches and the saphenous nerve, its long sensory terminal branch which continues down to the foot.

3. The Cervical Plexus

The cervical plexus (see FIG. 20) is a plexus of the ventral rami of the first four cervical spinal nerves which are located from C1 to C4 cervical segment in the neck. They are located laterally to the transverse processes between prevertebral muscles from the medial side and vertebral (m. scalenus, m. levator scapulae, m. splenius cervicis) from lateral side. Here there is anastomosis with accessory nerve, hypoglossal nerve and sympathetic trunk.

The cervical plexus is located in the neck, deep to sternocleidomastoid. Nerves formed from the cervical plexus innervate the back of the head, as well as some neck muscles. The branches of the cervical plexus emerge from the posterior triangle at the nerve point, a point which lies midway on the posterior border of the Stemocleidomastoid.

The nerves formed by the cervical plexus supply the back of the head, the neck and the shoulders. The face is supplied by a cranial nerve, the trigeminal nerve. The upper four posterior primary rami are larger than the anterior primary rami. The C1 posterior primary ramus does not usually supply the skin. The C2 posterior primary ramus forms the greater occipital nerve which supplies the posterior scalp. The upper four anterior primary rami form the cervical plexus. The cervical plexus supplies the skin over the anterior and lateral neck to just below the clavicle. The plexus also supplies the muscles of the neck including the scalenes, the strap muscles, and the diaphragm.

The cervical plexus has two types of branches: cutaneous and muscular.

The cutaneous branches include the lesser occipital nerve, which innervates lateral part of occipital region (C2 nerve only); the great auricular nerve, which innervates skin near concha auricle and external acoustic meatus (C2 and C4 nerves); the transverse cervical nerve, which innervates anterior region of neck (C2 and C3 nerves); and the supraclavicular nerves, which innervate region of suprascapularis, shoulder, and upper thoracic region (C3, C4 Nerves)

The muscular branches include the ansa cervicalis (loop formed from C1-C3), etc. (geniohyoid (C1 only), thyrohyoid (C1 only), sternothyroid, sternohyoid, omohyoid); phrenic (C3-05 (primarily C4)), which innervates the diaphragm; the segmental branches (C1-C4), which innervate the anterior and middle scalenes.

4. The Solar Plexus

The solar plexus (see FIG. 21) is a dense cluster of nerve cells and supporting tissue, located behind the stomach in the region of the celiac artery just below the diaphragm. It is also known as the celiac plexus. Rich in ganglia and interconnected neurons, the solar plexus is the largest autonomic nerve center in the abdominal cavity. Through branches it controls many vital functions such as adrenal secretion and intestinal contraction.

Derived from the solar plexus are the phrenic plexus (producing contractions of the diaphragm, and providing sensory innervation for many components of the mediastinum and pleura); the renal plexuses (affecting renal function); the spermatic plexus (affecting function of the testis); as well as the gastric plexus; the hepatic plexus; the splenic plexus; the superior mesenteric plexus; and the aortic plexus.

VI. The System

The various aspects of the invention will be described in connection with the placement of one or more leads 12 having one or more electrodes 14, in muscle, and in electrical proximity but away from nerves, for improved recruitment of targeted nerves for therapeutic purposes, such as for the treatment of pain. That is because the features and advantages that arise due to the invention are well suited to this purpose. It is to be appreciated that regions of pain can include any or all portions of the body, including arms and legs in both humans and animals.

A. Stimulation of Nerves of Passage

Figure 22:
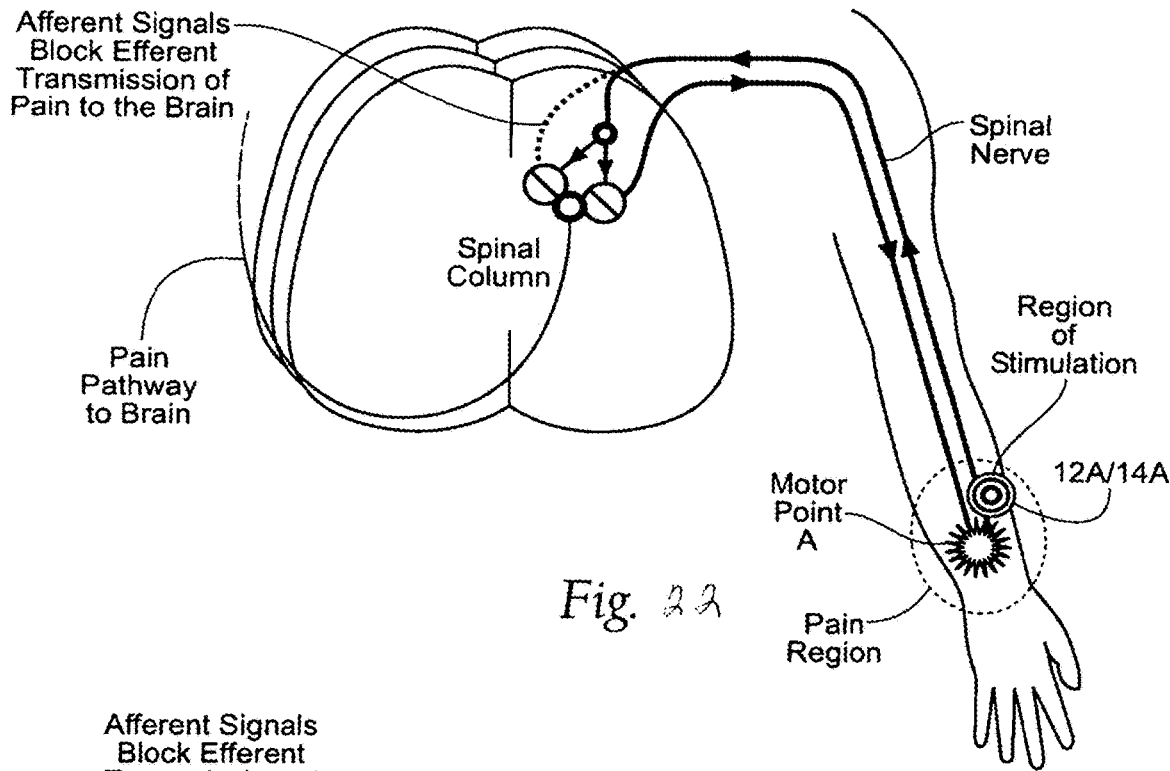
FIG. 22 is an idealized, diagrammatic view showing a motor point stimulation system.

FIG. 22 shows a typical "motor point" system and method for stimulating a nerve or muscle A by placing a lead 12(A) with its electrode 14(A) close to motor point A. As previously described, a motor point A is the location where the innervating spinal nerve enters the muscle. At that location, the electrical stimulation intensity required to elicit a full contraction is at the minimum. Any other location in the muscle would require more stimulation intensity to elicit the same muscle contraction.

Figure 23:
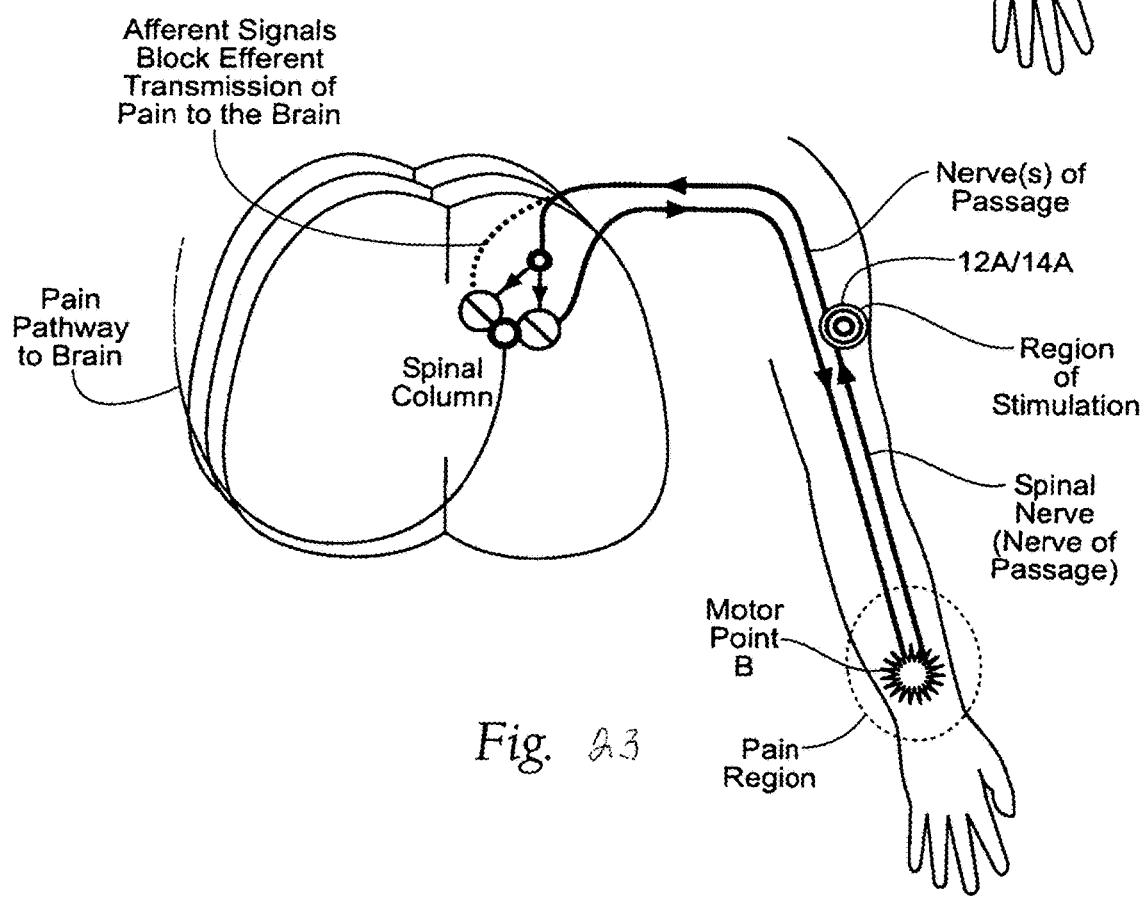
FIG. 23 is an idealized, diagrammatic view showing a nerve of passage stimulation system.

FIG. 23 shows a "nerves of passage" system and method, that is unlike the "motor point" system and method shown in FIG. 22, and which incorporates the features of the invention. As shown in FIG. 23, the system and method identifies a region where there is a local manifestation of pain. The region of pain can comprise, e.g., skin, bone, a joint, or muscle. The system and method identify one or more spinal nerves that are located anatomically upstream or cranial to the region where pain is manifested, through which neural impulses comprising the pain pass. A given spinal nerve that is identified can comprise a nerve trunk located in a nerve plexus, or a divisions and/or a cord of a nerve trunk, or a nerve branch, provided that it is upstream or cranial of where the nerve innervates the region affected by the pain. The given spinal nerve can be identified by medical professionals using textbooks of human anatomy along with their knowledge of the site and the nature of the pain or injury, as well as by physical manipulated and/or imaging, e.g., by ultrasound, fluoroscopy, or X-ray examination, of the region where pain is manifested. A desired criteria of the selection includes identifying the location of muscle in electrical proximity to but spaced away from the nerve or passage, which muscle can be accessed by placement of one or more stimulation electrodes, aided if necessary by ultrasonic or electro-location techniques. The nerve identified comprises a targeted "nerve of passage." The muscle identified comprises the "targeted muscle." In a preferred embodiment, the electrodes are percutaneously inserted using percutaneous leads.

The system and method place the one or more leads 12(B) with its electrode 14(B) in the targeted muscle in electrical proximity to but spaced away from the targeted nerve of passage. The system and method apply electrical stimulation through the one or more stimulation electrodes to electrically activate or recruit the targeted nerve of passage that conveys the neural impulses comprising the pain to the spinal column.

The system and method can apply electrical stimulation to nerves of passage throughout the body. For example, the nerves of passage can comprise one or more spinal nerves in the brachial plexus, to treat pain in the chest, shoulders, arms and hands; and/or one or more spinal nerves in the lumbar plexus, to treat pain in the back, abdomen, groin, thighs, knees, and calves; and/or one or more spinal nerves in the sacral plexus, to treat pain in the buttocks, thighs, calves, and feet; and/or one or more spinal nerves in the cervical plexus, to treat pain in the head, neck and shoulders; and/or one or more spinal nerves in the solar plexus, to treat pain or dysfunction in internal organs.

For example, if the pinky finger hurts, the system and method can identify and stimulate the ulnar nerve at a location that it is upstream or cranial of where the nerve innervates the muscle or skin of the pinky finger, e.g., in the palm of the hand, forearm, and/or upper arm. If electrical stimulation activates the target nerve of passage sufficiently at the correct intensity, then the patient will feel a comfortable tingling sensation called a paresthesia in the same region as their pain, which overlap with the region of pain and/or otherwise reduce pain.

It is to be appreciated that the sensation could be described with other words such as buzzing, thumping, etc. Evoking paresthesias in the region of pain confirms correct lead placement and indicates stimulus intensity is sufficient to reduce pain. Inserting a lead 12 percutaneously allows the lead 12 to be placed quickly and easily, and placing the lead 12 in a peripheral location, i.e., muscle, where it is less likely to be dislodged, addresses the lead migration problems of spinal cord stimulation that result in decreased paresthesia coverage, decreased pain relief, and the need for frequent patient visits for reprogramming.

Placing the lead 12 percutaneously in muscle in electrical proximity to but spaced away from the targeted nerve of passage minimize complications related to lead placement and movement. In a percutaneous system, an electrode lead 12, such as a coiled fine wire electrode lead may be used because it is minimally-invasive and well suited for placement in proximity to a nerve of passage. The lead can be sized and configured to withstand mechanical forces and resist migration during long-term use, particularly in flexible regions of the body, such as the shoulder, elbow, and knee.

B. The Lead

Figure 24A:
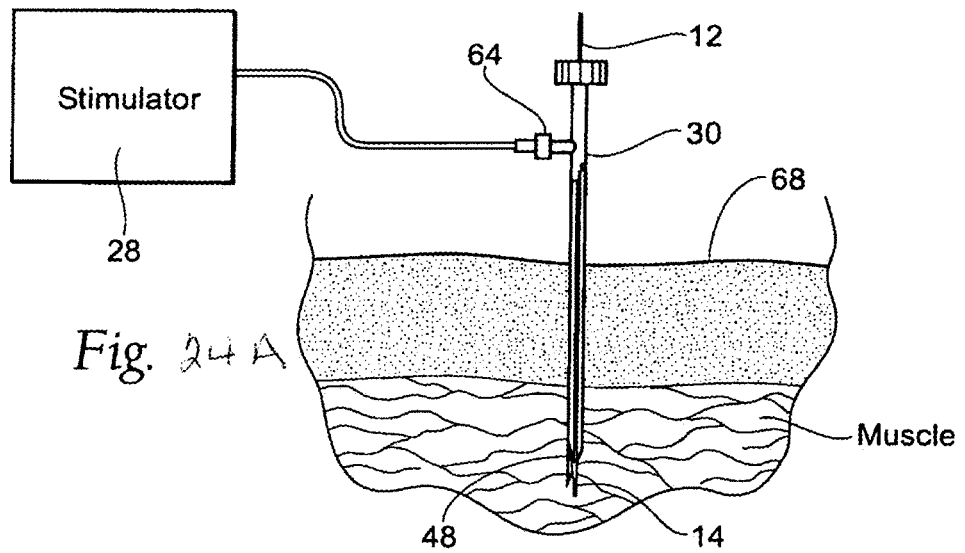
FIGS. 24A to 24D are views showing a percutaneous lead that can form a part of a nerve of passage stimulation system.
Figure 24B:
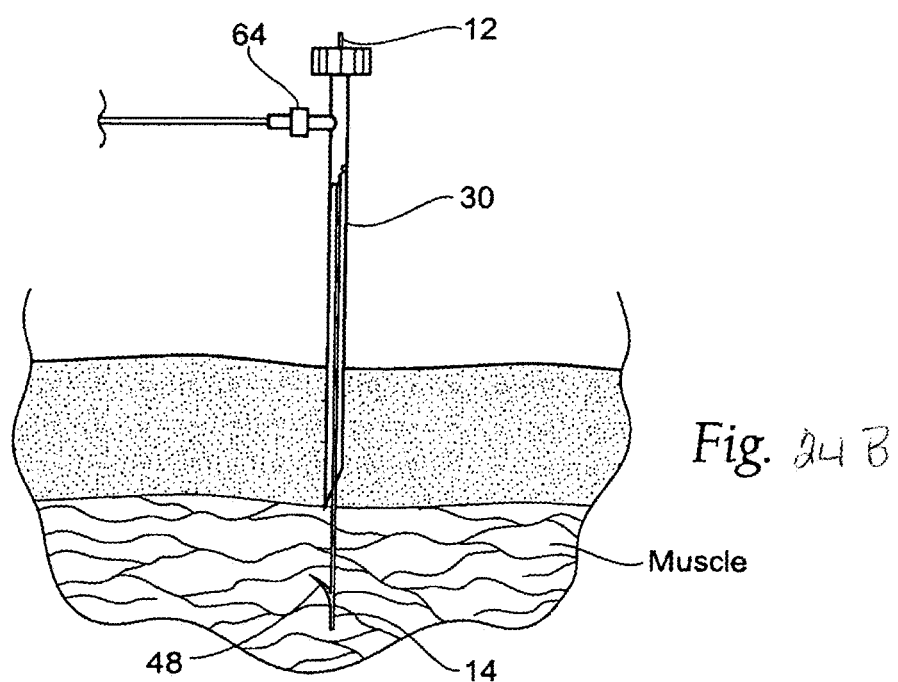
Figure 24C:
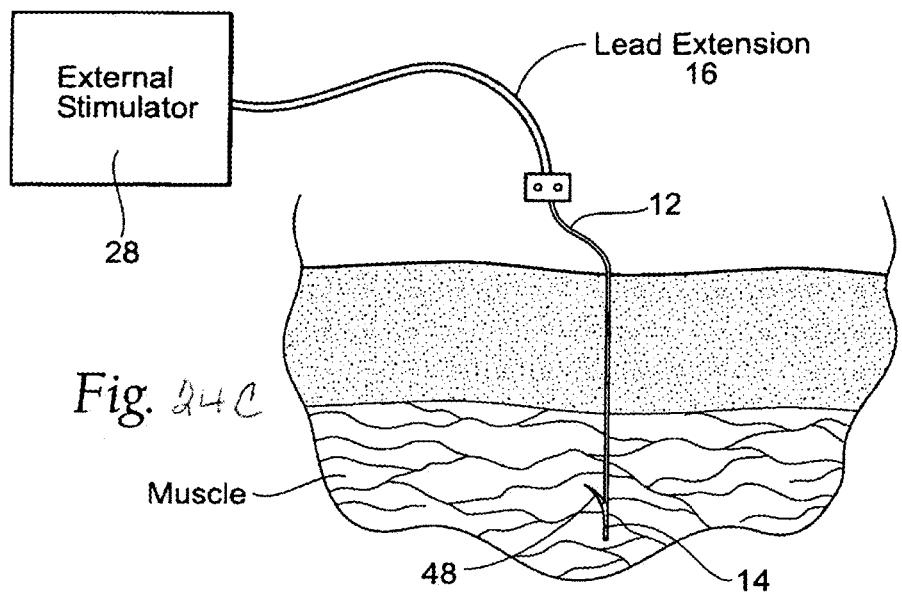

As FIG. 24A shows, the electrode lead can comprise, e.g., a fine wire electrode 14, paddle electrode, intramuscular electrode, or general-purpose electrode, inserted via a needle introducer 30 or surgically implanted in proximity of a targeted nerve of passage. Once proper placement is confirmed, the needle introducer 30 may be withdrawn (as FIGS. 24B and 24C show), leaving the electrode in place. Stimulation may also be applied through a penetrating electrode, such as an electrode array comprised of any number (i.e., one or more) of needle-like electrodes that are inserted into the target site. In both cases, the lead may placed using a needle-like introducer 30, allowing the lead/electrode placement to be minimally invasive.

In a representative embodiment, the lead 12 comprises a thin, flexible component made of a metal and/or polymer material. By "thin," it is contemplated that the lead should not be greater than about 0.75 mm (0.030 inch) in diameter.

The lead 12 can comprise, e.g., one or more coiled metal wires with in an open or flexible elastomer core. The wire can be insulated, e.g., with a biocompatible polymer film, such as polyfluorocarbon, polyimide, or parylene. The lead is desirably coated with a textured, bacteriostatic material, which helps to stabilize the lead in a way that still permits easy removal at a later date and increases tolerance.

The lead 12 may be electrically insulated everywhere except at one (monopolar), or two (bipolar), or three (tripolar), for example, conduction locations near its distal tip. Each of the conduction locations may be connected to one or more conductors that run the length of the lead and lead extension 16 (see FIG. 24C), proving electrical continuity from the conduction location through the lead 12 to an external pulse generator or stimulator 28 (see FIG. 24C) or an implanted pulse generator or stimulator 28 (see FIG. 24D).

The conduction location or electrode 14 may comprise a de-insulated area of an otherwise insulated conductor that runs the length of an entirely insulated electrode. The de-insulated conduction region of the conductor can be formed differently, e.g., it can be wound with a different pitch, or wound with a larger or smaller diameter, or molded to a different dimension. The conduction location or the electrode 14 may comprise a separate material (e.g., metal or a conductive polymer) exposed to the body tissue to which the conductor of the wire is bonded.

The lead 12 is desirably provided in a sterile package 62 (see FIG. 25), and may be pre-loaded in the introducer needle 30. The package 62 can take various forms and the arrangement and contents of the package 62. As shown in FIG. 12, the package 62 comprises a sterile, wrapped assembly. The package 62 includes an interior tray made, e.g., from die cut cardboard, plastic sheet, or thereto-formed plastic material, which hold the contents. The package 62 also desirably includes instructions for use 58 for using the contents of the package to carry out the lead location and placement procedures, as will be described in greater detail below.

The lead 12 desirably possess mechanical properties in terms of flexibility and fatigue life that provide an operating life free of mechanical and/or electrical failure, taking into account the dynamics of the surrounding tissue (i.e., stretching, bending, pushing, pulling, crushing, etc.). The material of the electrode 14 desirably discourages the in-growth of connective tissue along its length, so as not to inhibit its withdrawal at the end of its use. However, it may be desirable to encourage the in-growth of connective tissue at the distal tip of the electrode, to enhance its anchoring in tissue.

Figure 26A:
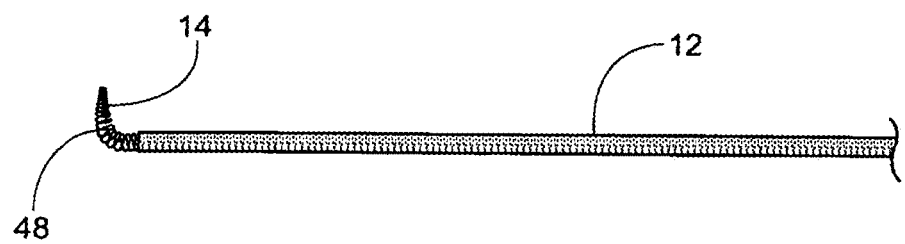
FIGS. 26A/B and 27A/B are representative leads that can form a part of a nerve of passage stimulation system.
Figure 26B:
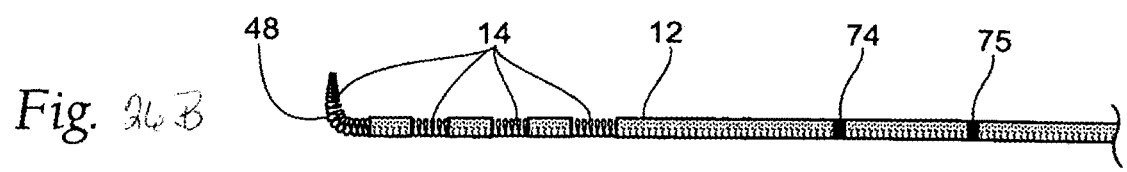

One embodiment of the lead 12 shown in FIG. 26A may comprise a minimally invasive coiled fine wire lead 12 and electrode 14. The electrode 14 may also include, at its distal tip, an anchoring element 48. In the illustrated embodiment, the anchoring element 48 takes the form of a simple barb or bend (see also FIG. 24C). The anchoring element 48 is sized and configured so that, when in contact with tissue, it takes purchase in tissue, to resist dislodgement or migration of the electrode out of the correct location in the surrounding tissue. Desirably, the anchoring element 48 is prevented from fully engaging body tissue until after the electrode 14 has been correctly located and deployed.

Figure 27A:
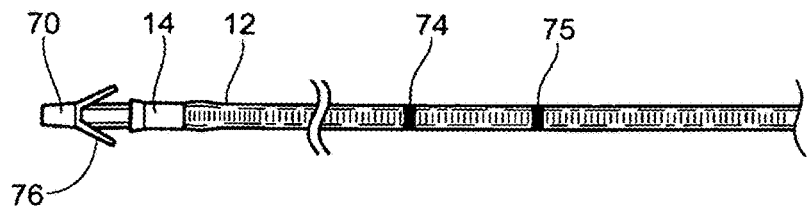
Figure 27B:
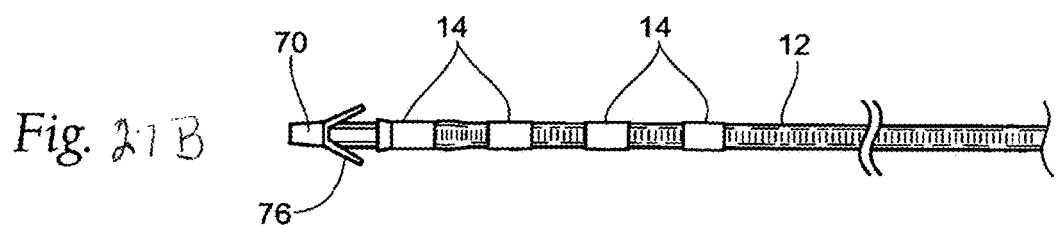

An alternative embodiment of an electrode lead 12 shown in FIGS. 27A and 27B, may also include, at or near its distal tip or region, one or more anchoring element(s) 70. In the illustrated embodiment, the anchoring element 70 takes the form of an array of shovel-like paddles or scallops 76 proximal to the proximal-most electrode 14 (although a paddle 76 or paddles could also be proximal to the distal most electrode 14, or could also be distal to the distal most electrode 14). The paddles 76 as shown are sized and configured so they will not cut or score the surrounding tissue. The anchoring element 70 is sized and configured so that, when in contact with tissue, it takes purchase in tissue, to resist dislodgement or migration of the electrode out of the correct location in the surrounding tissue (e.g., muscle 54). Desirably, the anchoring element 70 is prevented from fully engaging body tissue until after the electrode 14 has been deployed. The electrode is not deployed until after it has been correctly located during the implantation (lead placement) process, as previously described. In addition, the lead 12 may include one or more ink markings 74, 75 (shown in FIG. 27A) to aid the physician in its proper placement.

Alternatively, or in combination, stimulation may be applied through any type of nerve cuff (spiral, helical, cylindrical, book, flat interface nerve electrode (FINE), slowly closing FINE, etc.), paddle (or paddle-style) electrode lead, cylindrical electrode lead, and/or other lead that is surgically or percutaneously placed within muscle at the target site.

Figure 24D:
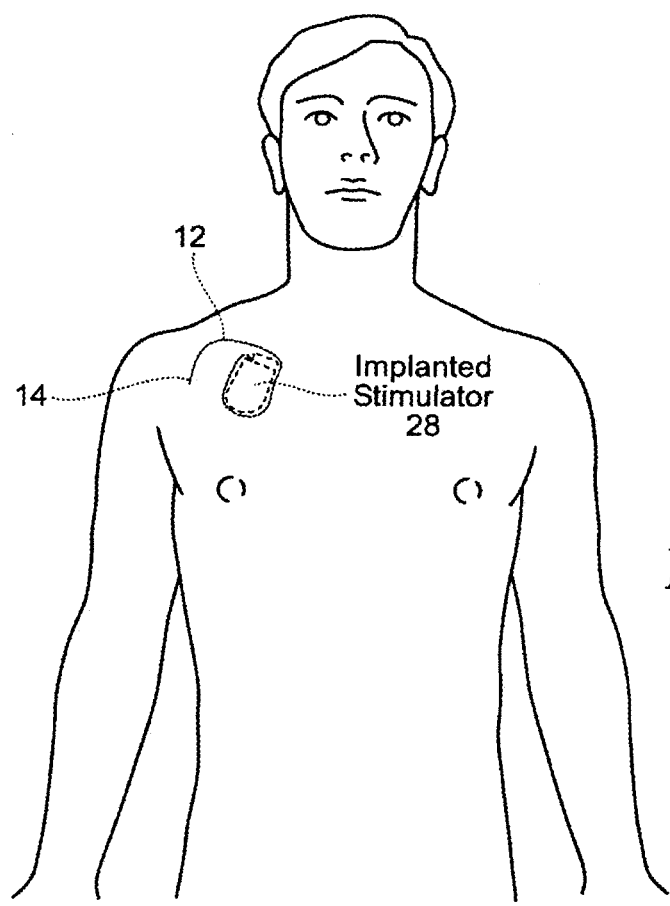

In all cases, the lead may exit through the skin and connect with one or more external stimulators 28 (shown in FIG. 24C), or the lead(s) may be routed subcutaneously to one or more implanted pulse generators 28 (shown in FIG. 24D), or they may be connected as needed to internal and external coils for RF (Radio Frequency) wireless telemetry communications or an inductively coupled telemetry to control the implanted pulse generator. As shown in FIG. 24D, the implanted pulse generator 28 may be located some distance (remote) from the electrode 14, or an implanted pulse generator may be integrated with an electrode(s) (not shown), eliminating the need to route the lead subcutaneously to the implanted pulse generator.

The introducer 30 (see FIG. 24A) may be insulated along the length of the shaft, except for those areas that correspond with the exposed conduction surfaces of the electrode 14 housed inside the introducer 30. These surfaces on the outside of the introducer 30 are electrically isolated from each other and from the shaft of the introducer 30. These surfaces may be electrically connected to a connector 64 at the end of the introducer body (see FIG. 24A). This allows connection to an external stimulator 28 (shown in FIG. 24A) during the implantation process. Applying stimulating current through the outside surfaces of the introducer 30 provides a close approximation to the response that the electrode 14 will provide when it is deployed at the current location of the introducer 30.

The introducer 30 may be sized and configured to be bent by hand prior to its insertion through the skin. This will allow the physician to place lead 12 in a location that is not in an unobstructed straight line with the insertion site. The construction and materials of the introducer 30 allow bending without interfering with the deployment of the lead 12 and withdrawal of the introducer 30, leaving the lead 12 in the tissue.

C. Insertion of the Lead

Representative lead insertion techniques will now be described to place an electrode lead 12 in a desired location in muscle in electrical proximity to but spaced away from a nerve of passage. It is this lead placement that makes possible the stimulation of the targeted nerve or nerves of passage with a single lead 12 to provide pain relief.

Instructions for use 58 (see FIG. 25) can direct use of system and method for the placement of a lead 12 in muscle in electrical proximity to but spaced away from the nerve or nerves of passage for improved recruitment of target nerves, e.g., with the placement of one or more leads 12. The instructions for use may include instructions for placing a lead 12 for the activation of the targeted nerve of passage in a system for the relief of pain, for example. The instructions for use may also include instructions for recording stimulus parameters, including intensity associated with a first sensation of stimulation, a first noticeable muscle contraction, and a maximum tolerable contraction at multiple locations, which can be used to aid in determining desired stimulation parameters for optimal stimulation.

Figure 25:
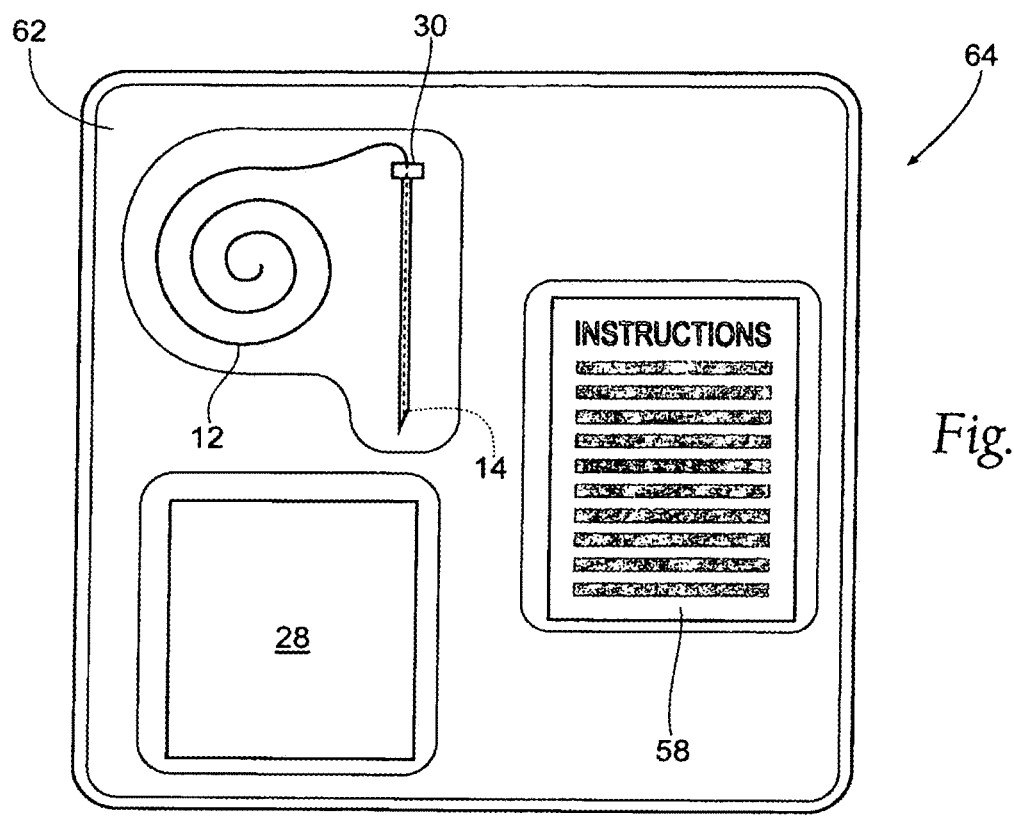
FIG. 25 is a view of a package containing a nerve of passage stimulation system.

The instructions 58 can, of course vary. The instructions 58 may be physically present in a kits holding the lead 12 (as FIG. 25 shows), but can also be supplied separately. The instructions 58 can be embodied in separate instruction manuals, or in video or audio tapes, CD's, and DVD's. The instructions 58 for use can also be available through an internet web page.

To determine the optimal placement for the lead 12, test stimulation may be delivered through needle electrodes, and muscle responses may be observed. The motor point(s) of the target muscle(s) may be located first in order to confirm that the muscles are innervated. Needle electrodes may be used because they can be easily repositioned until the optimal location to deliver stimulation is determined.

At least one lead(s) may be placed in muscle tissue near a targeted nerve of passage. The lead may be inserted via the introducer 30 in conventional fashion, which may be similar in size and shape to a hypodermic needle. The introducer 30 may be any size. In a preferred embodiment, the introducer 30 may range in size from 17 gauge to 26 gauge. Prior to inserting the introducer 30, the insertion site may be cleaned with a disinfectant (e.g. Betadine, 2% Chlorhexidine/80% alcohol, 10% povidone-iodine, or similar agent). A local anesthetic(s) may be administered topically and/or subcutaneously to the area in which the electrode and/or introducer will be inserted.

The position of the electrodes may be checked by imaging techniques, such as ultrasound, fluoroscopy, or X-rays. Following placement of the lead(s), the portion of the leads which exit the skin may be secured to the skin using covering bandages and/or adhesives.

Electrical stimulation may be applied to the targeted nerve of passage during and after placement of the electrode to determine whether stimulation of the targeted nerve of passage can generate comfortable sensations or paresthesias that overlap with the region of pain and/or reduce pain. The pain may be perceived to be contained within a specific part(s) of the body and/or it may be perceived to be located outside of the body, as may be the case in persons with amputations who have phantom pain or pain in the amputated (or phantom) limb(s).

In a percutaneous system 10 (as FIGS. 24A to 24D show, the lead 12 may be percutaneously placed near the targeted nerve of passage and exit at a skin puncture site 16. A trial or screening test may be conducted in a clinical setting (e.g. an office of a clinician, a laboratory, a procedure room, an operating room, etc.). During the trial, the lead is coupled to an external pulse generator 28 and temporary percutaneous and/or surface return electrodes, to confirm paresthesia coverage and/or pain relief of the painful areas.

If the clinical screening test is successful, the patient may proceed to a home-trial coupled to an external pulse generator 28 (as shown in FIG. 24C) and temporary percutaneous and/or surface return electrodes, to determine if pain relief can be sustained in the home environment. The trial period may range from minutes to hours to days to weeks to months. The preferred trial period may be between 3 and 21 days.

If either the screening test or home trial is unsuccessful, the lead 12 may be quickly and easily removed.

However, if the screening test and/or home-trial are successful, the patient's percutaneous system may be converted into a fully implanted system (as shown in FIG. 24D) by replacing the external pulse generator with an implantable pulse generator 28 (the housing of which serves as a return electrode).

Alternatively, it may be preferred to use a percutaneous system(s) as a therapy without proceeding to a fully implantable system. It is also to be appreciated that a home-trial is not a requirement for either the percutaneous system or a fully implanted system.

The duration of therapy for a percutaneous system may range from minutes to days to weeks to months to multiple years, but a preferred embodiment includes a duration ranging from 1 to 12 weeks.

Electrical stimulation is applied between the lead and return electrodes (uni-polar mode). Regulated current is the preferred type of stimulation, but other type(s) of stimulation (e.g. non-regulated current such as voltage-regulated) may also be used. Multiple types of electrodes may be used, such as surface, percutaneous, and/or implantable electrodes. The surface electrodes may be a standard shape or they may be tailored if needed to fit the contour of the skin.

In a preferred embodiment of a percutaneous system, the surface electrode(s) may serve as the anode(s) (or return electrode(s)), but the surface electrode(s) may be used as the cathode(s) (active electrode(s)) if necessary. When serving as a return electrode(s), the location of the electrode(s) is not critical and may be positioned anywhere in the general vicinity, provided that the current path does not cross the heart. If a surface electrode(s) serves as an active electrode(s), it (they) may be positioned near the target stimulation area(s) (e.g. on the skin surface over the target nerve or passage).

The electrode lead may be placed via multiple types of approaches. In one embodiment, the approach may be similar needle placement for electromyography (EMG).

Figure 28A:
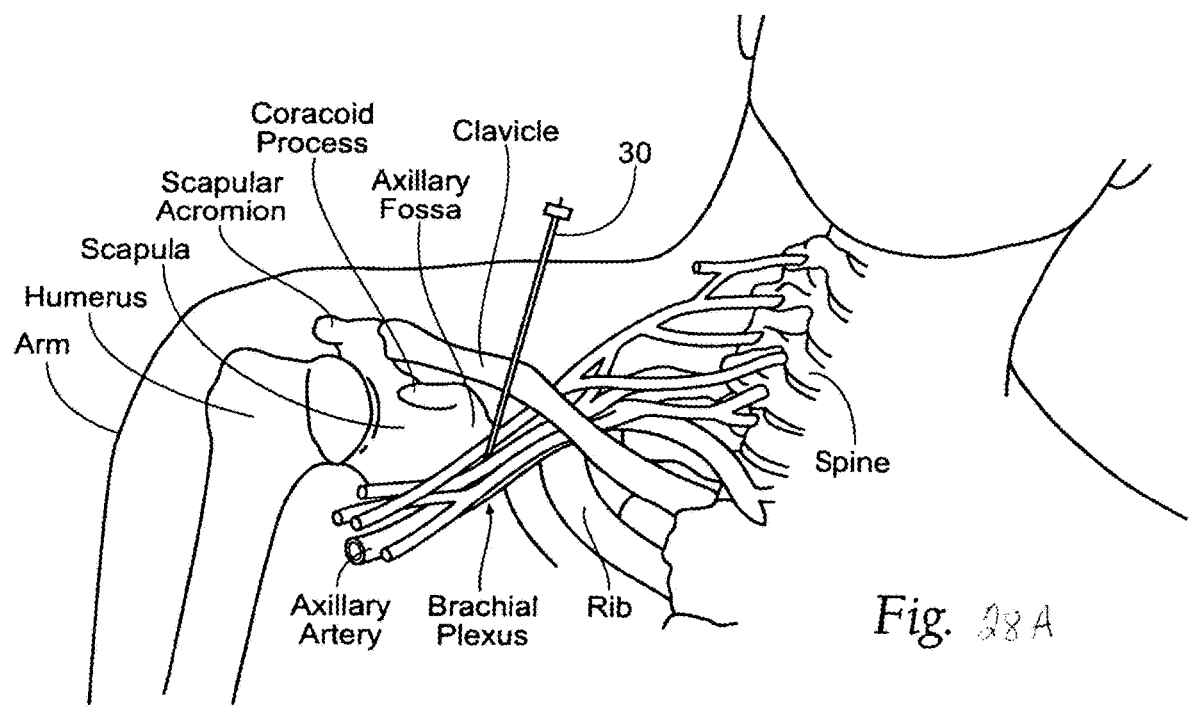
FIGS. 28A and 28B are schematic anatomic views of a system for applying nerve of passage stimulation to spinal nerves in the brachial plexus.

For example (as shown in FIG. 28A), if the targeted nerve of passage includes nerves of the brachial plexus, the approach can include:

Place the patient in a comfortable and/or appropriate position with head turned away from the lead insertion site.

Prepare the lead insertion site with antiseptic and local subcutaneous anesthetic (e.g., 2% lidocaine).

Locate the site of skin puncture with appropriate landmarks, such as the clavicle, coracoid process, and axilla, as necessary.

Insert a sterile percutaneous electrode lead 12 preloaded in the introducer needle 30 at a predetermined angle based on landmarks used.

Place a surface stimulation return electrode in proximity of the area in which the percutaneous lead 12 has been placed. Test stimulation will be applied to the lead 12, with the surface electrode providing a return path. The surface electrode may be placed adjacent to the lead. Its position is not critical to the therapy and it can be moved throughout the therapy to reduce the risk of skin irritation.

Couple the lead 12 to the external pulse generator 28 and to the return electrode. Set the desired stimulation parameters. Test stimulation may be delivered using a current-regulated pulse generator, for example. The external pulse generator 28 may be programmed to 4 mA, 100 μs, 100 Hz, and an on-off duty cycle of 0.25 sec., as a non-limiting example.

Advance the introducer slowly until the subject reports the first evoked sensation in the region experiencing pain. Progressively reduce the stimulus amplitude and advance the introducer more slowly until the sensation can be evoked in the painful region at a predetermined stimulus amplitude (e.g., 1 mA). Stop the advancement of the introducer, and increase the stimulus amplitude in small increments (e.g., 0.1 mA) until the stimulation-evoked tingling sensation (paresthesia) expands to overlay the entire region of pain.

Figure 28B:
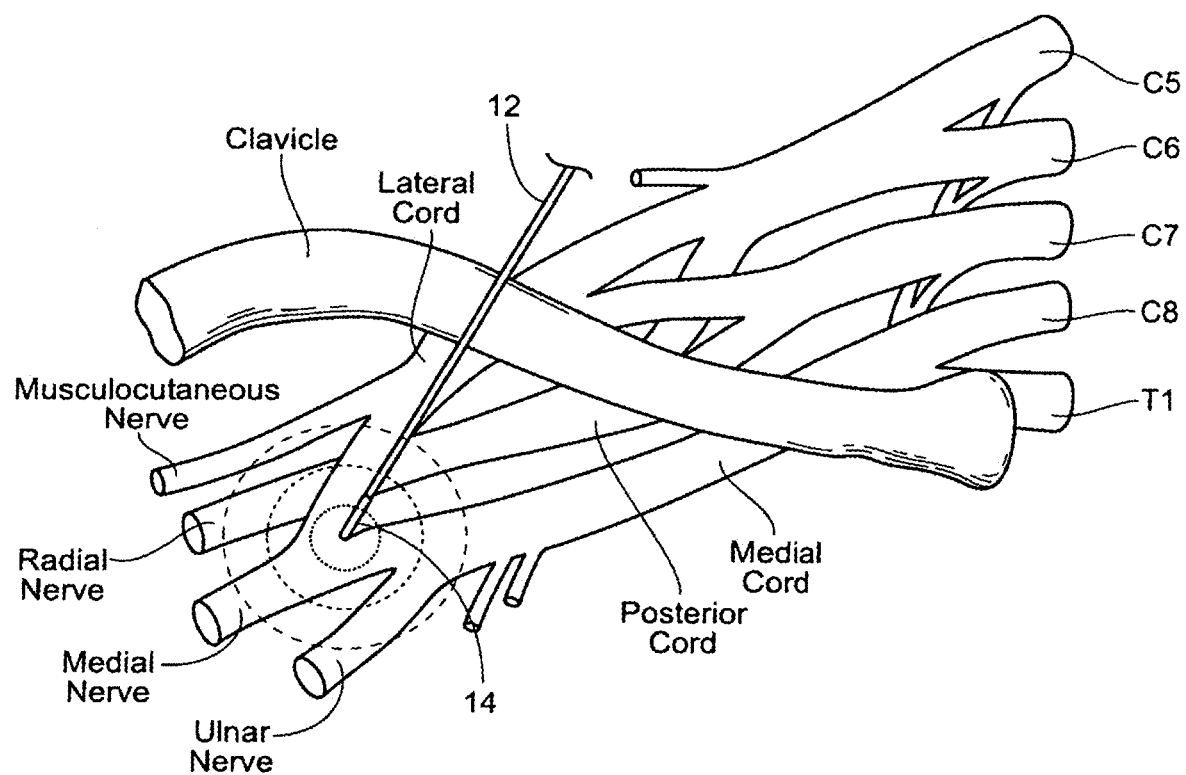

Withdraw the introducer 30, leaving the percutaneous lead 12 in proximity but away from the target nerve (see FIG. 28B).

Cover the percutaneous exit site and lead 12 with a bandage. A bandage may also be used to secure the external portion of the lead 12 (or an extension cable used to couple the lead 12 to the external pulse generator) to the skin. It is expected the length of time to place the lead 12 to be less than 10 minutes, although the process may be shorter or longer.

Vary the stimulus amplitude in small steps (e.g., 0.1-0.5 mA) to determine the thresholds at which stimulation evokes first sensation (TSEN), sensation (paresthesia) superimposed on the region of pain (TSUP), muscle twitch (THUS) of the target muscle (innervated or not innervated by the target nerve), and maximum comfortable sensation (TMAX). Query the subject at each stimulus amplitude to determine sensation level, and visually monitor muscle response. Record the results.

It is possible that stimulation intensity may need to be increased slightly during the process due to causes such as habituation or the subject becoming accustomed to sensation, but the need for increased intensity is unlikely and usually only occurs after several days to weeks to months as the tissue encapsulates and the subject accommodates to stimulation. It is to be appreciated that the need for increased intensity could happen at any time, even years out, which would likely be due to either lead migration or habituation, but may also be due reasons ranging from nerve damage to plasticity/reorganization in the central nervous system.

If paresthesias cannot be evoked with the initial lead placement, redirect the introducer 30.

If sensations still cannot be evoked in a given subject, then the muscle twitch response of the muscle innervated or not innervated by the target nerve may be used to guide lead placement and then increase stimulus intensity until sufficient paresthesias are elicited in the painful region. Minimal muscle contraction may be acceptable if it is well tolerated by the patient in exchange for significant pain relief and if it does not lead to additional discomfort or fatigue.

If stimulation evokes muscle contraction at a lower stimulus threshold than paresthesia (e.g. if TMUS≤TSUP) and contraction leads to discomfort, then a lower stimulus frequency (e.g., 12 Hz) may be used because low frequencies (e.g., 4-20 Hz) have been shown to minimize discomfort due to muscle contraction and provide >50% relief of shoulder pain in stroke patients while still inhibiting transmission of pain signals in the central nervous system in animals. If continued muscle contraction leads to pain due to fatigue, change the duty cycle, using parameters shown to reduce muscle fatigue and related discomfort in the upper extremity (e.g. 5 s ramp up, 10 s on, 5 s ramp down, 10 s off).

If stimulation fails to elicit paresthesia in all areas of pain, then a second percutaneous lead (not shown) may need to be placed to stimulate the nerves that are not activated by the first lead 12.

If stimulation is successful, i.e., if the screening test and/or home-trial are successful, the patient's percutaneous system (see FIG. 14) may be converted into a fully implanted system by replacing the external pulse generator 28 with an implantable pulse generator that is implanted in a convenient area (see FIG. 24D) (e.g., in a subcutaneous pocket over the hip or in the subclavicular area). In one embodiment, the electrode lead 12 used in the screening test and/or home-trial may be totally removed and discarded, and a new completely implantable lead may be tunneled subcutaneously and coupled to the implantable pulse generator. In an alternative embodiment, a two part lead may be incorporated in the screening test and/or home-trial where the implantable part is completely under the skin and connected to a percutaneous connector (i.e., extension) that can be discarded after removal. The implantable part may then be tunneled and coupled to the implantable pulse generator, or a new sterile extension may be used to couple the lead to the implantable pulse generator.

Figure 29A:
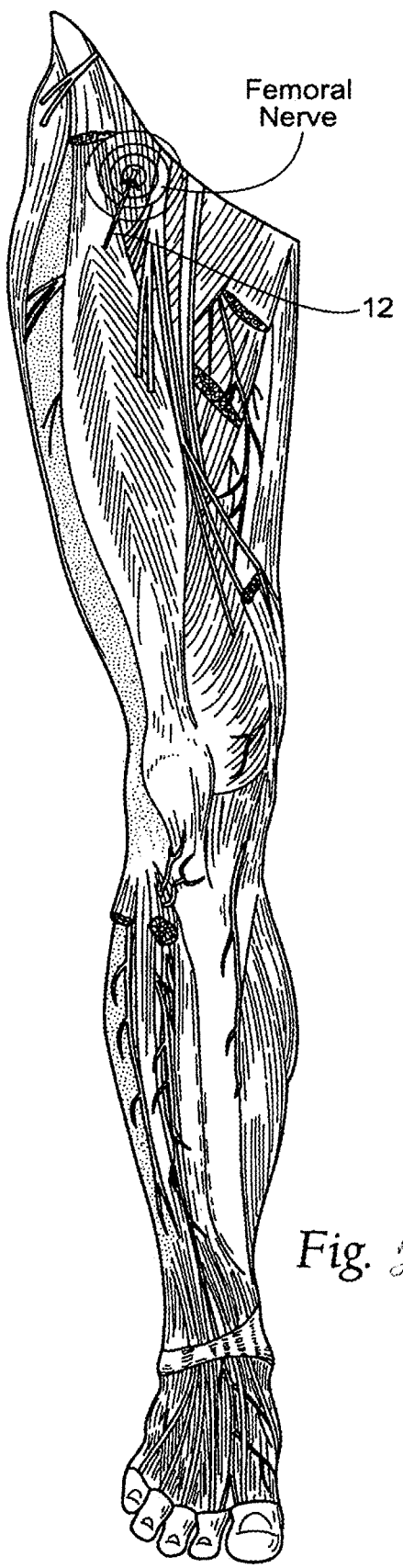
FIGS. 29A, 29B, and 29C are schematic anatomic views of a system for applying nerve of passage stimulation to a femoral nerve.

Alternatively, when the targeted nerve of passage includes one or more nerves of the lumbar plexus or sacral plexus, the approach may be either a posterior (shown in FIG. 29A) or an anterior approach (shown in FIG. 30A), similar to those used for regional anesthesia of the same targeted nerve of passage, except that the approach is used for placement through an introducer of stimulation lead(s) in electrical proximity to but spaced away from a nerve of passage, and not for regional anesthesia. Unlike regional anesthesia, the approach to nerves of the lumbar plexus or sacral plexus do not involve the application of anesthesia to the nerve, and, when the introducer is withdrawn, the lead(s) may be left behind to desired stimulation of the target nerve of passage.

For example, when the targeted nerve of passage includes the sciatic nerve (see FIG. 31A), the introducer(s) 30 and/or lead(s) 12 may be directed towards the sciatic nerve using a posterior approach, such as the transgluteal approach or subgluteal approach, which are both well described and commonly used in regional anesthesiology (Dalens et al. 1990; Bruelle et al. 1994; di Benedetto et al. 2001; Gaertner et al. 2007).

This approach allows lead placement near a targeted nerve of passage with a simple, quick (e.g. less than 10 minutes) outpatient procedure that may be performed in a standard community-based clinic. This makes possible widespread use and provides a minimally-invasive screening test to determine if patients will benefit from the device before receiving a fully implanted system.

The landmarks for the transgluteal approach may include the greater trochanter and the posterior superior iliac spine. The introducer 30 may be inserted distal (e.g. approximately 2 cm to 6 cm, preferably 4 cm, in a preferred embodiment) to the midpoint between the greater trochanter and the posterior iliac spine. As a non-limiting example of patient positioning, the patient may be in a lateral decubitus position and tilted slightly forward in a preferred embodiment. The landmarks for the subgluteal approach may include the greater trochanter and the ischial tuberosity. The introducer may be inserted distal (e.g. approximately 2 cm to 6 cm, preferably 4 cm, in the preferred embodiment) to the midpoint between the greater trochanter and the ischial tuberosity.

For example, when the targeted nerve of passage includes the femoral nerve (see FIG. 31A), percutaneous leads 12 may be directed towards the femoral nerve using an anterior approach. The landmarks may include the inguinal ligament, inguinal crease, and femoral artery. The subject may be in the supine position with ipsilateral extremity slightly (approximately 10 to 20 degrees) abducted. The introducer may be inserted near the femoral crease but below the inguinal crease and approximately 1 cm lateral to the pulse of the femoral artery.

The size and shape of tissues, such as the buttocks, surrounding the target nerves may vary across subjects, and the approach may be modified as needed to accommodate various body sizes and shapes to access the target nerve.

In non-amputee patients, introducer placement can be often guided by muscle response to electrical stimulation, but the muscle response may not be available in amputees, or may not be available and/or be unreliable in other situations (e.g., a degenerative diseases or condition such as diabetes of impaired vascular function in which the nerves are slowly degenerating, progressing from the periphery, or due to trauma).

In these situations, placement may be guided by the individual's report of stimulus-evoked sensations (paresthesias) as the introducer is placed during test stimulation. Additionally, the response of remaining muscles to stimulation may also be used to guide placement of the introducer and electrode.

Figure 31:
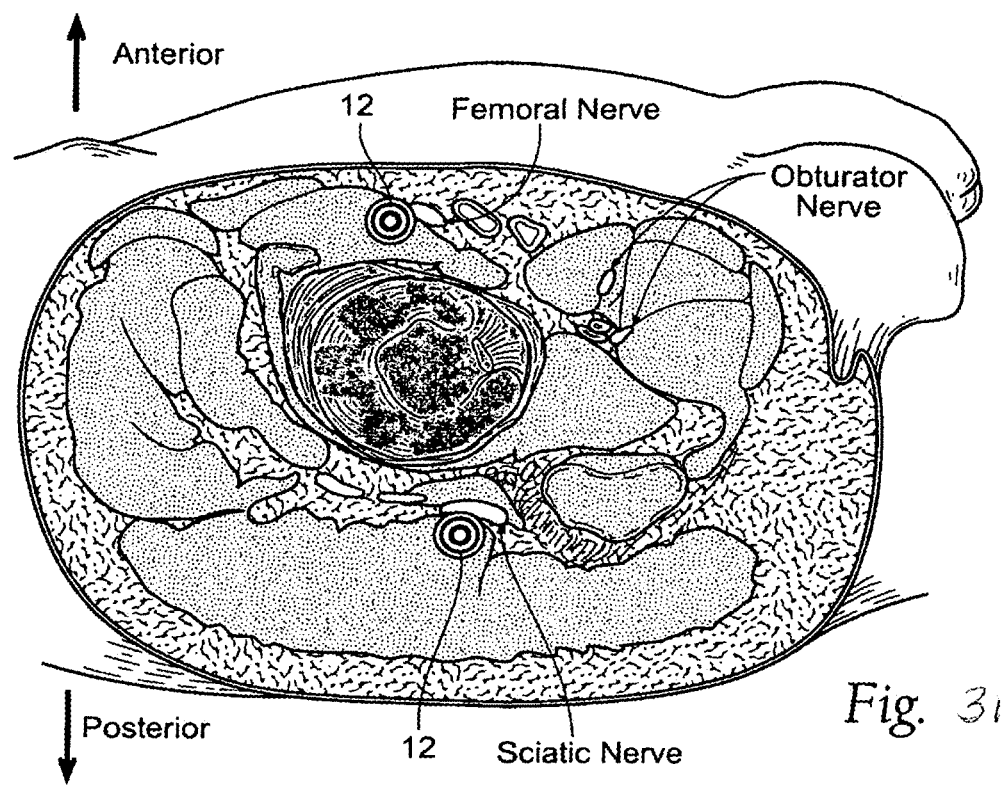
FIGS. 31A and 31B are schematic sectional anatomic views of systems for applying nerve of passage stimulation to a femoral nerve and a sciatic/tibial nerve.
Figure 31:
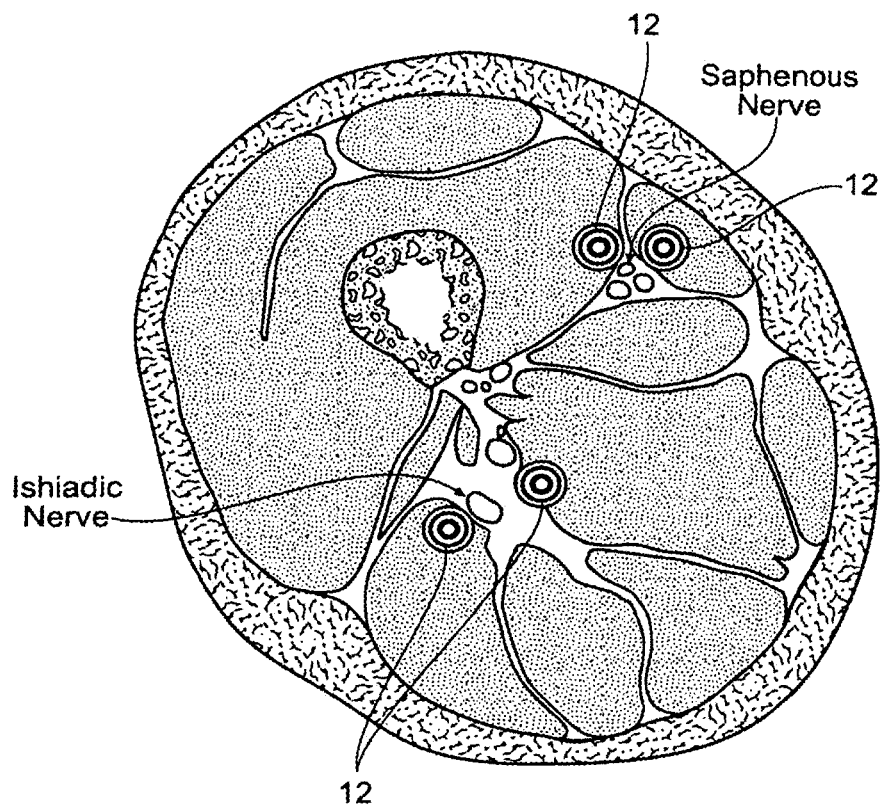

As shown in FIG. 31B, more than a single lead 12 may be placed around a given nerve of passage, using either an anterior approach femoral nerve) a posterior approach (e.g., sciatic nerve). As FIGS. 32A, B, and C show, one or more leads 12 can be placed at different superior-inferior positions along a nerve of passage and/or along different nerves of passage.

Figure 29B:
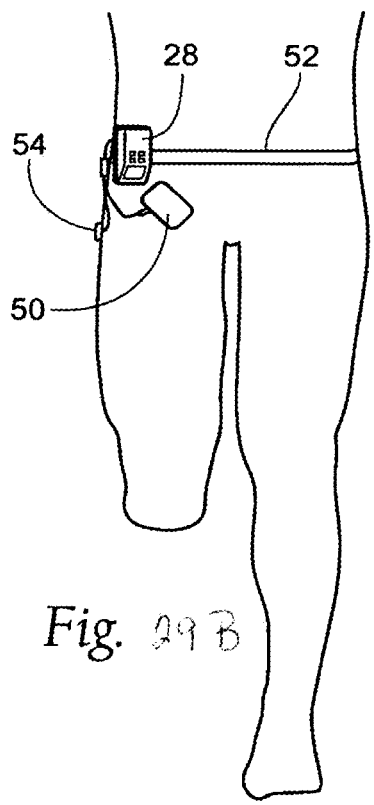
Figure 29C:
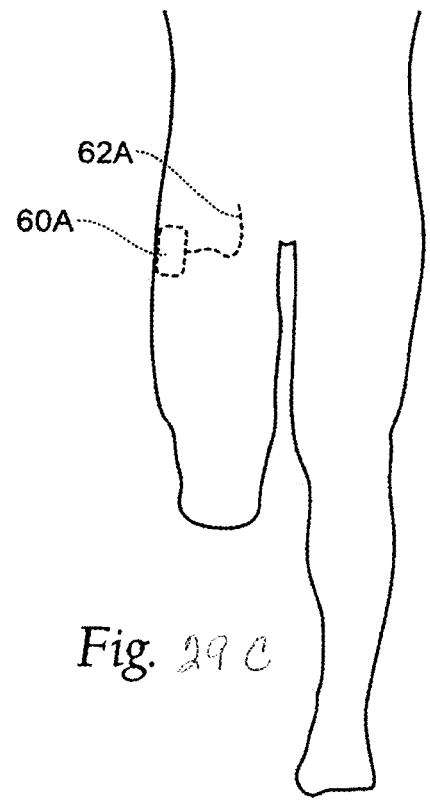
Figure 30:
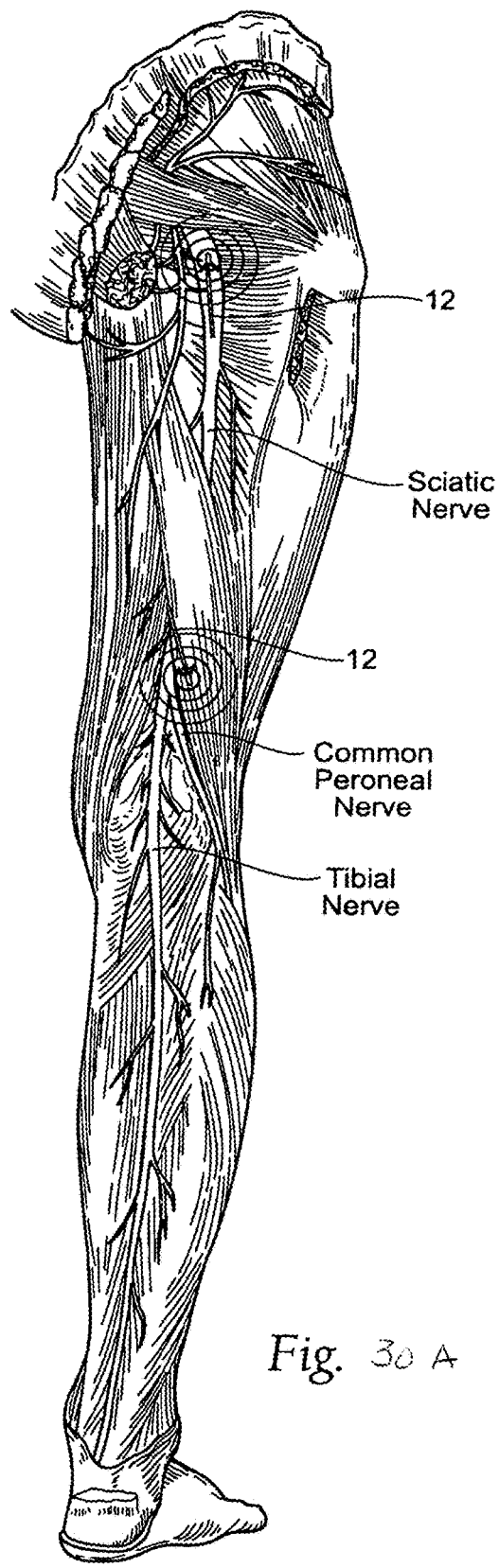
FIGS. 30A, 30B, and 30C are schematic anatomic views of a system for applying nerve of passage stimulation to a sciatic/tibial nerve.
Figure 30:
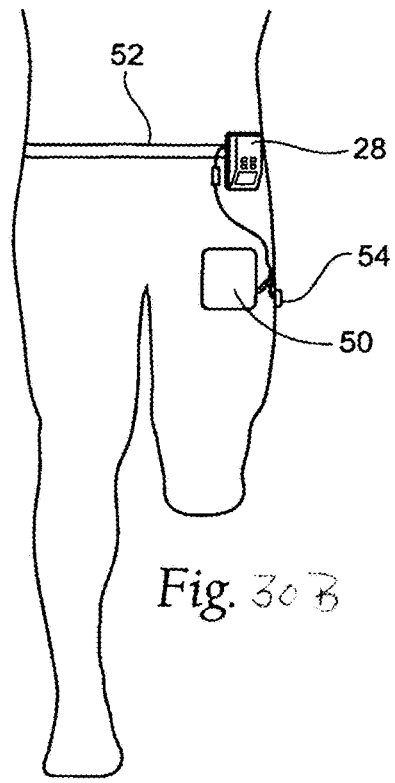
Figure 30:
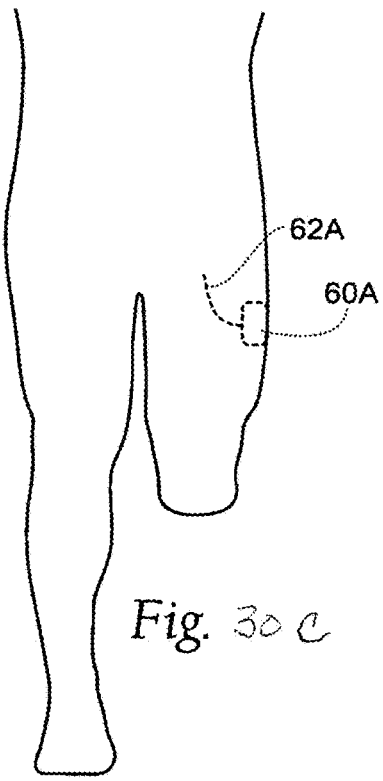

As FIG. 29B (anterior approach, e.g., femoral nerve) and 17B (posterior approach, e.g., sciatic nerve) show, the lead 12 can be coupled to an external pulse generator 28 worn, e.g., on a belt 52, for a trial or temporary stimulation regime. In this arrangement, the lead 12 is covered with a bandage 50, and a surface electrode 54 serves as a return electrode. The external/percutaneous system shown in FIGS. 29B and 30B may be replaced by an implanted system using an implanted pulse generator 60 and intramuscular and tunneled leads 62, as shown in FIGS. 29C and 30C, respectively. In this arrangement, the case of the implanted pulse generator 60A comprises the return electrode.

D. Stimulation Parameters

Control of the stimulator and stimulation parameters may be provided by one or more external controllers. In the case of an external stimulator, the controller may be integrated with the external stimulator. The implanted pulse generator external controller (i.e., clinical programmer) may be a remote unit that uses RF (Radio Frequency) wireless telemetry communications (rather than an inductively coupled telemetry) to control the implanted pulse generator. The external or implantable pulse generator may use passive charge recovery to generate the stimulation waveform, regulated voltage (e.g., 10 mV to 20 V), and/or regulated current (e.g., about 10 μA to about 50 mA). Passive charge recovery is one method of generating a biphasic, charge-balanced pulse as desired for tissue stimulation without severe side effects due to a DC component of the current.

The neurostimulation pulse may by monophasic, biphasic, and/or multi-phasic. In the case of the biphasic or multi-phasic pulse, the pulse may be symmetrical or asymmetrical. Its shape may be rectangular or exponential or a combination of rectangular and exponential waveforms. The pulse width of each phase may range between e.g., about 0.1 μsec. to about 1.0 sec., as non-limiting examples. The preferred neurostimulation waveform is cathodic stimulation (though anodic will work), biphasic, and asymmetrical.

Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

The stimulating frequency may range from e.g., about 1 Hz to about 300 Hz, and the frequency of stimulation may be constant or varying. In the case of applying stimulation with varying frequencies, the frequencies may vary in a consistent and repeatable pattern or in a random (or pseudo random) fashion or a combination of repeatable and random patterns.

In a representative embodiment, the stimulator is set to an intensity (e.g. 1-2 mA (or 0.1-40 mA, or 0.01-200 mA), 100-300 μs (or 40-1000 us, or 1-10,000 us)) sufficient to activate the targeted nerve of passage at some distance (e.g. 1 mm) away (from the targeted nerve of passage). If the stimulus intensity is too great, it may generate muscle twitch(es) or contraction(s) sufficient to disrupt correct placement of the lead. If stimulus intensity is too low, the lead may be advanced too close to the targeted nerve of passage (beyond the optimal position), possibly leading to incorrect guidance, nerve damage, mechanically evoked sensation (e.g. pain and/or paresthesia) and/or muscle contraction (i.e. when the lead touches the nerve of passage), inability to activate the target nerve fiber(s) without activating non-target nerve fiber(s), improper placement, and/or improper anchoring of the lead (e.g. the lead may be too close to the nerve and no longer able to anchor appropriately in the muscle tissue).

In a representative embodiment, the stimulator is set to a frequency (e.g. 0.5-12 Hz (or 0.1-20 Hz, or 0.05-40 Hz)) low enough to evoke visible muscle twitches (i.e. non-fused muscle contraction) and/or muscle contraction(s) of the targeted muscle(s) innervated by the target nerve of passage, but high enough that that the targeted nerve of passage will be activated before the lead is advanced beyond the optimal position.

As an alternative to using muscle twitch(es) or contraction(s) as indicator(s) of lead placement (distance from the nerve of passage to electrode contact), patient sensation could be used instead to indicate lead location relative to the targeted nerve of passage. Any combination of stimulus parameters that evoke sensation(s) may be used.

Some stimulus parameters may evoke a more desirable response (e.g. more comfortable sensation, or a sensation that may be correlated with or specific to the specific target nerve fiber(s) within the targeted nerve of passage. As an example, higher frequencies (e.g. 12 Hz, or 4 Hz, or 0.1 Hz) may evoke sensation(s) or comfortable paresthesia(s) in the region(s) of pain or in alternate target region(s) (real or phantom) and though they may (or may not) also evoke muscle contraction(s), the muscle contraction(s) may not be noticeable (e.g. stimulus intensity may not be sufficient to evoke a contraction or a twitch from the present lead location or stimulus intensity may be sufficient to evoke contraction but the muscle contraction is fused (and no longer visually twitching), making it difficult to observe visually, unless EMG is used). To take advantage of both potential indicator responses (muscle twitch and patient sensation), higher frequencies may be applied intermittently (at lower frequencies), where the higher frequencies (e.g. 20-120 Hz, or 12-200 Hz) would normally caused fused muscle contraction if they were applied continuously but they are applied at an intermittent frequency (e.g. 0.5-4 Hz, or 0.1-11 Hz) that is low enough to allow the muscle to relax during the gaps between the bursts of stimulation, making it easier to visualize while still generating patient sensation at a higher frequency, allowing both muscle twitch and patient sensation to be used simultaneously as indicators of lead location relative to the targeted nerve of passage.

While stimulation is being applied, the lead (non-limiting examples of the lead could include a single or multi-contact electrode that is designed for temporary (percutaneous) or long-term (implant) use or a needle electrode (used for in-office testing only)) may be advanced (e.g. slowly advanced) towards the targeted nerve of passage until the desired indicator response (e.g. muscle twitch, muscle contraction, patient sensation, and/or some combination) is obtained. The intensity may then be decreased (e.g. gradually decreased) as the lead is advanced (e.g. advanced slowly) closer to the targeted nerve of passage until the desired indicator responses) may be obtained at smaller intensity(ies) within the target range (e.g. 0.1-1.0 mA (or 0.09-39 mA, or 0.009-199 mA), 100-300 μs (or 40-1000 us, or 1-10,000 μs)) at some distance (e.g. X2 mm, where X2<X1, and (as a non-limiting example) X1 may be multiple times larger than X2, such as $X1 \geq 2*X2$, or $X1 \geq 5*X2$, or $X1 \geq 20*X2$) from the target nerve. If specific response(s) (e.g. desired response(s) and/or undesired response(s)) can be obtained at a range of intensities that are too low, then the lead may be located in a non-optimal location (e.g. too close to the target nerve(s)). Non-limiting examples of ranges of intensities that may be considered too low include those that are a fraction (e.g. $<2/3$, or $<1/5$, or $<1/10$) of the intensities that obtained the desired response(s) at X1.

The preferred stimulus intensities are a function of many variables, are meant to serve as non-limiting examples only, and may need to be scaled accordingly. As an example, if electrode shape, geometry, or surface area were to change, then the stimulus intensities may need to change appropriately. For example, if the intensities were calculated for a lead with an electrode surface area of approximately 20 $mm^2$, then they may need to be scaled down accordingly to be used with a lead with an electrode surface area of 0.2 $mm^2$ because a decrease in stimulating surface area may increase the current density, increasing the potential to activate excitable tissue (e.g. target and non-target nerve(s) and/or fiber(s)). Alternatively, if the intensities were calculated for a lead with an electrode surface area of approximately 0.2 $mm^2$, then the intensities may need to be scaled up accordingly to be used with a lead with an electrode surface area of 20 mm². Alternatively, stimulus intensities may need to be scaled to account for variations in electrode shape or geometry (between or among electrodes) to compensate for any resulting variations in current density. In a non-limiting example, the electrode contact surface area may be 0.1-20 mm², 0.01-40 mm², or 0.001-200 mm². In a non-limiting example, the electrode contact configuration may include one or more of the following characteristics: cylindrical, conical, spherical, hemispherical, circular, triangular, trapezoidal, raised (or elevated), depressed (or recessed), flat, and/or borders and/or contours that are continuous, intermittent (or interrupted), and/or undulating.

Stimulus intensities may need to be scaled to account for biological factors, including but not limited to patient body size, weight, mass, habitus, age, and/or neurological condition(s). As a non-limiting example, patients that are older, have a higher body-mass index (BMI), and/or neuropathy (e.g. due to diabetes) may need to have stimulus intensities scaled higher (or lower) accordingly (Bigeleisen et al 2009).

As mentioned above, if the lead is too far away from the targeted nerve of passage, then stimulation may be unable to evoke the desired response (e.g. muscle contraction(s), comfortable sensation(s) (or paresthesia(s)), and/or pain relief) in the desired region(s) at the desired stimulus intensity(ies). If the lead is too close to the targeted nerve of passage, then stimulation ma be unable to evoke the desired response(s) (e.g. muscle contraction(s), comfortable sensation(s) (or paresthesia(s)), anchor pain relief) in the desired region(s) at the desired stimulus intensity(ies) without evoking undesirable responses) (e.g. unwanted and/or painful muscle contraction(s), sensation(s) (or paresthesia(s)), increase in pain, and/or generation of additional pain in related or unrelated area(s)). In some cases, it may difficult to locate the optimal lead placement (or distance from the targeted nerve of passage and/or it may be desirable to increase the range stimulus intensities that evoke the desired response(s) without evoking the undesired response(s) so alternative stimulus waveforms and/or combinations of leads and/or electrode contacts may be used. A non-limiting example of alternative stimulus waveforms may include the use of a pre-pulse to increase the excitability of the target fiber(s) and/or decrease the excitability of the non-target fiber(s).

Those skilled in the art will recognize that, for simplicity and clarity, the full structure and operation of all devices and processes suitable for use with the present invention is not being depicted or described herein. Instead, only so much of an implantable pulse generator and supporting hardware as is unique to the present invention or necessary for an understanding of the present invention is depicted and described. The remainder of the construction and operation of the IPGs described herein may conform to any of the various current implementations and practices known in the art.

VII. Representative Indications for Chronic or Temporary Pain Therapy

Localized pain in any area of the body (e.g., the skin, bone, joint, or muscle) can be treated with by applying electrical stimulation to a muscle in electrical contact with but spaced from a targeted nerve of passage. Electrical stimulation of nerves of passage works by interfering with or blocking pain signals from reaching the brain, as FIG. 10 schematically shows.

Many pain indications can be treated by nerves of passage stimulation.

Pain in the leg may occur in areas such as the thigh, calf, hip, shin, knee, foot, ankle, and toes. There may be multiple causes of leg pain, including but not limited to injury (e.g. traumatic) to a muscle, joint, tendon, ligament or bone; muscle or ligament damage; ligament sprain, muscle or tendon strain; disease or disorders; phlebitis, swelling, or inflammation; claudication; insufficient blood flow into (arterial insufficiency) or away from (venous insufficiency) a part of the leg or foot; ischemia; peripheral artery disease; arthritis; tumor (malignant or benign); peripheral neuropathy; diabetic peripheral neuropathy; and post herpetic neuralgia.

For example, peripheral artery disease can cause pain (especially during activity such as walking or running) because the effective narrowing of the arteries leads to a decrease in the supply of blood and therefore in the supply of nutrients such as oxygen to the active muscles, leading to pain. This phenomenon can occur in almost in area of the body but may be more common in the leg, especially parts of the lower leg, such as the calf. Activity is not always required to elicit pain and pain may occur even at rest (without activity or exercise). Nerve entrapment, compression, injury or other types of damage may cause pain in the areas innervated by the damaged nerve, which can lead to referred pain in an area distal to the injury.

The femoral nerve has anterior branches (intermediate cutaneous nerve and medial cutaneous nerve) and posterior branches. The saphenous nerve (branch of the femoral nerve) provides cutaneous (skin) sensation in the medial leg. Other branches of the femoral nerve innervate structures (such as muscles, joints, and other tissues) in the thigh and around the hip and knee joints. As an example, branches of the femoral nerve innervate the hip joint, knee joint, and the four parts of the Quadriceps femoris (muscle): Rectus femoris (in the middle of the thigh) originates on the ilium and covers most of the other three quadriceps muscles. Under (or deep to) the rectus femoris are the other 3 of the quadriceps muscles, which originate from the body of the femur. Vastus lateralis (on the outer side of the thigh) is on the lateral side of the femur. Vastus medialis (on the inner part thigh) is on the medial side of the femur. Vastus intermedius (on the top or front of the thigh) lies between vastus lateralis and vastus medialis on the front of the femur. Braches of the femoral nerve often innervate the pectineus and Sartorius muscles arises.

The sciatic nerve has branches that innervate the biceps femoris, semitendinosus, semimembranosus, and adductor rnagnus muscles, 2 major branches of the sciatic nerve are the tibial and common peroneal nerves that innervate much of the lower leg (around and below the knee). For example, the tibial nerve innervates the gastrocnemius, popliteus, soleus and plantaris muscles and the knee joint. Most of the foot is innervated by the tibial and peroneal nerve.

For example, claudication pain (occurring in the calf muscle) could be treated by nerves of passage stimulation by placing the lead in the gluteus muscle near the sciatic nerve, which passes by the gluteus muscle on its way to innervate the calf muscle.

In general pain due to poor blood flow to an area or damage to an area can be relieved by stimulation of the nerve innervating that area. Since diabetic neuropathy typically leads to pain in the more distal areas (toes/foot), stimulation of the sciatic nerve can relive that pain. Pain in the skin of the medial (inner) calf can be relieved by stimulation of the femoral nerve. Pain in the front of the thigh (quad's) can be relieved by stimulation of the femoral nerve. If pain overlaps more than one area, stimulation of multiple nerves (e.g., sciatic and femoral nerves) can be beneficial.

Stimulation of the intercostal nerves (originating from the Thoracic nerve roots (T1-12)) can relieve pain in regions innervated by the intercostal nerves such as pain from intercostal neuralgia or post herpetic neuralgia. The pain may be confined to the area dermatomic area) innervated by 1 or 2 nerves and may follow outbreak (and recovery) of herpes zoster. The pain may last up to several months or years in some patients and may be caused by nerve irritation or damage due to herpes zoster.

Amputation (phantom) pain can also be treated by nerves of passage stimulation. For example, upper extremity stimulation of spinal nerves passing through the brachial plexus can relive phantom pain that results from amputation of an upper limb. Likewise, lower extremity stimulation of spinal nerves passing through the lumber plexus sacral plexus (e.g., the sciatic nerve or the femoral nerve) can relive phantom pain that results from amputation of a lower limb.

VIII. Conclusion

In "nerves of passage" stimulation, the lead is placed in a muscle by which the targeted nerve passes, but stimulation actually relieves pain that is felt distal (downstream) from where the lead is placed. In "nerves of passage" stimulation, the lead can be placed in a muscle that is conveniently located near a nerve trunk that passes by the lead on the way to the painful area. The key is that the lead is placed in a muscle that is not the target (painful) muscle, but rather a muscle that is proximal (upstream) from the painful region because the proximal muscle is a more convenient and useful location to place the lead.

The advantages of nerves of passage stimulation can be recognized by anesthesiologists who are used to placing needles deeper in the muscle near nerves of passage Anesthesiologists are accustomed to placing needles proximal (upstream) from the areas of pain to numb the areas downstream. Anesthesiologists already use ultrasound and the electro-location techniques that would be needed to place leads to access nerves of passage.

Nerves of passage stimulation provides stimulation-generated paresthesias (that ideally overlap with the area of pain) but does not require evoking a muscle contraction to place the lead correctly. The target regions in which pain is felt and which are targeted for generation of paresthesia are not the same region in which the lead is placed. This is an advantage because physicians (e.g. anesthesiologists) who will typically be placing the lead are accustomed to using paresthesias (sensory feedback description of from the patient) to guide lead placement and tuning of stimulation parameters.

Evoking muscle contraction with stimulation is not required for pain relief or lead location. Evoking muscle contraction with stimulation may help in relieving pain or placing the lead, but it is not required. It is an advantage that muscle contraction is not required because it allows this method to treat pains in which muscle contraction cannot be evoked (e.g. in the case of amputation pain in which the target area has been amputated and is no longer physically present or other cases of nerve damage either due to a degenerative diseases or conditions such as diabetes of impaired vascular function, in which the nerves are slowly degenerating, progressing from the periphery, or due to trauma.

In nerves of passage stimulation, the primary targeted pain area is distal to the lead, meaning that the lead is in between the major area in which pain (e.g. the worst, most troubling, or most interfering pain) is felt and the center of the body (e.g. the spinal cord)).

Imaging (e.g., ultrasound or an alternate imaging technique, e.g. fluoroscopy) may be used to improve lead placement near nerves of passage. Ultrasound may improve lead placement in the form of increasing the total speed of the procedure (shortening the procedure's duration, not necessarily increasing the speed at which the lead is advanced in the form of locating the lead in a more optimal location (to improve recruitment of the target fibers in the target nerve and minimize recruitment of non-target fibers (e.g. c fibers, other non-target sensory fibers, motor fibers, etc.) in either the target nerve and/or in non-target nerve(s); in the form of minimizing risk and/or damage to the patient during placement of the lead (by avoiding blood vessels, organs, bones, ligaments, tendons, lymphatic vessels, &/or other structures) that may be damaged. One reason that imaging may be useful is that some nerves of passage are (but do not have to be) located relatively deeply. Fluoroscopy is not required to place the lead. It may help, but it is not required. Imaging is not required.

The patient is not required to give verbal, written, or other type of feedback or indication of what they feel as the lead is being advanced towards the nerve of passage if muscle contraction or imaging is used to guide lead placement, but patient feedback during lead advancement may improve lead placement in some patients, especially in cases where (distal) muscle contraction cannot be used to confirm correct lead placement (e.g. amputees, nerve injury, nerve degeneration (e.g. due to vascular dysfunction, diabetes, etc), stimulation of a sensory nerve). The patient may indicate sensations during tuning of stimulus intensity (but this is a different step in the process and is performed after the lead has been correctly positioned). As non-limiting examples, those sensations reported by the patient may include first sensation (minimum stimulus intensity that evokes a sensation), level of comfort, maximum tolerable sensation, pain, qualities &/or descriptions of the sensations.

The region in which the patient perceives stimulation-induced sensations and/or paresthesias may be an important indicator of the potential success of the therapy (e.g. used in screening potential candidates), and the stimulation parameters (including but not limited to lead location) may be adjusted so that the region in which paresthesias are perceived overlaps with the region of pain.

As an alternative to using perception of stimulation induced sensations and/or paresthesia, the level of pain and/or change in the intensity of pain during and/or due to stimulation may be used to adjust stimulation parameters (including but not limited to lead location).

The foregoing is considered as illustrative only of the principles of the invention. Furthermore, since numerous modifications and changes will readily occur to those skilled in the art, it is not desired to limit the invention to the exact construction and operation shown and described. While the desired embodiment has been described, the details may be changed without departing from the invention.

Various features of the invention are set forth in the following Claims.

The invention claimed is:

1. A method to reduce and/or relieve pain in a painful region comprising:
   percutaneously inserting a coiled lead into a patient, wherein the coiled lead comprises an electrode and wherein the electrode is in electrical proximity but spaced away from a peripheral nerve;

stimulating the peripheral nerve innervating the painful region via the electrode positioned outside of the painful region, wherein the stimulation comprises a frequency of between 1 and 300 Hz; and activating the peripheral nerve to alleviate pain in the painful region without functional nerve stimulation at a motor point and without damaging the peripheral nerve.

2. The method of claim 1, wherein the frequency is between 4 and 20 Hz.

3. The method of claim 1, wherein the frequency is between 1 and 12 Hz.

4. The method of claim 1, wherein the frequency is 12 Hz.

5. The method of claim 1, wherein the frequency is 100 Hz.

6. The method of claim 1, wherein the stimulation comprises a pulse duration of between 1 and 200 μs.

7. The method of claim 6, wherein the pulse duration is between 5 and 100 μs.

8. The method of claim 1, wherein the stimulation comprises an intensity of between 0.1 and 40 mA.

9. The method of claim 8, wherein the intensity comprises 30 mA.

10. The method of claim 1 further comprising evoking paresthesia over at least a portion of the painful region.

11. The method of claim 10, wherein the paresthesia is evoked over all of the painful region.

12. The method of claim 1, wherein the stimulation comprises a pulse duration of between 5 and 100 μs, the stimulation comprises an intensity of 30 mA and the frequency is 12 Hz.

13. The method of claim 12 further comprising evoking paresthesia over at least a portion of the painful region.

14. A system to reduce and/or relieve pain in a painful region, the system comprising:
an electrode positioned in electrical proximity to but spaced away from a peripheral nerve innervating the painful region and wherein the electrode is positioned outside of the painful region; and
an electrical stimulator in operative communication with the electrode, the electrical stimulator applying stimulation through the electrode to the peripheral nerve, wherein the stimulation comprises a frequency of between 1 and 300 Hz and the stimulation is configured to activate the peripheral nerve to alleviate pain in the painful region without functional nerve stimulation at a motor point and without damaging the peripheral nerve.

15. The system of claim 14, wherein the frequency of the stimulation applied by the electrical stimulator is between 4 and 20 Hz.

16. The system of claim 14, wherein the frequency of the stimulation applied by the electrical stimulator is between 1 and 12 Hz.

17. The system of claim 14, wherein the frequency of the stimulation applied by the electrical stimulator is 12 Hz.

18. The system of claim 14, wherein the frequency of the stimulation applied by the electrical stimulator is 100 Hz.

19. The system of claim 14, wherein the stimulation applied by the electrical stimulator comprises a pulse duration of between 1 and 200 μs.

20. The system of claim 14, wherein the pulse duration of the stimulation applied by the electrical stimulator is between 5 and 100 μs.

21. The system of claim 14, wherein the stimulation applied by the electrical stimulator comprises an intensity of between 0.1 and 40 mA.

22. The system of claim 21, wherein the intensity comprises 30 mA.

23. A method to reduce and/or relieve pain in a painful region comprising:
percutaneously inserting a coiled lead into a patient, wherein the coiled lead comprises an electrode;
positioning the electrode into adipose or connective tissue outside of the painful region and in electrical proximity to but spaced away from a peripheral nerve;
stimulating the peripheral nerve innervating the painful region via the electrode, wherein the stimulation comprises:
a frequency of between 1 and 300 Hz;
a pulse duration of between 1 and 200 μs; and
an intensity of between 0.1 and 40 mA; and
activating the peripheral nerve to alleviate pain in the painful region without functional nerve stimulation at a motor point and without damaging the peripheral nerve.

24. The method of claim 23, wherein the frequency is between 4 and 20 Hz.

25. A system to alleviate pain, the system comprising:
a coiled wire lead having a thickness and a diameter configured for percutaneous insertion into a portion of a body that is proximal to a residual limb;
a plurality of electrodes each formed integrally on the lead, wherein the electrodes are spaced apart from one another with an insulated portion positioned between at least two of the plurality of electrodes and wherein the electrodes are configured to be positioned: i) inside the body, and ii) in electrical proximity to but spaced from a portion of at least one nerve; and
an electrical stimulation device operatively coupled to the lead and configured to apply electrical stimulation through the plurality of electrodes to the at least one nerve, to create tingling sensations in a region of residual or phantom pain.

26. A method to reduce and/or relieve pain in a painful region comprising:
percutaneously inserting a coiled lead into a patient, wherein the coiled lead comprises an electrode;
stimulating a peripheral nerve innervating the painful region via an electrode positioned in electrical proximity to but spaced from the peripheral nerve and outside of the painful region, wherein the stimulation comprises a frequency of about 12 Hz;
activating the peripheral nerve to alleviate pain in the painful region without functional nerve stimulation at a motor point and without damaging the peripheral nerve;
stimulating the peripheral nerve innervating the painful region via the electrode, wherein the stimulation comprises a frequency of about 100 Hz; and
activating the peripheral nerve to alleviate pain in the painful region without functional nerve stimulation at the motor point and without damaging the peripheral nerve.

* * * * *